(12) United States Patent
Foster et al.

(10) Patent No.: US 10,947,570 B2
(45) Date of Patent: Mar. 16, 2021

(54) MATERIALS AND METHODS UTILIZING BIOTIN PRODUCING MUTANT HOSTS FOR THE PRODUCTION OF 7-CARBON CHEMICALS

(71) Applicant: INV Nylon Chemicals Americas, LLC, Wilmington, DE (US)

(72) Inventors: Alexander Brett Foster, Yarm (GB); Stephen Thomas Cartman, Stockton-on-Tees (GB); Jonathan Kennedy, North Yorkshire (GB)

(73) Assignee: INV Nylon Chemicals Americas, LLC, Wilmington, DE (US)

(*) Notice: Subject to any disclaimer, the term of this patent is extended or adjusted under 35 U.S.C. 154(b) by 0 days.

(21) Appl. No.: 15/658,958

(22) Filed: Jul. 25, 2017

(65) Prior Publication Data
US 2018/0023102 A1    Jan. 25, 2018

Related U.S. Application Data

(60) Provisional application No. 62/366,565, filed on Jul. 25, 2016.

(51) Int. Cl.
| | | |
|---|---|---|
| C12N 15/52 | (2006.01) | |
| C12P 7/44 | (2006.01) | |
| C12P 7/62 | (2006.01) | |
| C12P 13/00 | (2006.01) | |
| C12P 7/24 | (2006.01) | |

(52) U.S. Cl.
CPC ............... *C12P 7/44* (2013.01); *C12N 15/52* (2013.01); *C12P 7/24* (2013.01); *C12P 7/62* (2013.01); *C12P 13/001* (2013.01); *C12P 13/005* (2013.01); *C12Y 102/01* (2013.01); *C12Y 102/99006* (2013.01); *C12Y 206/01* (2013.01); *C12Y 206/01018* (2013.01); *C12Y 301/02* (2013.01)

(58) Field of Classification Search
CPC ................. C12N 15/52; C12Y 206/01; C12Y 102/99006; C12Y 301/02
See application file for complete search history.

(56) References Cited

U.S. PATENT DOCUMENTS

| | | | |
|---|---|---|---|
| 6,083,712 A | 7/2000 | Birch et al. | |
| 6,277,609 B1 | 8/2001 | Eddy | |
| 6,284,500 B1 | 9/2001 | Kanzaki et al. | |
| 6,498,242 B1 | 12/2002 | Cheng et al. | |
| 7,695,949 B2 * | 4/2010 | Hohmann | C12P 13/02 435/252.3 |
| 2003/0233675 A1 | 12/2003 | Cao et al. | |
| 2007/0118916 A1 | 5/2007 | Puzio et al. | |

FOREIGN PATENT DOCUMENTS

| | | |
|---|---|---|
| WO | 2013/003744 A2 | 1/2013 |
| WO | 2014/105788 A2 | 7/2014 |
| WO | 2015/010103 A2 | 1/2015 |
| WO | 2015/175698 A1 | 11/2015 |
| WO | 2016/100894 A1 | 6/2016 |
| WO | 2016/106247 A1 | 6/2016 |
| WO | 2018/022595 A1 | 2/2018 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
International Search Report and Written Opinion received for PCT Patent Application No. PCT/US2017/ 043682, dated Dec. 1, 2017, 24 pages.
Shapiro et al., "Remarkable Diversity in the Enzymes Catalyzing the Last Step in Synthesis of the Pimelate Moiety of Biotin", Plos One, vol. 7, Issue 11, e49440, Nov. 2012, 11 Pages.
Agarwal et al., "Structure of the Erizynie-Acyl Carrier Protein (ACP) Substrate Gatekeeper Complex Required for Biotin Synthesis", Proceedings National Academy of Sciences (PNAS), vol. 109, No. 43, Oct. 2012, pp. 17406-17411.
Bower et al., "Cloning, Sequencing, and Characterization of the Bacillus Subtilis Biotin Biosynthetic Operon", Journal of Bacteriology, American Society for Microbiology, vol. 178, No. 14, Jul. 1996, pp. 4122-4130.
Altschul et al., "Gapped Blast and PSI-Blast: A New Generation of Protein Database Search Programs", Nucleic Acids Research (NCIB NIA NIH), Bethesda Md., NAR, vol. 25, No. 17, Jul. 16, 1997, pp. 3389-3402.
Anton et al., "Polyamides, Fibers", Encyclopedia of Polymer Science and Technology, vol. 3, Oct. 22, 2001, pp. 584-612.
Ausubel et al., "Current Protocols in Molecular Biology", Greene Publishing Associates/Wiley Interscience, New York, Supplement 30, section 7.7.18, 1987, 1 page.
Barker et al., "Enzymatic Reactions in the Degradation of 5-Aminovalerate by Clostridium Aminovalericum", The Journal of Biological Chemistry, vol. 262, No. 19, Jul. 5, 1987, pp. 8994-9003.
Bellmann et al., "Expression Control and Specificity of the Basic Amino Acid Exporter LysE of Corynebacterium Glutamicum", Microbiology, vol. 147, Jul. 1, 2001, pp, 1765-1774.
Bond-Watts et al., "Biochemical and Structural Characterization of the Trans-Enoyl-CoA Reductase from Treponema Denticola", Biochemistry, vol. 51, No. 34, 2012, pp. 6827-6837.
Bugg et al., "The Emerging Role for Bacteria in Lignin Degradation and Bio-Product Formation", Current Opinion in Biotechnology, vol. 22, 2011, pp. 394-400.

(Continued)

*Primary Examiner* — Richard G Hutson

(57) ABSTRACT

Disclosed are methods for regulating biosynthesis of at least one of pimelic acid, 7-aminoheptanoic acid, 7-hydroxyheptanoic acid, heptamethylenediamine, 7-aminoheptanoland 1,7-heptanediol (C7 building blocks) using a pathway having a pimeloyl-ACP intermediate, the method including the step of downregulating the activity of BioF. Also disclosed are recombinant hosts by fermentation in which the above methods are performed. Further disclosed are recombinant hosts for producing pimeloyl-ACP, the recombinant host including a deletion of a bioF gene.

12 Claims, 26 Drawing Sheets

Specification includes a Sequence Listing.

(56) References Cited

OTHER PUBLICATIONS

Cantu et al., "Thioesterases: A New Perspective Based on Their Primary and Tertiary Structures", Protein Science, vol. 19, May 17, 2010, pp. 1281-1295.
Demain et al., "Manual of Industrial Microbiology and Biotechnology", 2nd Edition, Scale-Up of Microbial Processes, ASM Press, 1999, 5 pages.
Elkins et al., "Substrate Specificity of the RND-Type Multidrug Efflux Pumps AcrB and AcrD of *Escherichia coli* is Determined Predominately by Two Large Periplasmic Loops", Journal of Bactiriology, vol. 184, No. 23, Dec. 2002, pp. 6490-6498.
Genbank, "7-Keto-8-Amino Pelargonic Acid Synthetase [*Escherichia coli*]", Accession No. AAA23516.1, Feb. 28, 1994, 1 page.
Genbank, "Acyl-[Acyl-Carrier Protein] Thioesterase [Lactobacillus Plantarum WCFS1]", Accession No. CCC78182.1, Feb. 27, 2015, 2 pages.
Genbank, "Acyl-ACP Thioesterase [Lactobacillus Brevis ATCC 367]", Accession No. ABJ63754.1, Jan. 28, 2014, 2 pages.
Genbank, "Adenosylmethionine-8-Amino-7-Oxononanoate Aminotransferase [Rhodohacter Sphaeroides 2.4.1]", Accession No. ABA81135.1, Jul. 20, 2015, 2 pages.
Genbank, "Alcohol Dehydrogenase [Geobacillus Stearothermophilus]", Accession No. CAA81612.1, Apr. 18, 2005, 2 pages.
Genbank, "Aminotransferase Class-III [Pseudomonas Syringae Pv. Syringae B728a]", Accession No. AAY39893.1, Jan. 31, 2014, 2 pages.
Genbank, "Biotin Synthesis Protein BioC, Putative [Bacillus Cereus ATCC 10987]", Accession No. AAS43086.1, Jan. 31, 2014, 1 page.
Genbank, "Fatty-Acid-CoA Ligase FadD9 [*Mycobacterium marinum* M]", Accession No. ACC40567.1, Jan. 31, 2014, 2 pages.
Genbank, "L-Alanine-Pimelyl CoA Ligase [Bacillus Subtilis]", Accession No. AAB17459.1, Oct. 24, 1996, 1 page.
Genbank, "NAD Dependent Epimerase/Dehydratase Family Protein [*Mycobacterium smegmatis* Str. MC2 155]", Accession No. ABK75684.1, Jan. 31, 2014, 2 pages.
Genbank, "ORF_o387 [*Escherichia coli* Str. K-12 Substr. MG1655]", Accession No. AAA69178.1, Jul. 1, 1995, 1 page.
Genbank, "Phosphopantetheinyl Transferase [Nocardia Iowensis]", Accession No. ABI83656.1, Jan. 3, 2007, 1 page.
Genbank, "Pimeloyl-ACP Methyl Ester Carboxylesterase [*Escherichia coli* Str. K-12 Substr. MG1655]", Accession No. AAC76437.1, Aug. 1, 2014, 3 pages.
Genbank, "Pimelyl CoA Synthetase [Bacillus Subtilis]", Accession No. AAB17457.1, Oct. 24, 1996, 1 page.
Genbank, "Probable Aminotransferase [Chromobacterium Violaceum ATCC 2472]", Accession No. AAQ59697.1, Jan. 31, 2014, 2 pages.
Genbank, "Probable Class III Aminotransferase [Pseudomonas Aeruginosa PAO1]", Accession No. AAG08191.1, Jan. 31, 2014, 2 pages.
Genbank, "Putative Fatty-Acid-CoA Ligase FADD9 [*Mycobacterium abscessus* Subsp. Bolletii 2B-0307]", Accession No. EIV11143.1, Dec. 19, 2014, 2 pages.
Genbank, "Putative Long-Chain Fatty-Acid-CoA Ligase [*Mycobacterium smegmatis* Str. MC2 155]", Accession No. ABK71854.1, Jan. 31, 2014, 2 pages.
Genbank, "Pyruvate Transaminase [Vibrio Fluvialis]", Accession No. AEA39183.1, Apr. 4, 2011, 1 page.
Genbank, "Thioester Reductase Domain Protein [Segniliparus Rotundus DSM 44985]", Accession No. ADG98140.1, Jan. 28, 2014, 2 pages.
Genbank, "Thioester Reductase Domain-Containing Protein [Segniliparus Rugosus ATCC BAA-974]", Accession No. EFV11917.1, Sep. 9, 2013, 3 pages.
Genbank, "Thioesterase II [*Escherichia coli*]", Accession No. AAA24665.1, Apr. 26, 1993, 1 page.
Genbank, "Unknown [*Saccharomyces cerevisiae*]", Accession No. CAA90836.1, Jul. 14, 2016, 2 pages.
Gloerich et al., "Peroxisomal Trans-2-Enoyl-CoA Reductase is Involved in Phytol Degradation", FEBS Letters, vol. 580, Mar. 10, 2006, pp. 2092-2096.
Harwood et al., "The Beta-Ketoadipate Pathway and the Biology of Self-Identity", Annual Review of Microbiology, vol. 50, Oct. 1996, pp. 553-590.
Hermann, Thomas, "Industrial Production of Amino Acids by Coryneform Bacteria", Journal of Biotechnology, vol. 104, 2003, pp. 155-172.
Huhn et al., "Identification of the Membrane Protein SucE and its Role in Succinate Transport in Corynebacterium Glutamicum", Applied Microbiology and Biotechnology, vol. 89, Jan. 2011, pp. 327-335.
Iwaki et al., "Cloning and Characterization of a Gene Cluster Involved in Cyclopentanol Metabolism in Comamonas Sp. Strain NCIMB 9872 and Biotransformations Effected by *Escherichia coli*-Expressed Cyclopentanone 1,2-Monooxygenase", Applied and Environmental Microbiology, vol. 68, No. 11, Nov. 2002, pp. 5671-5684.
Iwaki et al., "Identification of a Transcriptional Activator (ChnR) and a 6-Oxohexanoate Dehydrogenase (ChnE) in the Cyclohexanol Catabolic Pathway in Acinetobacter Sp. Strain NCIMB 9871 and Localization of the Genes That Encode Them", Applied and Environmental Microbiology, vol. 65, No. 11, Nov. 1999, pp. 5158-5162.
Jarboe, Laura R., "YqhD: A Broad-Substrate Range Aldehyde Reductase with Various Applications in Production of Biorenewable Fuels and Chemicals", Appl. Microbiol. Biotechnol., vol. 89, No. 2, 2011, pp. 249-257.
Jaremko et al., "The Initial Metabolic Conversion of Levulinic Acid in Cupriavidus Necator", Journal of Biotechnology, vol. 155, 2011, pp. 293-298.
Kaulmann et al., "Substrate Spectrum of ω-Transaminase from Chromobacterium Violaceum DSM30191 and its Potential for Biocatalysts", Enzyme and Microbial Technology, vol. 41, Oct. 2007, pp. 628-637.
Kim, Ki-Han, "Purification and Properties of a Mine α-Ketoglutarate Transaminase from *Escherichia coli*", The Journal of Biological Chemistry, vol. 239, No. 3, Mar. 1, 1964, pp. 783-786.
Kopke et al., "2,3-Butanediol Production by Acetogenic Bacteria, an Alternative Route to Chemical Synthesis, Using Industrial Waste Gas", Applied and Environmental Microbiology, vol. 77, No. 15, Aug. 2011, pp. 5467-5475.
Larroy et al., "Characterization of the Saccharomyces cerevisiae YMR318C (ADH6) Gene Product as a Broad Specificity NADPH-Dependent Alcohol Dehydrogenase: Relevance in Aldehyde Reduction", Biochem Journal, vol. 361, No. 1, Jan. 1, 2002, pp. 163-172.
Lee et al., "Synthesis of Pure Meso-2,3-Butanediol from Crude Glycerol Using an Engineered Metabolic Pathway in *Escherichia coli*", Applied Biochemistry and Biotechnology, vol. 166, No. 7, 2012, pp. 1801-1813.
Li et al., "Cupriavidus Necator JMP134 Rapidly Reduces Furfural with a Zn-Dependent Alcohol Dehydrogenase", Biodegradation, vol. 22, No. 6, 2011, pp. 1215-1225.
Lin, Steven, "Biotin Synthesis in *Escherichia coli*", University of Illinois at Urbana-Champaign, 2012, 140 pages.
Liu et al., "Two Novel Metal-Independent Long-Chain Alkyl Alcohol Dehydrogenases From Geobacillus Thermodenitrificans NG80-2", Microbiology, vol. 155, No. 6, Mar. 3, 2009, pp. 2078-2085.
Martin et al., "High-Titer Production of Monomeric Hydroxyvalerates from Levulinic Acid in Pseudomonas Putida", Journal of Biotechnology, vol. 139, No. 1, 2009, pp. 61-67.
Meijnen et al., "Improved p-Hydroxybenzoate Production by Engineered Pseudomonas Putida S12 by Using a Mixed-substrate Feeding Strategy", Applied Microbiology and Biotechnology, vol. 90, No. 3, 2011, pp. 885-893.
Myers et al., "Optimal Alignments in Linear Space", Bioinformatics, Computer Applications in the Biosciences, vol. 4, No. 1, 1988, pp. 11-17.
Naggert et al., "Cloning, Sequencing, and Characterization of *Escherichia coli* Thioesterase II", The Journal of Biological Chemistry, vol. 266, No. 17, Jun. 15, 1991, pp. 11044-11050.
Neyfakh, Alexander A., "The Multidrug Efflux Transporter of Bacillus Subtilis is a Structural and Functional Homolog of the Staphylococcus NorA Protein", Antimicrobial Agents Chemotherapy, vol. 36, No. 2, Feb. 1992, pp. 484-485.

(56) References Cited

OTHER PUBLICATIONS

Ng et al., "Quinolone Resistance Mediated by norA: Physiologic Characterization and Relationship to flqB, a Quinolone Resistance Locus on the *Staphylococcus aureus* Chromosome", Antimicrobial Agents and Chemotherapy, vol. 38, No. 6, Jun. 1994, pp. 1345-1355.
Nishimaki et al., "Studies on the Metabolism of Unsaturated Fatty Acids XIV, Purification and Properties of NADPH-Dependent Trans-2-Enoyl-CoA Reductase of *Escherichia coli* K-12", Journal of Biochemistry, vol. 95, No. 5, 1984, pp. 1315-1321.
Ohashi et al., "Continuous Production of Lactic Acid from Molasses by Perfusion Culture of Lactococcus Lactis Using a Stirred Ceramic Membrane Reactor", Journal of Bioscience and Bioengineering, vol. 87, No. 5, 1999, pp. 647-654.
Papanikolaou et al., "Citric Acid Production by Yarrowia Lipolytica Cultivated on Olive-Mill Wastewater-Based Media", Bioresource Technology, vol. 99, No. 7, 2008, pp. 2419-2428.
Pearson et al., "Improved Tools for Biological Sequence Comparison", Proceedings of the National Academy of Sciences, Biochemistry, vol. 85, Apr. 1988, pp. 2444-2448.
Perez-Pantoja et al., "Metabolic Reconstruction of Aromatic Compounds Degradation from the Genome of the Amazing Pollutant-Degrading Bacterium Cupriavidus Necator JMP134", FEMS Microbiology Reviews, vol. 32, Aug. 7, 2008, pp. 736-794.
Przybylski et al., "Third-Generation Feed Stocks for the Clean and Sustainable Biotechnological Production of Bulk Chemicals: Synthesis of 2-Hydroxyisobutyric Acid", Energy, Sustainability and Society, vol. 2, No. 11, 2012, 9 pages.
Ramsay et al., "Use of a Nylon Manufacturing Waste as an Industrial Fermentation Substrate", Applied and Environmental Microbiology, vol. 52, No. 1, Jul. 1986, pp. 152-156.
Refseq, "Malonyl-ACP O-Methyltransferase, SAM-Dependent [*Escherichia coli* Str. K-12 Substr. MG1655]", Accession No. NP_415298.1, Aug. 8, 2016, 3 pages.
Refseq, "Multispecies: 4'-Phosphopantetheinyl Transferase [Bacillus]", Accession No. WP_003234549.1, Apr. 23, 2017, 1 page.
Refseq, "Putrescine:2-Oxoglutaric Acid Aminotransferase, PLP-Dependent [*Escherichia coli* Str. K-12 Substr. MG1655]", Accession No. NP_417544.5, Aug. 8, 2016, 3 pages.
Samsonova et al., "Molecular Cloning and Characterization of *Escherichia coli* K12 ygjG Gene", BMC Microbiology, vol. 3, No. 2, Jan. 31, 2003, pp. 1-10.
Satoh et al., "Enzyme-Catalyzed Poly(3-Hydroxybutyrate) Synthesis from Acetate with CoA Recycling and NADPH Regeneration in Vitro", Journal of Bioscience and Bioengineering, vol. 95, No. 4, 2003, pp. 335-341.
Seedorf et al., "The Genome of Clostridium Kluyveri, A Strict Anaerobe with Unique Metabolic Features", PNAS USA, vol. 105, No. 6, Feb. 12, 2008, pp. 2128-2133.
Shen et al., "Driving Forces Enable High-Titer Anaerobic 1-Butanol Synthesis in *Escherichia coli*", Applied and Environmental Microbiology, vol. 77, No. 9, May 2011, pp. 2905-2915.
Stanbury et al., "Principles of Fermentation Technology", 2nd edition, Aeration and Agitation, 1995, 14 pages.
Suzuki et al., "Acetylputrescine Deacetylase from Micrococcus Luteus K-11", Biochimica et Biophysica Acta (BBA)—General Subjects, vol. 882, Issue 1, Jun. 1986, pp. 140-142.
Suzuki et al., "GriC and GriD Constitute a Carboxylic Acid Reductase Involved in Grixazone Biosynthesis in Streptomyces Griseus", Journal of Antibiotics, vol. 60, No. 6, 2007, pp. 380-387.
Venkitasubramanian et al., "Aldehyde Oxidoreductase as a Biocatalyst: Reductions of Vanillic Acid", Enzyme and Microbial Technology, vol. 42, No. 2, Jan. 2008, pp. 130-137.
Wee et al., "Biotechnological Production of Lactic Acid and its Recent Applications", Food Technology and Biotechnology, vol. 44, No. 2, 2006, pp. 163-172.
Woolridge et al., "Efflux of the Natural Polyamine Spermidine Facilitated by the Bacillus Subtilis Multidrug Transporter Blt", The Journal of Biological Chemistry, vol. 272, No. 14, Apr. 4, 1997, pp. 8864-8866.
Yang et al., "Value-Added Uses for Crude Glycerol—a Byproduct of Biodiesel Production", Biotechnology for Biofuels, vol. 5, No. 13, 2012, pp. 1-10.
Yonaha et al., "4-Aminobutyrate : 2-Oxoglutarate Aminotransferase of Streptomyces Griseus : Purification and Properties", European Journal of Biochemistry, vol. 146, Jan. 1985, pp. 101-106.
Zhuang et al., "Divergence of Function in the Hot Dog Fold Enzyme Superfamily: The Bacterial Thioesterase YciA\"", Biochemistry, vol. 47, No. 9, Feb. 2, 2008 pp. 2789-2796.
Cronan et al., "Synthesis of the α,ω-dicarboxylic acid precursor of biotin by the canonical fatty acid biosynthetic pathway", Current opinion in chemical biology, vol. 15, No. 3, pp. 407-413, Mar. 2011 (Abstract Submitted).
Lin et al., "Closing in on complete pathways of biotin biosynthesis", Molecular BioSystems, vol. 7, No. 6, pp. 1811-1821, Jun. 2011.
Lin et al., "Biotin Synthesis Begins by Hijacking the Fatty Acid Synthetic Pathway", Nature Chemical Biology, vol. 6, Issue 9, pp. 682-688, Sep. 2010 (Abstract Submitted).
Youjun et al., "Paracoccus denitrificans possesses two BioR homologs having a role in regulation of biotin metabolism", Microbiologyopen, vol. 4, Issue 4, pp. 644-659, Aug. 2015.
Manandhar et al., "A Canonical Biotin Synthesis Enzyme, 8-Amino-7-Oxononanoate Synthase (BioF), Utilizes Different Acyl Chain Donors in Bacillus subtilis and *Escherichia coli*", Enzymology and Protein Engineering, vol. 84, Issue 1, pp. 1-13, Jan. 2018.
Manandhar et al., "Pimelic acid, the first precursor of theBacillus subtilisbiotin synthesis pathway, exists as the free acid and isassembled by fatty acid synthesis", Molecular Microbiology, vol. 104, Issue 4, pp. 595-607, 2017.
Examination Report received for EP application No. 17755579.4, dated Jun. 9, 2020, 23 pages.

\* cited by examiner

| SEQ ID NO | Organism | GENBANK reference | Amino acid sequence |
|---|---|---|---|
| 1 | Escherichia coli | AAA24665.1 | MSQALKNLLTLLNLEKIEEGLFRGQSEDLGLRQVFGGQVVGQALYAAKETVPEERLVHSF HSYFLRPGDSKKPIIYDVETLRDGNSFSARRVAAIQNGKPIFYMTASFQAPEAGFEHQKT MPSAPAPDGLPSETQIAQSLAHLLPPVLKDKFICDRPLEVRPVEFHNPLKGHVAEPHRQV WIRANGSVPDDLRVHQYLLGYASDLNFLPVALQPHGIGFLEPGIQIATIDHSMWFHRPFN LNEWLLYSVESTSASSARGFVRGEFYTQDGVLVASTVQEGVMRNHN |
| 2 | Mycobacterium marinum | ACC40567.1 | MSPITREERLERRIQDLYANDPQFAAAKPATAITAAIERPGLPLPQIIETVMTGYADRPA LAQRSVEFVTDAGTGHTTLRLLPHFETISYGELWDRISALADVLSTEQTVKPGDRVCLLG FNSVDYATIDMTLARLGAVAVPLQTSAAITQLQPIVAETQPTMIAASVDALADATELALS GQTATRVLVFDHHRQVDAHRAAVESARERLAGSAVVETLAEAIARGDVPRGASAGSAPGT DVSDDSLALLIYTSGSTGAPKGAMYPRRNVATFWRKRTWFEGGYEPSITLNFMPMSHVMG RQILYGTLCNGGTAYFVAKSDLSTLFEDLALVRPTELTFVPRVWDMVFDEFQSEVDRRLV DGADRVALEAQVKAEIRNDVLGGRYTSALTGSAPISDEMKAWVEELLDMHLVEGYGSTEA GMILIDGAIRRPAVLDYKLVDVPDLGYFLTDRPHPRGELLVKTDSLFPGYYQRAEVTADV FDADGFYRTGDIMAEVGPEQFVYLDRRNNVLKLSQGEFVTVSKLEAVFGDSPLVRQIYIY GNSARAYLLAVIVPTQEALDAVPVEELKARLGDSLQEVAKAAGLQSYEIPRDFIIETTPW TLENGLLTGIRKLARPQLKKHYGELLEQIYTDLAHGQADELRSLRQSGADAPVLVTVCRA AAALLGGSASDVQPDAHFTDLGGDSLSALSFTNLLHEIFDIEVPVGVIVSPANDLQALAD YVEAARKPGSSRPTFASVHGASNGQVTEVHAGDLSLDKFIDAATLAEAPRLPAANTQVRT VLLTGATGFLGRYLALEWLERMDLVDGKLICLVRAKSDTEARARLDKTFDSGDPELLAHY RALAGDHLEVLAGDKGEADLGLDRQTWQRLADTVDLIVDPAALVNHVLPYSQLFGPNALG TAELLRLALTSKIKPYSYTSTIGVADQIPPSAFTEDADIRVISATRAVDDSYANGYSNSK WAGEVLLREAHDLCGLPVAVFRCDMILADTTWAGQLNVPDMFTRMILSLAATGIAPGSFY ELAADGARQRAHYDGLPVEFIAEAISTLGAQSQDGFHTYHVMNPYDDGIGLDEFVDWLNE SGCPIQRIADYGDWLQRFETALRALPDRQRHSSLLPLLHNYRQPERPVRGSIAPTDRFRA AVQEAKIGPDKDIPHVGAPIIVKYVSDLRLLGLL |
| 3 | Mycobacterium smegmatis | ABK71854.1 | MTSDVHDATGVTETALDDEQSTRRIAELYATDPEFAAAAPLPAVVDAAHKPGLRLAEIL QTLFTGYGDRPALGYRARELATDEGGRTVTRLLPRFDTLTYAQVWSRVQAVAAALRHNFA QPIYPGDAVATIGFASPDYLTLDLVCAYLGLVSVPLQHNAPVSRLAPILAEVEPRILTVS AEYLDLAVESVRDVNSVSQLVVFDHHPEVDDHRDALARAREQLAGKGIAVTTLDAIADEG AGLPAEPIYTADHDQRLAMILYTSGSTGAPKGAMYTEAMVARLWTMSFITGDPTPVINVN FMPLNHLGGRIPISTAVQNGGTSYFVPESDMSTLFEDLALVRPTELGLVPRVADMLYQHH LATVDRLVTQGADELTAEKQAGAELREQVLGGRVITGFVSTAPLAAEMRAFLDITLGAHI VDGYGLTETGAVTRDGVIVRPPVIDYKLIDVPELGYFSTDKPYPRGELLVRSQTLTPGYY KRPEVTASVFDRDGYYHTGDVMAETAPDHLVYVDRRNNVLKLAQGEFVAVANLEAVFSGA ALVRQIFVYGNSERSFLLAVVVPTPEALEQYDPAALKAALADSLQRTARDAELQSYEVPA DFIVETEPFSAANGLLSGVGKLLRPNLKDRYGQRLEQMYADIAATQANQLRELRRAAATQ PVIDTLTQAAATILGTGSEVASDAHFTDLGGDSLSALTLSNLLSDFFGFEVPVGTIVNPA TNLAQLAQHIEAQRTAGDRRPSFTTVHGADATEIRASELTLDKFIDAETLRAAPGLPKVT TEPRTVLLSGANGWLGRFLTLQWLERLAPVGGTLITIVRGRDDAAARARLTQAYDTDPEL SRRFAELADRHLRVVAGDIGDPNLGLTPEIWHRLAAEVDLVVHPAALVNHVLPYRQLFGP NVVGTAEVIKLALTERIKPVTYLSTVSVAMGIPDFEEDGDIRTVSPVRPLDGGYANGYGN SKWAGEVLLREAHDLCGLPVATFRSDMILAHPRYRGQVNVPDMFTRLLLSLLITGVAPRS FYIGDGERPRAHYPGLTVDFVAEAVTTLGAQQREGVSYDVMNPHDDGISLDVFVDWLIR AGHPIDRVDDYDDWVRRFETALTALPEKRRAQTVLPLLHAFRAPQAPLRGAPEPTEVFHA AVRTAKVGPGDIPHLDEALIDKYIRDLREFGLI |

FIG. 9A

| SEQ ID NO | Organism | GENBANK reference | Amino acid sequence |
|---|---|---|---|
| 4 | Segniliparus rugosus | EFV11917.1 | MGDGEERAKRFFQRIGELSATDPQFAAAAPDPAVVEAVSDPSLSFTRYLDTLMRGYAERP ALAHRVGAGYETISYGELWARVGAIAAAWQADGLAPGDFVATVGFTSPDYVAVDLAAARS GLVSVPLQAGASLAQLVGILEETEPKVLAASASSLEGAVACALAAPSVQRLVVFDLRGPD ASESAADERRGALADAEEQLARAGRAVVVETLADLAARGEALPEAPLFEPAEGEDPLALL IYTSGSTGAPKGAMYSQRLVSQLWGRTPVVPGMPNISLHYMPLSHSYGRAVLAGALSAGG TAHFTANSDLSTLFEDIALARPTFLALVPRVCEMLFQESQRGQDVAELRERVLGGRLLVA VCGSAPLSPEMRAFMEEVLGFPLLDGYGSTEALGVMRNGIIQRPPVIDYKLVDVPELGYR TTDKPYPRGELCIRSTSLISGYYKRPEITAEVFDAQGYYKTGDVMAEIAPDHLVYVDRSK NVLKLSQGEFVAVAKLEAAYGTSPYVKQIFVYGNSERSFLLAVVVPNAEVLGARDQEEAK PLIAASLQKIAKEAGLQSYEVPRDFLIETEPFTTQNGLLSEVGKLLRPKLKARYGEALEA RYDEIAHGQADELRALRDGAGQRPVVETVVRAAVAISGSEGAEVGPEANFADLGGDSLSA LSLANLLHDVFEVEVPVRIIIGPTASLAGIAKHIEAERAGASAPTAASVHGAGATRIRAS ELTLEKFLPEDLLAAAKGLPAADQVRTVLLTGANGWLGRFLALEQLERLARSGQDGGKLI CLVRGKDAAAARRRIEETLGTDPALAARFAELAEGRLEVVPGDVGEPKFGLDDAAWDRLA EEVDVIVHPAALVNHVLPYHQLFGPNVVGTAEIIRLAITAKRKPVTYLSTVAVAAGVEPS SFEEDGDIRAVVPERPLGDGYANGYGNSKWAGEVLLREAHELVGLPVAVFRSDMILAHTR YTGQLNVPDQFTRLVLSLLATGIAPKSFYQQGAAGERQRAHYDGIPVDFTAEAITTLGAE PSWFDGGAGFRSFDVFNPHHDGVGLDEFVDWLIEAGHPISRIDDHKEWFARFETAVRGLP EAQRQHSLLPLLRAYSFPHPPVDGSVYPTGKFQGAVKAAQVGSDHDVPHLGKALIVKYAD DLKALGLL |
| 5 | Mycobacterium smegmatis | ABK75684.1 | MTIETREDRFNRRIDHLFETDPQFAAARPDEAISAAAADPELRLPAAVKQILAGYADRPA LGKRAVEFVTDEEGRTTAKLLPRFDTITYRQLAGRIQAVTNAWHNHPVNAGDRVAILGFT SVDYTTIDIALLELGAVSVPLQTSAPVAQLQPIVAETEPKVIASSVDFLADAVALVESGP APSRLVVFDYSHEVDDQREAFEAAKGLAGTGVVVETITDALDRGRSLADAPLYVPDEAD PLTLLIYTSGSTGTPKGAMYPESKTATMWQAGSKARWDETLGVMPSITLNFMPMSHVMGR GILCSTLASGGTAYFAARSDLSTFLEDLALVRPTQLNFVPRIWDMLFQEYQSRLDNRRAE GSEDRAEAAVLEEVRTQLLGGRFVSALTGSAPISAEMKSWVEDLLDMHLLEGYGSTEAGA VFIDGQIQRPPVIDYKLVDVPDLGYFATDRPYPRGELLVKSEQMFPGYYKRPEITAEMFD EDGYYRTGDIVAELGPDHLEYLDRRNNVLKLSQGEFVTVSKLEAVFGDSPLVRQIYVYGN SARSYLLAVVVPTEEALSRWDGDELKSRISDSLQDAARAAGLQSYEIPRDFLVETTPFTL ENGLLTGIRKLARPKLKAHYGERLEQLYTDLAEGQANELRELRRNGADRPVVETVSRAAV ALLGASVTDLRSDAHFTDLGGDSLSALSFSNLLHEIFDVDVPVGVIVSPATDLAGVAAYI EGELRGSKRPTYASVHGRDATEVRARDLALGKFIDAKTLSAAPGLPRSGTEIRTVLLTGA TGFLGRYLALEWLERMDLVDGKVICLVRARSDDEARARLDATFDTGDATLLEHYRALAAD HLEVIAGDKGEADLGLDHDTWQRLADTVDLIVDPAALVNHVLPYSQMFGPNALGTAELIR IALTTTIKPYVYVSTIGVGQGISPEAFVEDADIREISATRRVDDSYANGYGNSKWAGEVL LREAHDWCGLPVSVFRCDMILADTTYSGQLNLPDMFTRLMLSLVATGIAPGSFYELDADG NRQRAHYDGLPVEFIAEAISTIGSQVTDGFETFHVMNPYDDGIGLDEYVDWLIEAGYPVH RVDDYATWLSRFETALRALPERQRQASLLPLLHNYQQPSPPVCGAMAPTDRFRAAVQDAK IGPDKDIPHVTADVIVKYISNLQMLGLL |
| 6 | Mycobacterium massiliense | EIV11143.1 | MTNETNPQQEQLSRRIESLRESDPQFRAAQPDPAVAEQVLRPGLHLSEAIAALMTGYAER PALGERARELVIDQDGRTTLRLLPRFDTTTYGELWSRTTSVAAAWHHDATHPVKAGDLVA TLGFTSIDYTVLDLAIMILGGVAVPLQTSAPASQWTTILAEAEPNTLAVSIELIGAAMES VRATPSIKQVVVFDYTPEVDDQREAFEAASTQLAGTGIALETLDAVIARGAALPAAPLYA PSAGDDPLALLIYTSGSTGAPKGAMHSENIVRRWWIREDVMAGTENLPMIGLNFMPMSHI MGRGTLTSTLSTGGTGYFAASSDMSTLFEDMELIRPTALALVPRVCDMVFQRFQTEVDRR LASGDTASAEAVAAEVKADIRDNLFGGRVSAMVGSAPLSEELGEFIESCFELNLTDGYG STEAGMVFRDGIVQRPPVIDYKLVDVPELGYFSTDKPHPRGELLLKTDGMFLGYYKRPEV TASVFDADGFYMTGDIVAELAHDNIEIIDRRNNVLKLSQGEFVAVATLEAEYANSPVVHQ IYVYGSSERSYLLAVVVPTPEAVAAAKGDAAALKTTIADSLQDIAKEIQLQSYEVPRDFI IEPQPFTQGNGLLTGIAKLARPNLKAHYGPRLEQMYAEIAEQQAAELRALHGVDPDKPAL ETVLAKAAQALLGVSSAELAADAHFTDLGGDSLSALSFSDLLRDIFAVEVPVGVIVSAAND LGGVAKFVDEQRHSGGTRPTAEATLHGAGHTEIRAADLTLDKFIDEATLHAAPSLPKAAGI PHTVLLTGSNGYLGHYLALEWLERLDKTDGKLIVIVRGKNAEAAYGRLEEAFDTGDTELL AHFRSLADKHLEVLAGDIGDPNLGLDADTWQRLADTVDVIVHPAALVNHVLPYNQLFGPN VVGTAEIIKLAITTKIKPVTYLSTVAVAAYVDPTTFDEESDIRLISAVRPIDDGYANGYG NAKWAGEVLLREAHDLCGLPVAVFRSDMILAHSRYTGQLNVPDQFTRLILSLIATGIAPG SFYQAQTTGERPLAHYDGLPGDFTAEAITTLGTQVPEGSEGFVTYDCVNPHADGISLDNF VDWLIEAGYPIARIDNYTEWFTRFDTAIRGLSEKQKQHSLLPLLHAFEQPSAAENHGVVP AKRFQHAVQAAGIGPVGQDGTTDIPHLSRRLIVKYAKDLEQLGLL |

FIG. 9B

| SEQ ID NO | Organism | GENBANK reference | Amino acid sequence |
|---|---|---|---|
| 7 | Segniliparus rotundus | ADG98140.1 | MTQSHTQGPQASAAHSRLARRAAELLATDPQAAATLPDPEVVRQATRPGLRLAERVDAIL SGYADRPALGQRSFQTVKDPITGRSSVELLPTFDTITYRELRERATAIASDLAHHPQAPA KPGDFLASIGFISVDYVAIDIAGVFAGLTAVPLQTGATLATLTAITAETAPTLFAASIEH LPTAVDAVLATPSVRRLLVFDYRAGSDEDREAVEAAKRKIADAGSSVLVDVLDEVIARGK SAPKAPLPPATDAGDDSLSLLIYTSGSTGTPKGAMYPERNVAHFWGGVWAAAFDEDAAPP VPAINITFLPLSHVASRLSLMPTLARGGLMHFVAKSDLSTLFEDLKLARPTNLFLVPRVV EMLYQHYQSELDRRGVQDGTREAEAVKDDLRTGLLGGRILTAGFGSAPLSAELAGFIESL LQIHLVDGYGSTEAGPVWRDGYLVKPPVTDYKLIDVPELGYFSTDSPHPRGELAIKTQTI LPGYYKRPETTAEVFDEDGFYLTGDVVAQIGPEQFAYVDRRKNVLKLSQGEFVTLAKLEA AYSSSPLVRQLFVYGSSERSYLLAVIVPTPDALKKFGVGEAAKAALGESLQKIARDEGLQ SYEVPRDFIIETDPFTVENGLLSDARKSLRPKLKEHYGERLEAMYKELADGQANELRDIR RGVQQRPTLETVRRAAAAMLGASAAEIKPDAHFTDLGGDSLSALTFSNFLHDLFEVDVPV GVIVSAANTLGSVAEHIDAQLAGGRARPTFATVHGKGSTTIKASDLTLDKFIDEQTLEAA KHLPKPADPPRTVLLTGANGWLGRFLALEWLERLAPAGGKLITIVRGKDAAQAKARLDAA YESGDPKLAGHYQDLAATTLEVLAGDFSEPRLGLDEATWNRLADEVDFISHPGALVNHVL PYNQLFGPNVAGVAEIIKLAITTRIKPVTYLSTVAVAAGVEPSALDEDGDIRTVSAERSV DEGYANGYGNSKWGGEVLLREAHDRTGLPVRVFRSDMILAHQKYTGQVNATDQFTRLVQS LLATGLAPKSFYELDAQGNRQRAHYDGIPVDFTAESITTLGGDGLEGYRSYNVFNPHRDG VGLDEFVDWLIEAGHPITRIDDYDQWLSRFETSLRGLPESKRQASVLPLLHAFARPGPAV DGSPFRNTVFRTDVQKAKIGAEHDIPHLGKALVLKYADDIKQLGLL |
| 8 | Chromobacterium violaceum | AAQ59697.1 | MQKQRTTSQWRELDAAHHLHPFTDTASLNQAGARVMTRGEGVYLWDSEGNKIIDGMAGLW CVNVGYGRKDFAEAARRQMEELPFYNTFFKTTHPAVVELSSLLAEVTPAGFDRVFYTNSG SESVDTMIRMVRRYWDVQGKPEKKTLIGRWNGYHGSTIGGASLGGMKYMHEQGDLIPGM AHIEQPWWYKHGKDMTPDEFGVVAARWLEEKILEIGADKVAAFVGEPIQGAGGVIVPPAT YWPEIERICRKYDVLLVADEVICGFGRTGEWFGHQHFGFQPDLFTAAKGLSSGYLPIGAV FVGKRVAEGLIAGGDFNHGFTYSGHPVCAAVAHANVAALRDEGIVQRVKDDIGPYMQKRW RETFSRFEHVDDVRGVGMVQAFTLVKNKAKRELFPDFGEIGTLCRDIFFRNNLIMRACGD HIVSAPPLVMTRAEVDEMLAVAERCLEEFEQTLKARGLA |
| 9 | Pseudomonas aeruginosa | AAG08191.1 | MNARLHATSPLGDADLVRADQAHYMHGYVHVFDDHRVNGSLNIAAGDGAYIYDTAGNRYLD AVGGMWCTNIGLGREEMARTVAEQTRLLAYSNPFCDMANPRAIELCRKLAELAPGDLDHV FLTTGGSTAVDTAIRLMHYYQNCRGKRAKKHVITRINAYHGSTFLGMSLGGKSADRPAEF DFLDERIHHLACPYYYRAPEGLGEAEFLDGLVDEFERKILELGADRVGAFISEPVFGSGG VIVPPAGYHRRMWELCQRYDVLYISDEVVTSFGRLGHFFASQAVFGVQPDIILTAKGLTS GYQPLGACIFSRRIWEVIAEPDKGRCFSHGFTYSGHPVACAAALKNIEIIEREGLLAHAD EVGRYFEERLQSLRDLPIVGDVRGMRFMACVEFVADKASKALFPESLNIGEWVHLRAQKR GLLVRPIVHLNVMSPPLILTREQVDTVVRVLRESIEETVEDLVRAGHR |
| 10 | Pseudomonas syringae | AAY39893.1 | MSANNPQTLEWQALSSEHHLAPFSDYKQLKEKGPRIITRAEGVYLWDSEGNKILDGMSGL WCVAIGYGREELADAASKQMRELPYYNLFFQTAHPPVLELAKAISDIAPEGMNHVFFTGS GSEGNDTMLRMVRHYWALKGQPNKKTIISRVNGYHGSTVAGASLGGMTYMHEQGDLPIPG VVHIPQPYWFGEGGDMTPDEFGIWAAEQLEKKILELGVENVGAFIAEPIQGAGGVIVPPD SYWPKIKEILSRYDILFAADEVICGFGRTSEWFGSDFYGLRPDMMTIAKGLTSGYVPMGG LIVRDEIVAVLNEGGDFNHGFTYSGHPVAAAVALENIRILREEKIVERVRSETAPYLQKR LRELSDHPLVGEVRGVGLLGAIELVKDKTTRERYTDKGAGMICRTFCFDNGLIMRAVGDT MIIAPPLVISFAQIDELVEKARTCLDLTLAVLQG |
| 11 | Rhodobacter sphaeroides | ABA81135.1 | MTRNDATNAAGAVGAAMRDHILLPAQEMAKLGKSAQPVLTHAEGIYVHTEDGRRLIDGPA GMWCAQVGYGRREIVDAMAHQAMVLPYASPWYMATSPAARLAEKIATLTPGDLNRIFFTT GGSTAVDSALRFSEFYNNVLGRPQKKRIIVRYDGYHGSTALTAACTGRTGNWPNFDIAQD RISFLSSPNPRHAGNRSQEAFLDDLVQEFEDRIESLGPDTIAAFLAEPILASGGVIIPPA GYHARFKAICEKHDILYISDEVVTGFGRCGEWFASEKVFGVVPDIITFAKGVTSGYVPLG GLAISEAVLARISGENAKGSWFTNGYTYSNQPVACAAALANIELMEREGIVDQAREMADY FAAALASLRDLPGVAETRSVGLVGCVQCLLDPTRADGTAEDKAFTLKIDERCFELGLIVR PLGDLCVISPPLIISRAQIDEMVAIMRQAITEVSAAHGLTAKEPAAV |
| 12 | Escherichia coli | NP_417544.5 | MNRLPSSASALACSAHALNLIEKRTLDHEEMKALNREVIEYFKEHVNPGFLEYRKSVTAG GDYGAVEWQAGSLNTLVDTQGQEFIDCLGGFGIFNVGHRNPVVVSAVQNQLAKQPLHSQE LLDPLRAMLAKTLAALTPGKLKYSFFCNSGTESVEAALKLAKAYQSPRGKFTFIATSGAF HGKSLGALSATAKSTFRKPFMPLLPGFRHVPFGNIEAMRTALNECKKTGDDVAAVILEPI QGEGGVILPPPGYLTAVRKLCDEFGALMILDEVQTGMGRTGKMFACEHENVQPDILCLAK ALGGGMPIGATIATEEVFSVLFDNPFLHTTTFGGNPLACAAALATINVLLEQNLPAQAE QKGDMLLDGFRQLAREYPDLVQEPRGKGMLMAIEFVDNEIGYNFASEMFRQRVLVAGTLN NAKTIRIEPPLTLTIEQCELVIKAARKALAAMRVSVEEA |

FIG. 9C

| SEQ ID NO | Organism | GENBANK reference | Amino acid sequence |
|---|---|---|---|
| 13 | Vibrio fluvialis | AEA39183.1 | MNKPQSWEARAETYSLYGFTDMPSLHQRGTVVVTHGEGPYIVDVNGRRYLDANSGLWNMV AGFDHKGLIDAAKAQYERFPGYHAFFGRMSDQTVMLSEKLVEVSPFDSGRVFYTNSGSEA NDTMVKMLWFLHAAEGKPQKRKILTRWNAYHGVTAVSASMTGKPYNSVFGLPLPGFVHLT CPHYWRYGEEGETEEQFVARLARELEETIQREGADTIAGFFAEPVMGAGGVIPPAKGYFQ AILPILRKYDIPVISDEVICGFGRTGNTWGCVTYDFTPDAIISSKNLTAGFFPMGAVILG PELSKRLETAIEAIEEFPHGFTASGHPVGCAIALKAIDVVMNEGLAENVRRLAPRFEERL KHIAERPNIGEYRGIGFMWALEAVKDKASKTPFDGNLSVSERIANTCTDLGLICRPLGQS VVLCPPFILTEAQMDEMFDKLEKALDKVFAEVA |
| 14 | Bacillus subtilis | WP_00323 4549.1 | MKIYGIYMDRPLSQEENERFMSFISPEKREKCRRFYHKEDAHRTLLGDVLVRSVISRQYQ LDKSDIRFSTQEYGKPCIPDLPDAHFNISHSGRWVICAFDSQPIGIDIEKTKPISLEIAK RFFSKTEYSDLLAKDKDEQTDYFYHLWSMKESFIKQEGKGLSLPLDSFSVRLHQDGQVSI ELPDSHSPCYIKTYEVDPGYKMAVCAAHPDFPEDITMVSYEELL |
| 15 | Nocardia sp. NRRL 5646 | ABI83656.1 | MIETILPAGVESAELLEYPEDLKAHPAEEHLIAKSVEKRRRDFIGARHCARLALAELGEP PVAIGKGERGAPIWPRGVVGSLTHCDGYRAAAVAHKMRFRSIGIDAEPHATLPEGVLDSV SLPPEREWLKTTDSALHLDRLLFCAKEATYKAWWPLTARWLGFEEAHITFEIEDGSADSG NGTFHSELLVPGQTNDGGTPLLSFDGRWLIADGFILTAIAYA |
| 16 | Bacillus cereus | AAS43086.1 | MINKTLLQKRFNVAAVSYDQYANVQKKMAHSLLSTLNRRYSTNSSIRILELGCGTGYVTE QLSNLFPKAQITAIDFAESMIAVAKTRQNVNNVTFYCEDIERLRLEETYDVIISNATFQW LNDLKQVITNLFRHLSIEGILLFSTFGQETFQELHASFQRAKEEKNIQNETSIGQRFYSK NQLRHICEIETGDVHVSETCYIERFTEVREFLHSIRKVGATNSNEESYCQSPSLFRAMLR IYERDFTGNEGIMATYHALFVHITKEGKR |
| 17 | Escherichia coli | AAC76437.1 | MNNIWWQTKGQGNVHLVLLHGWGLNAEVWRCIDEELSSHFTLHLVDLPGFGRSRGFGALS LADMAEAVLQQAPDKAIWLGWSLGGLVASQIALTHPERVQALVTVASSPCFSARDEWPGI KPDVLAGFQQQLSDDFQRTVERFLALQTMGTETARQDARALKKTVLALPMPEVDVLNGGL EILKTVDLRQPLQNVSMPFLRLYGYLDGLVPRKVVPMLDKLWPHSESYIFAKAAHAPFIS HPAEFCHLLVALKQRV |
| 18 | Bacillus subtilis | AAB17457.1 | MMQEETFYSVRMRASMNGSHEDGGKHISGGERLIPFHEMKHTVNALLEKGLSHSRGKPDFM QIQFEEVHESIKTIQPLPVHTNEVSCPEEGQKLARLLLEKEGVSRDVIEKAYEQIPEWSDVRGA VLFDIHTGKRMDQTKEKGVRVSRMDWPDANFEKWALHSHVPAHSRIKEALALASKVSRHPA VVAELCWSDDPDYITGYVAGKKMGYQRITAMKEYGTEEGCRVFFIDGSNDVNTYIHDLEKQPI LIEWEEDHDS |
| 19 | Bacillus subtilis | AAB17459.1 | MKIDSWLNERLDRMKEAGVHRNLRSMDGAPVPERNIDGENQTVWSSNNYLGLASDRRLIDA AQTALQQFGTGSSGSRLTTGNSVVHEKLEKKIASFKLTEAALLFSSGYLANVGVLSSLPEKED VILSDQLNHASMIDGCRLSKADTVVYRHIDMNDLENKLNETQRYQRRFIVTDGVFSMDGTIAP LDQIISLAKRYHAFVVVDDAHATGVLGDSGQGTSEYFGVCPDIVIGTLSKAVGAEGGFAAGSA VFIDFLLNHARTFIFQTAIPPASCAAAHEAFNIIEASREKRQLLFSYISMIRTSLKNMGYVVKGDH TPIIPVVIGDAHKTVLFAEKLQGKGIYAPAIRPPTVAPGESRIRITITSDHSMGDIDHLLQTFHSIG KELHII |
| 20 | Escherichia coli | NP_415298.1 | MATVNKQAIAAAFGRAAAHYEQHADLQRQSADALLAMLPQRKYTHVLDAGCGPGWMSRHW RERHAQVTALDLSPPMLVQARQKDAADHYLAGDIESLPLATATFDLAWSNLAVQWCGNLSTA LRELYRVVRPKGVVAFTTLVQGSLPELHQAWQAVDERPHANRFLPPDEIEQSLNGVHYQHHI QPITLWFDDALSAMRSLKGIGATHLHEGRDPRILTRSQLQRLQLAWPQQGRYPLTYHLFLG VIARE |
| 21 | Lactobacillus brevis | ABJ63754.1 | MAANEFSETHRVVYYEADDTGQLTLAMLINLFVLVSEDQNDALGLSTAFV QSHGVGWVVTQYHLHIDELPRTGAQVTIKTRATAYNRYFAYREYWLLDDA GQVLAYGEGIWVHTMSYATRKITTIPAEVMAPYHSEEQTRLPRLPRPDHFD EAVNQTLKPYTVRYFDIDGNGHVNNAHYFDWMLDVLPATFLRAHHPTDVK IRFENEVQYGHQVTSELSQAAALTTQHMIKVGDLTAVKATIQWDNR |
| 22 | Lactobacillus plantarum | CCC78182.1 | MATLGANASLYSEQHRITYYECDRTGRATLTTLIDIAVLASEDQSDALGL TTEMVQSHGVGWVVTQYAIDITRMPRQDEVVTIAVRGSAYNPYFAYREFW IRDADGQQLAYITSIWVMMSQTTRRIVKILPELVAPYQSEVVKRIPRLPR PISFEATDTTITKPYHVRFFDIDPNRHVNNAHYFDWLVDTLPATFLLQHD LVHVDVRYENEVKYGQTVTAHANILPSEVADQVTTSHLIEVDDEKCCEVT IQWRTLPEPIQ |
| 23 | Escherichia coli | AAA23516.1 | MSWQEKINAALDARRAADALRRRYPVAQGAGRWLVADDRQYLNFSSNDYLGLSHHPQIIRA WQQGAEQFGIGSGGSGHVSGYSVVHQALEEELAEWLGYSRALLFISGFAANQAVIAAMMAK EDRIAADRLSHASLLEAASLSPSQLRRFAHNDVTHLARLLASPCPGQQMVVTEGVFSMDGDS APLAEIQQVTQQHNGWLMVDDAHGTGVIGEQGRGSCWLQKVKPELLVVTFGKGFGVSGAA VLCSSTVADYLLQFARHLIYSTSMPPAQAQALRASLAVIRSDEGDARREKLAALITRFRAGVQD LPFTLADSCSAIQPLIVGDNSRALQLAEKLRQQGCWVTAIRPPTVPAGTARLRLTLTAAHEMQ DIDRLLEVLHGNG |

FIG. 9D

| Sample ID | Analyte | Mwt [g/mol] | Peak Retention Time [min] | Peak Area @ 260nm [mAu] | Observed Mass (m/z) Negative Mode (M-H) | Observed Mass (m/z) Positive Mode (M+H) | Comments |
|---|---|---|---|---|---|---|---|
| Reference Standard | pimeloyl-CoA methyl ester | 923 | 6.161 | 31172.1 | 922 | 924 | |
| Biotransformation at 1 [h] time point #1 | pimeloyl-CoA methyl ester | 923 | nd | nd | nd | nd | No substrate detected after 1 [h] |
| | pimeloyl-CoA | 910 | 5.577 | 3956.1 | 908 | 910 | |
| Biotransformation at 1 [h] time point #2 | pimeloyl-CoA methyl ester | 923 | nd | nd | nd | nd | No substrate detected after 1 [h] |
| | pimeloyl-CoA | 910 | 5.579 | 3974.1 | 908 | 910 | |
| Biotransformation at 1 [h] time point #3 | pimeloyl-CoA methyl ester | 923 | nd | nd | nd | nd | No substrate detected after 1 [h] |
| | pimeloyl-CoA | 910 | 5.577 | 4093.3 | 908 | 910 | |
| Substrate only control (no enzyme) at 1 [h] time point | pimeloyl-CoA methyl ester | 923 | 6.333 | 4577.9 | 922 | 924 | No product detected after 1 [h] |
| | pimeloyl-CoA | 910 | nd | nd | nd | nd | |

FIG. 21

SEQUENCE LISTING

```
<160> NUMBER OF SEQ ID NOS: 24

<210> SEQ ID NO 1
<211> LENGTH: 286
<212> TYPE: PRT
<213> ORGANISM: Escherichia coli

<400> SEQUENCE: 1

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95
```

Asn Gly Lys Pro Ile Phe Tyr Met Thr Ala Ser Phe Gln Ala Pro Glu
100 105 110

Ala Gly Phe Glu His Gln Lys Thr Met Pro Ser Ala Pro Ala Pro Asp
115 120 125

Gly Leu Pro Ser Glu Thr Gln Ile Ala Gln Ser Leu Ala His Leu Leu
130 135 140

Pro Pro Val Leu Lys Asp Lys Phe Ile Cys Asp Arg Pro Leu Glu Val
145 150 155 160

Arg Pro Val Glu Phe His Asn Pro Leu Lys Gly His Val Ala Glu Pro
165 170 175

His Arg Gln Val Trp Ile Arg Ala Asn Gly Ser Val Pro Asp Asp Leu
180 185 190

Arg Val His Gln Tyr Leu Leu Gly Tyr Ala Ser Asp Leu Asn Phe Leu
195 200 205

Pro Val Ala Leu Gln Pro His Gly Ile Gly Phe Leu Glu Pro Gly Ile
210 215 220

Gln Ile Ala Thr Ile Asp His Ser Met Trp Phe His Arg Pro Phe Asn
225 230 235 240

Leu Asn Glu Trp Leu Leu Tyr Ser Val Glu Ser Thr Ser Ala Ser Ser
245 250 255

Ala Arg Gly Phe Val Arg Gly Glu Phe Tyr Thr Gln Asp Gly Val Leu
260 265 270

Val Ala Ser Thr Val Gln Glu Gly Val Met Arg Asn His Asn
275 280 285

<210> SEQ ID NO 2
<211> LENGTH: 1174
<212> TYPE: PRT
<213> ORGANISM: Mycobacterium marinum

<400> SEQUENCE: 2

Met Ser Pro Ile Thr Arg Glu Glu Arg Leu Glu Arg Arg Ile Gln Asp
1 5 10 15

Leu Tyr Ala Asn Asp Pro Gln Phe Ala Ala Ala Lys Pro Ala Thr Ala
20 25 30

Ile Thr Ala Ala Ile Glu Arg Pro Gly Leu Pro Leu Pro Gln Ile Ile
35 40 45

Glu Thr Val Met Thr Gly Tyr Ala Asp Arg Pro Ala Leu Ala Gln Arg
50 55 60

Ser Val Glu Phe Val Thr Asp Ala Gly Thr Gly His Thr Thr Leu Arg
65 70 75 80

Leu Leu Pro His Phe Glu Thr Ile Ser Tyr Gly Glu Leu Trp Asp Arg
85 90 95

Ile Ser Ala Leu Ala Asp Val Leu Ser Thr Glu Gln Thr Val Lys Pro
100 105 110

Gly Asp Arg Val Cys Leu Leu Gly Phe Asn Ser Val Asp Tyr Ala Thr
115 120 125

Ile Asp Met Thr Leu Ala Arg Leu Gly Ala Val Ala Val Pro Leu Gln
130 135 140

Thr Ser Ala Ala Ile Thr Gln Leu Gln Pro Ile Val Ala Glu Thr Gln
145 150 155 160

Pro Thr Met Ile Ala Ala Ser Val Asp Ala Leu Ala Asp Ala Thr Glu
165 170 175

Leu Ala Leu Ser Gly Gln Thr Ala Thr Arg Val Leu Val Phe Asp His

```
            180                 185                 190
His Arg Gln Val Asp Ala His Arg Ala Ala Val Glu Ser Ala Arg Glu
            195                 200                 205
Arg Leu Ala Gly Ser Ala Val Val Glu Thr Leu Ala Glu Ala Ile Ala
            210                 215                 220
Arg Gly Asp Val Pro Arg Gly Ala Ser Ala Gly Ser Ala Pro Gly Thr
225                 230                 235                 240
Asp Val Ser Asp Asp Ser Leu Ala Leu Leu Ile Tyr Thr Ser Gly Ser
                245                 250                 255
Thr Gly Ala Pro Lys Gly Ala Met Tyr Pro Arg Arg Asn Val Ala Thr
            260                 265                 270
Phe Trp Arg Lys Arg Thr Trp Phe Glu Gly Gly Tyr Glu Pro Ser Ile
            275                 280                 285
Thr Leu Asn Phe Met Pro Met Ser His Val Met Gly Arg Gln Ile Leu
            290                 295                 300
Tyr Gly Thr Leu Cys Asn Gly Gly Thr Ala Tyr Phe Val Ala Lys Ser
305                 310                 315                 320
Asp Leu Ser Thr Leu Phe Glu Asp Leu Ala Leu Val Arg Pro Thr Glu
                325                 330                 335
Leu Thr Phe Val Pro Arg Val Trp Asp Met Val Phe Asp Glu Phe Gln
            340                 345                 350
Ser Glu Val Asp Arg Arg Leu Val Asp Gly Ala Asp Arg Val Ala Leu
            355                 360                 365
Glu Ala Gln Val Lys Ala Glu Ile Arg Asn Asp Val Leu Gly Gly Arg
            370                 375                 380
Tyr Thr Ser Ala Leu Thr Gly Ser Ala Pro Ile Ser Asp Glu Met Lys
385                 390                 395                 400
Ala Trp Val Glu Glu Leu Leu Asp Met His Leu Val Glu Gly Tyr Gly
                405                 410                 415
Ser Thr Glu Ala Gly Met Ile Leu Ile Asp Gly Ala Ile Arg Arg Pro
            420                 425                 430
Ala Val Leu Asp Tyr Lys Leu Val Asp Val Pro Asp Leu Gly Tyr Phe
            435                 440                 445
Leu Thr Asp Arg Pro His Pro Arg Gly Glu Leu Leu Val Lys Thr Asp
            450                 455                 460
Ser Leu Phe Pro Gly Tyr Tyr Gln Arg Ala Glu Val Thr Ala Asp Val
465                 470                 475                 480
Phe Asp Ala Asp Gly Phe Tyr Arg Thr Gly Asp Ile Met Ala Glu Val
                485                 490                 495
Gly Pro Glu Gln Phe Val Tyr Leu Asp Arg Arg Asn Asn Val Leu Lys
            500                 505                 510
Leu Ser Gln Gly Glu Phe Val Thr Val Ser Lys Leu Glu Ala Val Phe
            515                 520                 525
Gly Asp Ser Pro Leu Val Arg Gln Ile Tyr Ile Tyr Gly Asn Ser Ala
            530                 535                 540
Arg Ala Tyr Leu Leu Ala Val Ile Val Pro Thr Gln Glu Ala Leu Asp
545                 550                 555                 560
Ala Val Pro Val Glu Glu Leu Lys Ala Arg Leu Gly Asp Ser Leu Gln
                565                 570                 575
Glu Val Ala Lys Ala Ala Gly Leu Gln Ser Tyr Glu Ile Pro Arg Asp
            580                 585                 590
Phe Ile Ile Glu Thr Thr Pro Trp Thr Leu Glu Asn Gly Leu Leu Thr
            595                 600                 605
```

Gly Ile Arg Lys Leu Ala Arg Pro Gln Leu Lys Lys His Tyr Gly Glu
    610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Ala Leu Leu Gly Gly Ser Ala Ser Asp Val
                660                 665                 670

Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
                740                 745                 750

Asp Leu Ser Leu Asp Lys Phe Ile Asp Ala Ala Thr Leu Ala Glu Ala
            755                 760                 765

Pro Arg Leu Pro Ala Ala Asn Thr Gln Val Arg Thr Val Leu Leu Thr
770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
                820                 825                 830

Asp Pro Glu Leu Leu Ala His Tyr Arg Ala Leu Ala Gly Asp His Leu
            835                 840                 845

Glu Val Leu Ala Gly Asp Lys Gly Glu Ala Asp Leu Gly Leu Asp Arg
850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
                900                 905                 910

Ile Lys Pro Tyr Ser Tyr Thr Ser Thr Ile Gly Val Ala Asp Gln Ile
            915                 920                 925

Pro Pro Ser Ala Phe Thr Glu Asp Ala Asp Ile Arg Val Ile Ser Ala
930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp Met Phe Thr Arg Met Ile Leu Ser
            995                 1000                1005

Leu Ala Ala Thr Gly Ile Ala Pro Gly Ser Phe Tyr Glu Leu Ala
    1010            1015                1020

```
Ala Asp Gly Ala Arg Gln Arg Ala His Tyr Asp Gly Leu Pro Val
    1025                1030                1035

Glu Phe Ile Ala Glu Ala Ile Ser Thr Leu Gly Ala Gln Ser Gln
    1040                1045                1050

Asp Gly Phe His Thr Tyr His Val Met Asn Pro Tyr Asp Asp Gly
    1055                1060                1065

Ile Gly Leu Asp Glu Phe Val Asp Trp Leu Asn Glu Ser Gly Cys
    1070                1075                1080

Pro Ile Gln Arg Ile Ala Asp Tyr Gly Asp Trp Leu Gln Arg Phe
    1085                1090                1095

Glu Thr Ala Leu Arg Ala Leu Pro Asp Arg Gln Arg His Ser Ser
    1100                1105                1110

Leu Leu Pro Leu Leu His Asn Tyr Arg Gln Pro Glu Arg Pro Val
    1115                1120                1125

Arg Gly Ser Ile Ala Pro Thr Asp Arg Phe Arg Ala Ala Val Gln
    1130                1135                1140

Glu Ala Lys Ile Gly Pro Asp Lys Asp Ile Pro His Val Gly Ala
    1145                1150                1155

Pro Ile Ile Val Lys Tyr Val Ser Asp Leu Arg Leu Leu Gly Leu
    1160                1165                1170

Leu

<210> SEQ ID NO 3
<211> LENGTH: 1173
<212> TYPE: PRT
<213> ORGANISM: Mycobacterium smegmatis

<400> SEQUENCE: 3

Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205
```

```
Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
                260                 265                 270

Ala Met Tyr Thr Glu Ala Met Val Ala Arg Leu Trp Thr Met Ser Phe
            275                 280                 285

Ile Thr Gly Asp Pro Thr Pro Val Ile Asn Val Asn Phe Met Pro Leu
290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
                340                 345                 350

Ala Asp Met Leu Tyr Gln His His Leu Ala Thr Val Asp Arg Leu Val
            355                 360                 365

Thr Gln Gly Ala Asp Glu Leu Thr Ala Glu Lys Gln Ala Gly Ala Glu
370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
                420                 425                 430

Thr Arg Asp Gly Val Ile Val Arg Pro Pro Val Ile Asp Tyr Lys Leu
            435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
                500                 505                 510

Val Asp Arg Arg Asn Asn Val Leu Lys Leu Ala Gln Gly Glu Phe Val
            515                 520                 525

Ala Val Ala Asn Leu Glu Ala Val Phe Ser Gly Ala Ala Leu Val Arg
530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
                580                 585                 590

Leu Gln Ser Tyr Glu Val Pro Ala Asp Phe Ile Val Glu Thr Glu Pro
            595                 600                 605

Phe Ser Ala Ala Asn Gly Leu Leu Ser Gly Val Gly Lys Leu Leu Arg
610                 615                 620

Pro Asn Leu Lys Asp Arg Tyr Gly Gln Arg Leu Glu Gln Met Tyr Ala
```

-continued

```
            625                 630                 635                 640
        Asp Ile Ala Ala Thr Gln Ala Asn Gln Leu Arg Glu Leu Arg Arg Ala
                        645                 650                 655

Ala Ala Thr Gln Pro Val Ile Asp Thr Leu Thr Gln Ala Ala Ala Thr
                        660                 665                 670

Ile Leu Gly Thr Gly Ser Glu Val Ala Ser Asp Ala His Phe Thr Asp
                        675                 680                 685

Leu Gly Gly Asp Ser Leu Ser Ala Leu Thr Leu Ser Asn Leu Leu Ser
                        690                 695                 700

Asp Phe Phe Gly Phe Glu Val Pro Val Gly Thr Ile Val Asn Pro Ala
        705                 710                 715                 720

Thr Asn Leu Ala Gln Leu Ala Gln His Ile Glu Ala Gln Arg Thr Ala
                        725                 730                 735

Gly Asp Arg Arg Pro Ser Phe Thr Thr Val His Gly Ala Asp Ala Thr
                        740                 745                 750

Glu Ile Arg Ala Ser Glu Leu Thr Leu Asp Lys Phe Ile Asp Ala Glu
                        755                 760                 765

Thr Leu Arg Ala Ala Pro Gly Leu Pro Lys Val Thr Thr Glu Pro Arg
                        770                 775                 780

Thr Val Leu Leu Ser Gly Ala Asn Gly Trp Leu Gly Arg Phe Leu Thr
        785                 790                 795                 800

Leu Gln Trp Leu Glu Arg Leu Ala Pro Val Gly Gly Thr Leu Ile Thr
                        805                 810                 815

Ile Val Arg Gly Arg Asp Asp Ala Ala Ala Arg Ala Arg Leu Thr Gln
                        820                 825                 830

Ala Tyr Asp Thr Asp Pro Glu Leu Ser Arg Arg Phe Ala Glu Leu Ala
                        835                 840                 845

Asp Arg His Leu Arg Val Val Ala Gly Asp Ile Gly Asp Pro Asn Leu
                        850                 855                 860

Gly Leu Thr Pro Glu Ile Trp His Arg Leu Ala Ala Glu Val Asp Leu
        865                 870                 875                 880

Val Val His Pro Ala Ala Leu Val Asn His Val Leu Pro Tyr Arg Gln
                        885                 890                 895

Leu Phe Gly Pro Asn Val Val Gly Thr Ala Glu Val Ile Lys Leu Ala
                        900                 905                 910

Leu Thr Glu Arg Ile Lys Pro Val Thr Tyr Leu Ser Thr Val Ser Val
                        915                 920                 925

Ala Met Gly Ile Pro Asp Phe Glu Glu Asp Gly Asp Ile Arg Thr Val
                        930                 935                 940

Ser Pro Val Arg Pro Leu Asp Gly Gly Tyr Ala Asn Gly Tyr Gly Asn
        945                 950                 955                 960

Ser Lys Trp Ala Gly Glu Val Leu Leu Arg Glu Ala His Asp Leu Cys
                        965                 970                 975

Gly Leu Pro Val Ala Thr Phe Arg Ser Asp Met Ile Leu Ala His Pro
                        980                 985                 990

Arg Tyr Arg Gly Gln Val Asn Val Pro Asp Met Phe Thr Arg Leu Leu
                        995                1000                1005

Leu Ser Leu Leu Ile Thr Gly Val Ala Pro Arg Ser Phe Tyr Ile
                       1010                1015                1020

Gly Asp Gly Glu Arg Pro Arg Ala His Tyr Pro Gly Leu Thr Val
                       1025                1030                1035

Asp Phe Val Ala Glu Ala Val Thr Thr Leu Gly Ala Gln Gln Arg
                       1040                1045                1050
```

```
Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
1070                1075                1080

Pro Ile Asp Arg Val Asp Asp Tyr Asp Asp Trp Val Arg Arg Phe
    1085                1090                1095

Glu Thr Ala Leu Thr Ala Leu Pro Glu Lys Arg Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170

<210> SEQ ID NO 4
<211> LENGTH: 1148
<212> TYPE: PRT
<213> ORGANISM: Segniliparus rugosus

<400> SEQUENCE: 4

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
            35                  40                  45

Leu Asp Thr Leu Met Arg Gly Tyr Ala Glu Arg Pro Ala Leu Ala His
        50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Ala Trp Gln Ala Asp Gly Leu Ala Pro
                85                  90                  95

Gly Asp Phe Val Ala Thr Val Gly Phe Thr Ser Pro Asp Tyr Val Ala
            100                 105                 110

Val Asp Leu Ala Ala Ala Arg Ser Gly Leu Val Ser Val Pro Leu Gln
        115                 120                 125

Ala Gly Ala Ser Leu Ala Gln Leu Val Gly Ile Leu Glu Glu Thr Glu
    130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Glu Gln Leu Ala Arg Ala Gly Arg Ala Val Val
        195                 200                 205

Val Glu Thr Leu Ala Asp Leu Ala Ala Arg Gly Glu Ala Leu Pro Glu
    210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
```

-continued

```
                245                 250                 255
Gln Arg Leu Val Ser Gln Leu Trp Gly Arg Thr Pro Val Pro Gly
                260                 265                 270
Met Pro Asn Ile Ser Leu His Tyr Met Pro Leu Ser His Ser Tyr Gly
                275                 280                 285
Arg Ala Val Leu Ala Gly Ala Leu Ser Ala Gly Gly Thr Ala His Phe
                290                 295                 300
Thr Ala Asn Ser Asp Leu Ser Thr Leu Phe Glu Asp Ile Ala Leu Ala
305                 310                 315                 320
Arg Pro Thr Phe Leu Ala Leu Val Pro Arg Val Cys Glu Met Leu Phe
                325                 330                 335
Gln Glu Ser Gln Arg Gly Gln Asp Val Ala Glu Leu Arg Glu Arg Val
                340                 345                 350
Leu Gly Gly Arg Leu Leu Val Ala Val Cys Gly Ser Ala Pro Leu Ser
                355                 360                 365
Pro Glu Met Arg Ala Phe Met Glu Glu Val Leu Gly Phe Pro Leu Leu
                370                 375                 380
Asp Gly Tyr Gly Ser Thr Glu Ala Leu Gly Val Met Arg Asn Gly Ile
385                 390                 395                 400
Ile Gln Arg Pro Pro Val Ile Asp Tyr Lys Leu Val Asp Val Pro Glu
                405                 410                 415
Leu Gly Tyr Arg Thr Thr Asp Lys Pro Tyr Pro Arg Gly Glu Leu Cys
                420                 425                 430
Ile Arg Ser Thr Ser Leu Ile Ser Gly Tyr Tyr Lys Arg Pro Glu Ile
                435                 440                 445
Thr Ala Glu Val Phe Asp Ala Gln Gly Tyr Tyr Lys Thr Gly Asp Val
                450                 455                 460
Met Ala Glu Ile Ala Pro Asp His Leu Val Tyr Val Asp Arg Ser Lys
465                 470                 475                 480
Asn Val Leu Lys Leu Ser Gln Gly Glu Phe Val Ala Val Ala Lys Leu
                485                 490                 495
Glu Ala Ala Tyr Gly Thr Ser Pro Tyr Val Lys Gln Ile Phe Val Tyr
                500                 505                 510
Gly Asn Ser Glu Arg Ser Phe Leu Leu Ala Val Val Pro Asn Ala
                515                 520                 525
Glu Val Leu Gly Ala Arg Asp Gln Glu Glu Ala Lys Pro Leu Ile Ala
                530                 535                 540
Ala Ser Leu Gln Lys Ile Ala Lys Glu Ala Gly Leu Gln Ser Tyr Glu
545                 550                 555                 560
Val Pro Arg Asp Phe Leu Ile Glu Thr Glu Pro Phe Thr Thr Gln Asn
                565                 570                 575
Gly Leu Leu Ser Glu Val Gly Lys Leu Leu Arg Pro Lys Leu Lys Ala
                580                 585                 590
Arg Tyr Gly Glu Ala Leu Glu Ala Arg Tyr Asp Glu Ile Ala His Gly
                595                 600                 605
Gln Ala Asp Glu Leu Arg Ala Leu Arg Asp Gly Ala Gly Gln Arg Pro
                610                 615                 620
Val Val Glu Thr Val Val Arg Ala Ala Val Ala Ile Ser Gly Ser Glu
625                 630                 635                 640
Gly Ala Glu Val Gly Pro Glu Ala Asn Phe Ala Asp Leu Gly Gly Asp
                645                 650                 655
Ser Leu Ser Ala Leu Ser Leu Ala Asn Leu Leu His Asp Val Phe Glu
                660                 665                 670
```

```
Val Glu Val Pro Val Arg Ile Ile Gly Pro Thr Ala Ser Leu Ala
        675                 680                 685

Gly Ile Ala Lys His Ile Glu Ala Glu Arg Ala Gly Ala Ser Ala Pro
    690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Leu Ala Ala Ala
                725                 730                 735

Lys Gly Leu Pro Ala Ala Asp Gln Val Arg Thr Val Leu Leu Thr Gly
            740                 745                 750

Ala Asn Gly Trp Leu Gly Arg Phe Leu Ala Leu Glu Gln Leu Glu Arg
        755                 760                 765

Leu Ala Arg Ser Gly Gln Asp Gly Gly Lys Leu Ile Cys Leu Val Arg
    770                 775                 780

Gly Lys Asp Ala Ala Ala Arg Arg Arg Ile Glu Glu Thr Leu Gly
785                 790                 795                 800

Thr Asp Pro Ala Leu Ala Ala Arg Phe Ala Glu Leu Ala Glu Gly Arg
                805                 810                 815

Leu Glu Val Val Pro Gly Asp Val Gly Glu Pro Lys Phe Gly Leu Asp
            820                 825                 830

Asp Ala Ala Trp Asp Arg Leu Ala Glu Glu Val Asp Val Ile Val His
        835                 840                 845

Pro Ala Ala Leu Val Asn His Val Leu Pro Tyr His Gln Leu Phe Gly
    850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
                885                 890                 895

Val Glu Pro Ser Ser Phe Glu Glu Asp Gly Asp Ile Arg Ala Val Val
            900                 905                 910

Pro Glu Arg Pro Leu Gly Asp Gly Tyr Ala Asn Gly Tyr Gly Asn Ser
        915                 920                 925

Lys Trp Ala Gly Glu Val Leu Leu Arg Glu Ala His Glu Leu Val Gly
    930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
        995                 1000                1005

Phe Thr Ala Glu Ala Ile Thr Thr Leu Gly Ala Glu Pro Ser Trp
    1010                1015                1020

Phe Asp Gly Gly Ala Gly Phe Arg Ser Phe Asp Val Phe Asn Pro
    1025                1030                1035

His His Asp Gly Val Gly Leu Asp Glu Phe Val Asp Trp Leu Ile
    1040                1045                1050

Glu Ala Gly His Pro Ile Ser Arg Ile Asp Asp His Lys Glu Trp
    1055                1060                1065

Phe Ala Arg Phe Glu Thr Ala Val Arg Gly Leu Pro Glu Ala Gln
    1070                1075                1080
```

```
Arg Gln His Ser Leu Leu Pro Leu Leu Arg Ala Tyr Ser Phe Pro
    1085                1090                1095

His Pro Pro Val Asp Gly Ser Val Tyr Pro Thr Gly Lys Phe Gln
    1100                1105                1110

Gly Ala Val Lys Ala Ala Gln Val Gly Ser Asp His Asp Val Pro
    1115                1120                1125

His Leu Gly Lys Ala Leu Ile Val Lys Tyr Ala Asp Asp Leu Lys
    1130                1135                1140

Ala Leu Gly Leu Leu
    1145

<210> SEQ ID NO 5
<211> LENGTH: 1168
<212> TYPE: PRT
<213> ORGANISM: Mycobacterium smegmatis

<400> SEQUENCE: 5

Met Thr Ile Glu Thr Arg Glu Asp Arg Phe Asn Arg Ile Asp His
1               5                   10                  15

Leu Phe Glu Thr Asp Pro Gln Phe Ala Ala Arg Pro Asp Glu Ala
                20                  25                  30

Ile Ser Ala Ala Ala Asp Pro Glu Leu Arg Leu Pro Ala Ala Val
                35                  40                  45

Lys Gln Ile Leu Ala Gly Tyr Ala Asp Arg Pro Ala Leu Gly Lys Arg
    50                  55                  60

Ala Val Glu Phe Val Thr Asp Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
                    100                 105                 110

Arg Val Ala Ile Leu Gly Phe Thr Ser Val Asp Tyr Thr Thr Ile Asp
                115                 120                 125

Ile Ala Leu Leu Glu Leu Gly Ala Val Ser Val Pro Leu Gln Thr Ser
    130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                    165                 170                 175

Glu Ser Gly Pro Ala Pro Ser Arg Leu Val Val Phe Asp Tyr Ser His
                180                 185                 190

Glu Val Asp Asp Gln Arg Glu Ala Phe Glu Ala Ala Lys Gly Lys Leu
                195                 200                 205

Ala Gly Thr Gly Val Val Glu Thr Ile Thr Asp Ala Leu Asp Arg
    210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                        245                 250                 255

Gly Ala Met Tyr Pro Glu Ser Lys Thr Ala Thr Met Trp Gln Ala Gly
                260                 265                 270

Ser Lys Ala Arg Trp Asp Glu Thr Leu Gly Val Met Pro Ser Ile Thr
        275                 280                 285

Leu Asn Phe Met Pro Met Ser His Val Met Gly Arg Gly Ile Leu Cys
    290                 295                 300
```

-continued

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
            325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
            355                 360                 365

Ala Val Leu Glu Glu Val Arg Thr Gln Leu Leu Gly Arg Phe Val
370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
            405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
            435                 440                 445

Asp Arg Pro Tyr Pro Arg Gly Glu Leu Leu Val Lys Ser Glu Gln Met
450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
            485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
            515                 520                 525

Ser Pro Leu Val Arg Gln Ile Tyr Val Tyr Gly Asn Ser Ala Arg Ser
530                 535                 540

Tyr Leu Leu Ala Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
            565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
            595                 600                 605

Arg Lys Leu Ala Arg Pro Lys Leu Lys Ala His Tyr Gly Glu Arg Leu
            610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
            645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
            675                 680                 685

Phe Ser Asn Leu Leu His Glu Ile Phe Asp Val Asp Val Pro Val Gly
            690                 695                 700

Val Ile Val Ser Pro Ala Thr Asp Leu Ala Gly Val Ala Ala Tyr Ile
705                 710                 715                 720

-continued

```
Glu Gly Glu Leu Arg Gly Ser Lys Arg Pro Thr Tyr Ala Ser Val His
            725                 730                 735

Gly Arg Asp Ala Thr Glu Val Arg Ala Arg Asp Leu Ala Leu Gly Lys
        740                 745                 750

Phe Ile Asp Ala Lys Thr Leu Ser Ala Ala Pro Gly Leu Pro Arg Ser
        755                 760                 765

Gly Thr Glu Ile Arg Thr Val Leu Leu Thr Gly Ala Thr Gly Phe Leu
        770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
                805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
        835                 840                 845

Lys Gly Glu Ala Asp Leu Gly Leu Asp His Asp Thr Trp Gln Arg Leu
    850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
        915                 920                 925

Glu Asp Ala Asp Ile Arg Glu Ile Ser Ala Thr Arg Arg Val Asp Asp
    930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975

Cys Asp Met Ile Leu Ala Asp Thr Thr Tyr Ser Gly Gln Leu Asn Leu
            980                 985                 990

Pro Asp Met Phe Thr Arg Leu Met Leu Ser Leu Val Ala Thr Gly Ile
        995                 1000                1005

Ala Pro Gly Ser Phe Tyr Glu Leu Asp Ala Asp Gly Asn Arg Gln
    1010                1015                1020

Arg Ala His Tyr Asp Gly Leu Pro Val Glu Phe Ile Ala Glu Ala
    1025                1030                1035

Ile Ser Thr Ile Gly Ser Gln Val Thr Asp Gly Phe Glu Thr Phe
    1040                1045                1050

His Val Met Asn Pro Tyr Asp Asp Gly Ile Gly Leu Asp Glu Tyr
    1055                1060                1065

Val Asp Trp Leu Ile Glu Ala Gly Tyr Pro Val His Arg Val Asp
    1070                1075                1080

Asp Tyr Ala Thr Trp Leu Ser Arg Phe Glu Thr Ala Leu Arg Ala
    1085                1090                1095

Leu Pro Glu Arg Gln Arg Gln Ala Ser Leu Leu Pro Leu Leu His
    1100                1105                1110

Asn Tyr Gln Gln Pro Ser Pro Val Cys Gly Ala Met Ala Pro
    1115                1120                1125

Thr Asp Arg Phe Arg Ala Ala Val Gln Asp Ala Lys Ile Gly Pro
```

```
               1130                1135                1140
Asp Lys Asp Ile Pro His Val Thr Ala Asp Val Ile Val Lys Tyr
   1145                1150                1155
Ile Ser Asn Leu Gln Met Leu Gly Leu Leu
   1160                1165

<210> SEQ ID NO 6
<211> LENGTH: 1185
<212> TYPE: PRT
<213> ORGANISM: Mycobacterium massiliense

<400> SEQUENCE: 6

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Gly Val Ala Val
    130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
            180                 185                 190

Phe Asp Tyr Thr Pro Glu Val Asp Asp Gln Arg Glu Ala Phe Glu Ala
        195                 200                 205

Ala Ser Thr Gln Leu Ala Gly Thr Gly Ile Ala Leu Glu Thr Leu Asp
    210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met Tyr Ser Glu Asn Ile Val Arg
            260                 265                 270

Arg Trp Trp Ile Arg Glu Asp Val Met Ala Gly Thr Glu Asn Leu Pro
        275                 280                 285

Met Ile Gly Leu Asn Phe Met Pro Met Ser His Ile Met Gly Arg Gly
    290                 295                 300

Thr Leu Thr Ser Thr Leu Ser Thr Gly Gly Thr Gly Tyr Phe Ala Ala
305                 310                 315                 320

Ser Ser Asp Met Ser Thr Leu Phe Glu Asp Met Glu Leu Ile Arg Pro
                325                 330                 335
```

```
Thr Ala Leu Ala Leu Val Pro Arg Val Cys Asp Met Val Phe Gln Arg
            340                 345                 350

Phe Gln Thr Glu Val Asp Arg Arg Leu Ala Ser Gly Asp Thr Ala Ser
        355                 360                 365

Ala Glu Ala Val Ala Ala Glu Val Lys Ala Asp Ile Arg Asp Asn Leu
    370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
        435                 440                 445

Leu Gly Tyr Phe Ser Thr Asp Lys Pro His Pro Arg Gly Glu Leu Leu
    450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Ile Asp Arg Arg Asn
            500                 505                 510

Asn Val Leu Lys Leu Ser Gln Gly Glu Phe Val Ala Val Ala Thr Leu
        515                 520                 525

Glu Ala Glu Tyr Ala Asn Ser Pro Val Val His Gln Ile Tyr Val Tyr
    530                 535                 540

Gly Ser Ser Glu Arg Ser Tyr Leu Leu Ala Val Val Val Pro Thr Pro
545                 550                 555                 560

Glu Ala Val Ala Ala Lys Gly Asp Ala Ala Leu Lys Thr Thr
                565                 570                 575

Ile Ala Asp Ser Leu Gln Asp Ile Ala Lys Glu Ile Gln Leu Gln Ser
            580                 585                 590

Tyr Glu Val Pro Arg Asp Phe Ile Ile Glu Pro Gln Pro Phe Thr Gln
        595                 600                 605

Gly Asn Gly Leu Leu Thr Gly Ile Ala Lys Leu Ala Arg Pro Asn Leu
    610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
            660                 665                 670

Val Ser Ser Ala Glu Leu Ala Ala Asp Ala His Phe Thr Asp Leu Gly
        675                 680                 685

Gly Asp Ser Leu Ser Ala Leu Ser Phe Ser Asp Leu Leu Arg Asp Ile
    690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
```

-continued

```
            755                 760                 765
    His Ala Ala Pro Ser Leu Pro Lys Ala Ala Gly Ile Pro His Thr Val
    770                 775                 780

Leu Leu Thr Gly Ser Asn Gly Tyr Leu Gly His Tyr Leu Ala Leu Glu
    785                 790                 795                 800

Trp Leu Glu Arg Leu Asp Lys Thr Asp Gly Lys Leu Ile Val Ile Val
                    805                 810                 815

Arg Gly Lys Asn Ala Glu Ala Ala Tyr Gly Arg Leu Glu Glu Ala Phe
                820                 825                 830

Asp Thr Gly Asp Thr Glu Leu Leu Ala His Phe Arg Ser Leu Ala Asp
                835                 840                 845

Lys His Leu Glu Val Leu Ala Gly Asp Ile Gly Asp Pro Asn Leu Gly
    850                 855                 860

Leu Asp Ala Asp Thr Trp Gln Arg Leu Ala Asp Thr Val Asp Val Ile
    865                 870                 875                 880

Val His Pro Ala Ala Leu Val Asn His Val Leu Pro Tyr Asn Gln Leu
                    885                 890                 895

Phe Gly Pro Asn Val Val Gly Thr Ala Glu Ile Ile Lys Leu Ala Ile
                900                 905                 910

Thr Thr Lys Ile Lys Pro Val Thr Tyr Leu Ser Thr Val Ala Val Ala
                915                 920                 925

Ala Tyr Val Asp Pro Thr Thr Phe Asp Glu Glu Ser Asp Ile Arg Leu
    930                 935                 940

Ile Ser Ala Val Arg Pro Ile Asp Asp Gly Tyr Ala Asn Gly Tyr Gly
    945                 950                 955                 960

Asn Ala Lys Trp Ala Gly Glu Val Leu Leu Arg Glu Ala His Asp Leu
                    965                 970                 975

Cys Gly Leu Pro Val Ala Val Phe Arg Ser Asp Met Ile Leu Ala His
                980                 985                 990

Ser Arg Tyr Thr Gly Gln Leu Asn Val Pro Asp Gln Phe Thr Arg Leu
                995                 1000                1005

Ile Leu Ser Leu Ile Ala Thr Gly Ile Ala Pro Gly Ser Phe Tyr
    1010                1015                1020

Gln Ala Gln Thr Thr Gly Glu Arg Pro Leu Ala His Tyr Asp Gly
    1025                1030                1035

Leu Pro Gly Asp Phe Thr Ala Glu Ala Ile Thr Thr Leu Gly Thr
    1040                1045                1050

Gln Val Pro Glu Gly Ser Glu Gly Phe Val Thr Tyr Asp Cys Val
    1055                1060                1065

Asn Pro His Ala Asp Gly Ile Ser Leu Asp Asn Phe Val Asp Trp
    1070                1075                1080

Leu Ile Glu Ala Gly Tyr Pro Ile Ala Arg Ile Asp Asn Tyr Thr
    1085                1090                1095

Glu Trp Phe Thr Arg Phe Asp Thr Ala Ile Arg Gly Leu Ser Glu
    1100                1105                1110

Lys Gln Lys Gln His Ser Leu Leu Pro Leu Leu His Ala Phe Glu
    1115                1120                1125

Gln Pro Ser Ala Ala Glu Asn His Gly Val Val Pro Ala Lys Arg
    1130                1135                1140

Phe Gln His Ala Val Gln Ala Ala Gly Ile Gly Pro Val Gly Gln
    1145                1150                1155

Asp Gly Thr Thr Asp Ile Pro His Leu Ser Arg Arg Leu Ile Val
    1160                1165                1170
```

```
Lys Tyr Ala Lys Asp Leu Glu  Gln Leu Gly Leu Leu
    1175            1180            1185

<210> SEQ ID NO 7
<211> LENGTH: 1186
<212> TYPE: PRT
<213> ORGANISM: Segniliparus rotundus

<400> SEQUENCE: 7

Met Thr Gln Ser His Thr Gln Gly Pro Gln Ala Ser Ala His Ser
1               5                   10                  15

Arg Leu Ala Arg Arg Ala Ala Glu Leu Leu Ala Thr Asp Pro Gln Ala
                20                  25                  30

Ala Ala Thr Leu Pro Asp Pro Glu Val Val Arg Gln Ala Thr Arg Pro
            35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
    210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Ala Phe Asp Glu Asp Ala Ala Pro Val Pro Ala Ile
    290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
            340                 345                 350

Leu Phe Leu Val Pro Arg Val Val Glu Met Leu Tyr Gln His Tyr Gln
```

```
                355                 360                 365
Ser Glu Leu Asp Arg Arg Gly Val Gln Asp Gly Thr Arg Glu Ala Glu
    370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
            420                 425                 430

Glu Ala Gly Pro Val Trp Arg Asp Gly Tyr Leu Val Lys Pro Pro Val
        435                 440                 445

Thr Asp Tyr Lys Leu Ile Asp Val Pro Glu Leu Gly Tyr Phe Ser Thr
    450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
            500                 505                 510

Glu Gln Phe Ala Tyr Val Asp Arg Arg Lys Asn Val Leu Lys Leu Ser
        515                 520                 525

Gln Gly Glu Phe Val Thr Leu Ala Lys Leu Glu Ala Ala Tyr Ser Ser
    530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Leu Gly Glu Ser Leu Gln Lys
            580                 585                 590

Ile Ala Arg Asp Glu Gly Leu Gln Ser Tyr Glu Val Pro Arg Asp Phe
        595                 600                 605

Ile Ile Glu Thr Asp Pro Phe Thr Val Glu Asn Gly Leu Leu Ser Asp
    610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Ala Met Leu Gly Ala Ser Ala Ala Glu Ile Lys
        675                 680                 685

Pro Asp Ala His Phe Thr Asp Leu Gly Gly Asp Ser Leu Ser Ala Leu
    690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
            740                 745                 750

Val His Gly Lys Gly Ser Thr Thr Ile Lys Ala Ser Asp Leu Thr Leu
        755                 760                 765

Asp Lys Phe Ile Asp Glu Gln Thr Leu Glu Ala Ala Lys His Leu Pro
    770                 775                 780
```

-continued

Lys Pro Ala Asp Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
            805                 810                 815

Ala Gly Gly Lys Leu Ile Thr Ile Val Arg Gly Lys Asp Ala Ala Gln
        820                 825                 830

Ala Lys Ala Arg Leu Asp Ala Ala Tyr Glu Ser Gly Asp Pro Lys Leu
    835                 840                 845

Ala Gly His Tyr Gln Asp Leu Ala Ala Thr Thr Leu Glu Val Leu Ala
850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
            885                 890                 895

Asn His Val Leu Pro Tyr Asn Gln Leu Phe Gly Pro Asn Val Ala Gly
        900                 905                 910

Val Ala Glu Ile Ile Lys Leu Ala Ile Thr Thr Arg Ile Lys Pro Val
    915                 920                 925

Thr Tyr Leu Ser Thr Val Ala Val Ala Ala Gly Val Glu Pro Ser Ala
930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
            965                 970                 975

Val Leu Leu Arg Glu Ala His Asp Arg Thr Gly Leu Pro Val Arg Val
        980                 985                 990

Phe Arg Ser Asp Met Ile Leu Ala His Gln Lys Tyr Thr Gly Gln Val
    995                 1000                1005

Asn Ala Thr Asp Gln Phe Thr Arg Leu Val Gln Ser Leu Leu Ala
    1010                1015                1020

Thr Gly Leu Ala Pro Lys Ser Phe Tyr Glu Leu Asp Ala Gln Gly
    1025                1030                1035

Asn Arg Gln Arg Ala His Tyr Asp Gly Ile Pro Val Asp Phe Thr
    1040                1045                1050

Ala Glu Ser Ile Thr Thr Leu Gly Gly Asp Gly Leu Glu Gly Tyr
    1055                1060                1065

Arg Ser Tyr Asn Val Phe Asn Pro His Arg Asp Gly Val Gly Leu
    1070                1075                1080

Asp Glu Phe Val Asp Trp Leu Ile Glu Ala Gly His Pro Ile Thr
    1085                1090                1095

Arg Ile Asp Asp Tyr Asp Gln Trp Leu Ser Arg Phe Glu Thr Ser
    1100                1105                1110

Leu Arg Gly Leu Pro Glu Ser Lys Arg Gln Ala Ser Val Leu Pro
    1115                1120                1125

Leu Leu His Ala Phe Ala Arg Pro Gly Pro Ala Val Asp Gly Ser
    1130                1135                1140

Pro Phe Arg Asn Thr Val Phe Arg Thr Asp Val Gln Lys Ala Lys
    1145                1150                1155

Ile Gly Ala Glu His Asp Ile Pro His Leu Gly Lys Ala Leu Val
    1160                1165                1170

Leu Lys Tyr Ala Asp Asp Ile Lys Gln Leu Gly Leu Leu
    1175                1180                1185

<210> SEQ ID NO 8
<211> LENGTH: 459
<212> TYPE: PRT
<213> ORGANISM: Chromobacterium violaceum

<400> SEQUENCE: 8

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

```
Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 9
<211> LENGTH: 468
<212> TYPE: PRT
<213> ORGANISM: Pseudomonas aeruginosa

<400> SEQUENCE: 9

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
            85                  90                  95

Met Ala Asn Pro Arg Ala Ile Glu Leu Cys Arg Lys Leu Ala Glu Leu
        100                 105                 110

Ala Pro Gly Asp Leu Asp His Val Phe Leu Thr Thr Gly Gly Ser Thr
    115                 120                 125

Ala Val Asp Thr Ala Ile Arg Leu Met His Tyr Tyr Gln Asn Cys Arg
130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
            165                 170                 175

Pro Ala Glu Phe Asp Phe Leu Asp Glu Arg Ile His His Leu Ala Cys
        180                 185                 190

Pro Tyr Tyr Tyr Arg Ala Pro Glu Gly Leu Gly Glu Ala Glu Phe Leu
    195                 200                 205

Asp Gly Leu Val Asp Glu Phe Glu Arg Lys Ile Leu Glu Leu Gly Ala
210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
            245                 250                 255

Gln Arg Tyr Asp Val Leu Tyr Ile Ser Asp Glu Val Val Thr Ser Phe
        260                 265                 270

Gly Arg Leu Gly His Phe Phe Ala Ser Gln Ala Val Phe Gly Val Gln
    275                 280                 285

Pro Asp Ile Ile Leu Thr Ala Lys Gly Leu Thr Ser Gly Tyr Gln Pro
```

```
                    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 10
<211> LENGTH: 454
<212> TYPE: PRT
<213> ORGANISM: Pseudomonas syringae

<400> SEQUENCE: 10

Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
                20                  25                  30

Gly Pro Arg Ile Ile Thr Arg Ala Glu Gly Val Tyr Leu Trp Asp Ser
            35                  40                  45

Glu Gly Asn Lys Ile Leu Asp Gly Met Ser Gly Leu Trp Cys Val Ala
        50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Val Val His Ile Pro Gln Pro Tyr Trp Phe Gly Glu
            180                 185                 190
```

```
Gly Gly Asp Met Thr Pro Asp Glu Phe Gly Ile Trp Ala Ala Glu Gln
            195                 200                 205

Leu Glu Lys Lys Ile Leu Glu Leu Gly Val Glu Asn Val Gly Ala Phe
        210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Glu Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
        355                 360                 365

Leu Val Gly Glu Val Arg Gly Val Gly Leu Leu Gly Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
            420                 425                 430

Gln Ile Asp Glu Leu Val Glu Lys Ala Arg Thr Cys Leu Asp Leu Thr
        435                 440                 445

Leu Ala Val Leu Gln Gly
    450

<210> SEQ ID NO 11
<211> LENGTH: 467
<212> TYPE: PRT
<213> ORGANISM: Rhodobacter sphaeroides

<400> SEQUENCE: 11

Met Thr Arg Asn Asp Ala Thr Asn Ala Ala Gly Ala Val Gly Ala Ala
1               5                   10                  15

Met Arg Asp His Ile Leu Leu Pro Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
    50                  55                  60

Ala Gln Val Gly Tyr Gly Arg Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110
```

Leu Asn Arg Ile Phe Phe Thr Thr Gly Gly Ser Thr Ala Val Asp Ser
            115                 120                 125

Ala Leu Arg Phe Ser Glu Phe Tyr Asn Asn Val Leu Gly Arg Pro Gln
        130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Leu Ala Ser Leu
        355                 360                 365

Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
        435                 440                 445

Ala Ile Thr Glu Val Ser Ala Ala His Gly Leu Thr Ala Lys Glu Pro
    450                 455                 460

Ala Ala Val
465

<210> SEQ ID NO 12
<211> LENGTH: 459
<212> TYPE: PRT
<213> ORGANISM: Escherichia coli

<400> SEQUENCE: 12

Met Asn Arg Leu Pro Ser Ser Ala Ser Ala Leu Ala Cys Ser Ala His

```
1               5                   10                  15
Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
            35                  40                  45

Gly Phe Leu Glu Tyr Arg Lys Ser Val Thr Ala Gly Asp Tyr Gly
            50                  55                  60

Ala Val Glu Trp Gln Ala Gly Ser Leu Asn Thr Leu Val Asp Thr Gln
 65             70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
            115                 120                 125

Leu Ala Lys Thr Leu Ala Ala Leu Thr Pro Gly Lys Leu Lys Tyr Ser
            130                 135                 140

Phe Phe Cys Asn Ser Gly Thr Glu Ser Val Glu Ala Ala Leu Lys Leu
145             150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
            195                 200                 205

His Val Pro Phe Gly Asn Ile Glu Ala Met Arg Thr Ala Leu Asn Glu
            210                 215                 220

Cys Lys Lys Thr Gly Asp Asp Val Ala Ala Val Ile Leu Glu Pro Ile
225             230                 235                 240

Gln Gly Glu Gly Gly Val Ile Leu Pro Pro Pro Gly Tyr Leu Thr Ala
                245                 250                 255

Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
            275                 280                 285

Glu Asn Val Gln Pro Asp Ile Leu Cys Leu Ala Lys Ala Leu Gly Gly
            290                 295                 300

Gly Val Met Pro Ile Gly Ala Thr Ile Ala Thr Glu Glu Val Phe Ser
305             310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
            355                 360                 365

Gly Phe Arg Gln Leu Ala Arg Glu Tyr Pro Asp Leu Val Gln Glu Ala
            370                 375                 380

Arg Gly Lys Gly Met Leu Met Ala Ile Glu Phe Val Asp Asn Glu Ile
385             390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430
```

```
Leu Thr Ile Glu Gln Cys Glu Leu Val Ile Lys Ala Ala Arg Lys Ala
        435                 440                 445

Leu Ala Ala Met Arg Val Ser Val Glu Glu Ala
    450                 455

<210> SEQ ID NO 13
<211> LENGTH: 453
<212> TYPE: PRT
<213> ORGANISM: Vibrio fluvialis

<400> SEQUENCE: 13

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
```

```
              340                 345                 350
Ala Pro Arg Phe Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
        435                 440                 445

Phe Ala Glu Val Ala
        450

<210> SEQ ID NO 14
<211> LENGTH: 224
<212> TYPE: PRT
<213> ORGANISM: Bacillus sp.

<400> SEQUENCE: 14

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220

<210> SEQ ID NO 15
<211> LENGTH: 222
<212> TYPE: PRT
<213> ORGANISM: Nocardia sp.
```

<400> SEQUENCE: 15

```
Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu Glu His Leu Ile
            20                  25                  30

Ala Lys Ser Val Glu Lys Arg Arg Arg Asp Phe Ile Gly Ala Arg His
        35                  40                  45

Cys Ala Arg Leu Ala Leu Ala Glu Leu Gly Glu Pro Pro Val Ala Ile
    50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Ala Val Ala His Lys
                85                  90                  95

Met Arg Phe Arg Ser Ile Gly Ile Asp Ala Glu Pro His Ala Thr Leu
            100                 105                 110

Pro Glu Gly Val Leu Asp Ser Val Ser Leu Pro Pro Glu Arg Glu Trp
        115                 120                 125

Leu Lys Thr Thr Asp Ser Ala Leu His Leu Asp Arg Leu Leu Phe Cys
    130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
    210                 215                 220
```

<210> SEQ ID NO 16
<211> LENGTH: 269
<212> TYPE: PRT
<213> ORGANISM: Bacillus cereus

<400> SEQUENCE: 16

```
Met Ile Asn Lys Thr Leu Leu Gln Lys Arg Phe Asn Val Ala Ala Val
1               5                   10                  15

Ser Tyr Asp Gln Tyr Ala Asn Val Gln Lys Lys Met Ala His Ser Leu
            20                  25                  30

Leu Ser Thr Leu Asn Arg Arg Tyr Ser Thr Asn Ser Ser Ile Arg Ile
        35                  40                  45

Leu Glu Leu Gly Cys Gly Thr Gly Tyr Val Thr Glu Gln Leu Ser Asn
    50                  55                  60

Leu Phe Pro Lys Ala Gln Ile Thr Ala Ile Asp Phe Ala Glu Ser Met
65                  70                  75                  80

Ile Ala Val Ala Lys Thr Arg Gln Asn Val Asn Asn Val Thr Phe Tyr
                85                  90                  95

Cys Glu Asp Ile Glu Arg Leu Arg Leu Glu Glu Thr Tyr Asp Val Ile
            100                 105                 110

Ile Ser Asn Ala Thr Phe Gln Trp Leu Asn Asp Leu Lys Gln Val Ile
        115                 120                 125

Thr Asn Leu Phe Arg His Leu Ser Ile Glu Gly Ile Leu Leu Phe Ser
    130                 135                 140
```

```
Thr Phe Gly Gln Glu Thr Phe Gln Glu Leu His Ala Ser Phe Gln Arg
145                 150                 155                 160

Ala Lys Glu Glu Lys Asn Ile Gln Asn Glu Thr Ser Ile Gly Gln Arg
            165                 170                 175

Phe Tyr Ser Lys Asn Gln Leu Arg His Ile Cys Glu Ile Glu Thr Gly
            180                 185                 190

Asp Val His Val Ser Glu Thr Cys Tyr Ile Glu Arg Phe Thr Glu Val
            195                 200                 205

Arg Glu Phe Leu His Ser Ile Arg Lys Val Gly Ala Thr Asn Ser Asn
        210                 215                 220

Glu Glu Ser Tyr Cys Gln Ser Pro Ser Leu Phe Arg Ala Met Leu Arg
225                 230                 235                 240

Ile Tyr Glu Arg Asp Phe Thr Gly Asn Glu Gly Ile Met Ala Thr Tyr
                245                 250                 255

His Ala Leu Phe Val His Ile Thr Lys Glu Gly Lys Arg
                260                 265

<210> SEQ ID NO 17
<211> LENGTH: 256
<212> TYPE: PRT
<213> ORGANISM: Escherichia coli

<400> SEQUENCE: 17

Met Asn Asn Ile Trp Trp Gln Thr Lys Gly Gln Gly Asn Val His Leu
1               5                   10                  15

Val Leu Leu His Gly Trp Gly Leu Asn Ala Glu Val Trp Arg Cys Ile
            20                  25                  30

Asp Glu Glu Leu Ser Ser His Phe Thr Leu His Leu Val Asp Leu Pro
        35                  40                  45

Gly Phe Gly Arg Ser Arg Gly Phe Gly Ala Leu Ser Leu Ala Asp Met
    50                  55                  60

Ala Glu Ala Val Leu Gln Gln Ala Pro Asp Lys Ala Ile Trp Leu Gly
65                  70                  75                  80

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
            100                 105                 110

Ala Arg Asp Glu Trp Pro Gly Ile Lys Pro Asp Val Leu Ala Gly Phe
        115                 120                 125

Gln Gln Gln Leu Ser Asp Asp Phe Gln Arg Thr Val Glu Arg Phe Leu
    130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
        195                 200                 205

Leu Val Pro Arg Lys Val Pro Met Leu Asp Lys Leu Trp Pro His
    210                 215                 220

Ser Glu Ser Tyr Ile Phe Ala Lys Ala Ala His Ala Pro Phe Ile Ser
225                 230                 235                 240

His Pro Ala Glu Phe Cys His Leu Leu Val Ala Leu Lys Gln Arg Val
                245                 250                 255
```

<210> SEQ ID NO 18
<211> LENGTH: 259
<212> TYPE: PRT
<213> ORGANISM: Bacillus subtilis

<400> SEQUENCE: 18

```
Met Met Gln Glu Glu Thr Phe Tyr Ser Val Arg Met Arg Ala Ser Met
1               5                   10                  15

Asn Gly Ser His Glu Asp Gly Gly Lys His Ile Ser Gly Gly Glu Arg
            20                  25                  30

Leu Ile Pro Phe His Glu Met Lys His Thr Val Asn Ala Leu Leu Glu
        35                  40                  45

Lys Gly Leu Ser His Ser Arg Gly Lys Pro Asp Phe Met Gln Ile Gln
    50                  55                  60

Phe Glu Glu Val His Glu Ser Ile Lys Thr Ile Gln Pro Leu Pro Val
65                  70                  75                  80

His Thr Asn Glu Val Ser Cys Pro Glu Glu Gly Gln Lys Leu Ala Arg
                85                  90                  95

Leu Leu Leu Glu Lys Glu Gly Val Ser Arg Asp Val Ile Glu Lys Ala
            100                 105                 110

Tyr Glu Gln Ile Pro Glu Trp Ser Asp Val Arg Gly Ala Val Leu Phe
        115                 120                 125

Asp Ile His Thr Gly Lys Arg Met Asp Gln Thr Lys Glu Lys Gly Val
    130                 135                 140

Arg Val Ser Arg Met Asp Trp Pro Asp Ala Asn Phe Glu Lys Trp Ala
145                 150                 155                 160

Leu His Ser His Val Pro Ala His Ser Arg Ile Lys Glu Ala Leu Ala
                165                 170                 175

Leu Ala Ser Lys Val Ser Arg His Pro Ala Val Val Ala Glu Leu Cys
            180                 185                 190

Trp Ser Asp Asp Pro Asp Tyr Ile Thr Gly Tyr Val Ala Gly Lys Lys
        195                 200                 205

Met Gly Tyr Gln Arg Ile Thr Ala Met Lys Glu Tyr Gly Thr Glu Glu
    210                 215                 220

Gly Cys Arg Val Phe Phe Ile Asp Gly Ser Asn Asp Val Asn Thr Tyr
225                 230                 235                 240

Ile His Asp Leu Glu Lys Gln Pro Ile Leu Ile Glu Trp Glu Glu Asp
                245                 250                 255

His Asp Ser
```

<210> SEQ ID NO 19
<211> LENGTH: 389
<212> TYPE: PRT
<213> ORGANISM: Bacillus subtilis

<400> SEQUENCE: 19

```
Met Lys Ile Asp Ser Trp Leu Asn Glu Arg Leu Asp Arg Met Lys Glu
1               5                   10                  15

Ala Gly Val His Arg Asn Leu Arg Ser Met Asp Gly Ala Pro Val Pro
            20                  25                  30

Glu Arg Asn Ile Asp Gly Glu Asn Gln Thr Val Trp Ser Ser Asn Asn
        35                  40                  45

Tyr Leu Gly Leu Ala Ser Asp Arg Arg Leu Ile Asp Ala Ala Gln Thr
    50                  55                  60
```

Ala Leu Gln Gln Phe Gly Thr Gly Ser Ser Gly Ser Arg Leu Thr Thr
65                  70                  75                  80

Gly Asn Ser Val Trp His Glu Lys Leu Glu Lys Lys Ile Ala Ser Phe
                85                  90                  95

Lys Leu Thr Glu Ala Ala Leu Leu Phe Ser Ser Gly Tyr Leu Ala Asn
            100                 105                 110

Val Gly Val Leu Ser Ser Leu Pro Glu Lys Glu Asp Val Ile Leu Ser
        115                 120                 125

Asp Gln Leu Asn His Ala Ser Met Ile Asp Gly Cys Arg Leu Ser Lys
130                 135                 140

Ala Asp Thr Val Val Tyr Arg His Ile Asp Met Asn Asp Leu Glu Asn
145                 150                 155                 160

Lys Leu Asn Glu Thr Gln Arg Tyr Gln Arg Arg Phe Ile Val Thr Asp
            165                 170                 175

Gly Val Phe Ser Met Asp Gly Thr Ile Ala Pro Leu Asp Gln Ile Ile
        180                 185                 190

Ser Leu Ala Lys Arg Tyr His Ala Phe Val Val Asp Asp Ala His
        195                 200                 205

Ala Thr Gly Val Leu Gly Asp Ser Gly Gln Gly Thr Ser Glu Tyr Phe
210                 215                 220

Gly Val Cys Pro Asp Ile Val Ile Gly Thr Leu Ser Lys Ala Val Gly
225                 230                 235                 240

Ala Glu Gly Gly Phe Ala Ala Gly Ser Ala Val Phe Ile Asp Phe Leu
                245                 250                 255

Leu Asn His Ala Arg Thr Phe Ile Phe Gln Thr Ala Ile Pro Pro Ala
            260                 265                 270

Ser Cys Ala Ala His Glu Ala Phe Asn Ile Ile Glu Ala Ser Arg
        275                 280                 285

Glu Lys Arg Gln Leu Leu Phe Ser Tyr Ile Ser Met Ile Arg Thr Ser
290                 295                 300

Leu Lys Asn Met Gly Tyr Val Val Lys Gly Asp His Thr Pro Ile Ile
305                 310                 315                 320

Pro Val Val Ile Gly Asp Ala His Lys Thr Val Leu Phe Ala Glu Lys
            325                 330                 335

Leu Gln Gly Lys Gly Ile Tyr Ala Pro Ala Ile Arg Pro Pro Thr Val
        340                 345                 350

Ala Pro Gly Glu Ser Arg Ile Arg Ile Thr Ile Thr Ser Asp His Ser
        355                 360                 365

Met Gly Asp Ile Asp His Leu Leu Gln Thr Phe His Ser Ile Gly Lys
370                 375                 380

Glu Leu His Ile Ile
385

<210> SEQ ID NO 20
<211> LENGTH: 251
<212> TYPE: PRT
<213> ORGANISM: Escherichia coli

<400> SEQUENCE: 20

Met Ala Thr Val Asn Lys Gln Ala Ile Ala Ala Phe Gly Arg Ala
1               5                   10                  15

Ala Ala His Tyr Glu Gln His Ala Asp Leu Gln Arg Gln Ser Ala Asp
            20                  25                  30

Ala Leu Leu Ala Met Leu Pro Gln Arg Lys Tyr Thr His Val Leu Asp
        35                  40                  45

```
Ala Gly Cys Gly Pro Gly Trp Met Ser Arg His Trp Arg Glu Arg His
    50                  55                  60

Ala Gln Val Thr Ala Leu Asp Leu Ser Pro Pro Met Leu Val Gln Ala
65                  70                  75                  80

Arg Gln Lys Asp Ala Ala Asp His Tyr Leu Ala Gly Asp Ile Glu Ser
                85                  90                  95

Leu Pro Leu Ala Thr Ala Thr Phe Asp Leu Ala Trp Ser Asn Leu Ala
                100                 105                 110

Val Gln Trp Cys Gly Asn Leu Ser Thr Ala Leu Arg Glu Leu Tyr Arg
            115                 120                 125

Val Val Arg Pro Lys Gly Val Val Ala Phe Thr Thr Leu Val Gln Gly
    130                 135                 140

Ser Leu Pro Glu Leu His Gln Ala Trp Gln Ala Val Asp Glu Arg Pro
145                 150                 155                 160

His Ala Asn Arg Phe Leu Pro Pro Asp Glu Ile Glu Gln Ser Leu Asn
                165                 170                 175

Gly Val His Tyr Gln His His Ile Gln Pro Ile Thr Leu Trp Phe Asp
                180                 185                 190

Asp Ala Leu Ser Ala Met Arg Ser Leu Lys Gly Ile Gly Ala Thr His
            195                 200                 205

Leu His Glu Gly Arg Asp Pro Arg Ile Leu Thr Arg Ser Gln Leu Gln
    210                 215                 220

Arg Leu Gln Leu Ala Trp Pro Gln Gln Gln Gly Arg Tyr Pro Leu Thr
225                 230                 235                 240

Tyr His Leu Phe Leu Gly Val Ile Ala Arg Glu
                245                 250

<210> SEQ ID NO 21
<211> LENGTH: 246
<212> TYPE: PRT
<213> ORGANISM: Lactobacillus brevis

<400> SEQUENCE: 21

Met Ala Ala Asn Glu Phe Ser Glu Thr His Arg Val Val Tyr Tyr Glu
1               5                   10                  15

Ala Asp Asp Thr Gly Gln Leu Thr Leu Ala Met Leu Ile Asn Leu Phe
                20                  25                  30

Val Leu Val Ser Glu Asp Gln Asn Asp Ala Leu Gly Leu Ser Thr Ala
            35                  40                  45

Phe Val Gln Ser His Gly Val Gly Trp Val Val Thr Gln Tyr His Leu
    50                  55                  60

His Ile Asp Glu Leu Pro Arg Thr Gly Ala Gln Val Thr Ile Lys Thr
65                  70                  75                  80

Arg Ala Thr Ala Tyr Asn Arg Tyr Phe Ala Tyr Arg Glu Tyr Trp Leu
                85                  90                  95

Leu Asp Asp Ala Gly Gln Val Leu Ala Tyr Gly Glu Gly Ile Trp Val
                100                 105                 110

Thr Met Ser Tyr Ala Thr Arg Lys Ile Thr Thr Ile Pro Ala Glu Val
            115                 120                 125

Met Ala Pro Tyr His Ser Glu Glu Gln Thr Arg Leu Pro Arg Leu Pro
    130                 135                 140

Arg Pro Asp His Phe Asp Glu Ala Val Asn Gln Thr Leu Lys Pro Tyr
145                 150                 155                 160

Thr Val Arg Tyr Phe Asp Ile Asp Gly Asn Gly His Val Asn Asn Ala
```

```
                   165                 170                 175

His Tyr Phe Asp Trp Met Leu Asp Val Leu Pro Ala Thr Phe Leu Arg
                180                 185                 190

Ala His His Pro Thr Asp Val Lys Ile Arg Phe Glu Asn Glu Val Gln
            195                 200                 205

Tyr Gly His Gln Val Thr Ser Glu Leu Ser Gln Ala Ala Leu Thr
        210                 215                 220

Thr Gln His Met Ile Lys Val Gly Asp Leu Thr Ala Val Lys Ala Thr
225                 230                 235                 240

Ile Gln Trp Asp Asn Arg
                245

<210> SEQ ID NO 22
<211> LENGTH: 261
<212> TYPE: PRT
<213> ORGANISM: Lactobacillus plantarum

<400> SEQUENCE: 22

Met Ala Thr Leu Gly Ala Asn Ala Ser Leu Tyr Ser Glu Gln His Arg
1               5                   10                  15

Ile Thr Tyr Tyr Glu Cys Asp Arg Thr Gly Arg Ala Thr Leu Thr Thr
                20                  25                  30

Leu Ile Asp Ile Ala Val Leu Ala Ser Glu Asp Gln Ser Asp Ala Leu
            35                  40                  45

Gly Leu Thr Thr Glu Met Val Gln Ser His Gly Val Gly Trp Val Val
        50                  55                  60

Thr Gln Tyr Ala Ile Asp Ile Thr Arg Met Pro Arg Gln Asp Glu Val
65                  70                  75                  80

Val Thr Ile Ala Val Arg Gly Ser Ala Tyr Asn Pro Tyr Phe Ala Tyr
                85                  90                  95

Arg Glu Phe Trp Ile Arg Asp Ala Asp Gly Gln Gln Leu Ala Tyr Ile
                100                 105                 110

Thr Ser Ile Trp Val Met Met Ser Gln Thr Thr Arg Arg Ile Val Lys
            115                 120                 125

Ile Leu Pro Glu Leu Val Ala Pro Tyr Gln Ser Glu Val Val Lys Arg
        130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
                180                 185                 190

Ala Thr Phe Leu Leu Gln His Asp Leu Val His Val Asp Val Arg Tyr
            195                 200                 205

Glu Asn Glu Val Lys Tyr Gly Gln Thr Val Thr Ala His Ala Asn Ile
        210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
            260

<210> SEQ ID NO 23
<211> LENGTH: 384
```

<212> TYPE: PRT
<213> ORGANISM: Escherichia coli

<400> SEQUENCE: 23

```
Met Ser Trp Gln Glu Lys Ile Asn Ala Ala Leu Asp Ala Arg Arg Ala
1               5                   10                  15

Ala Asp Ala Leu Arg Arg Tyr Pro Val Ala Gln Gly Ala Gly Arg
                20                  25                  30

Trp Leu Val Ala Asp Asp Arg Gln Tyr Leu Asn Phe Ser Ser Asn Asp
                35                  40                  45

Tyr Leu Gly Leu Ser His His Pro Gln Ile Ile Arg Ala Trp Gln Gln
            50                  55                  60

Gly Ala Glu Gln Phe Gly Ile Gly Ser Gly Ser Gly His Val Ser
65                  70                  75                  80

Gly Tyr Ser Val Val His Gln Ala Leu Glu Glu Leu Ala Glu Trp
                85                  90                  95

Leu Gly Tyr Ser Arg Ala Leu Leu Phe Ile Ser Gly Phe Ala Ala Asn
                100                 105                 110

Gln Ala Val Ile Ala Ala Met Met Ala Lys Glu Asp Arg Ile Ala Ala
                115                 120                 125

Asp Arg Leu Ser His Ala Ser Leu Leu Glu Ala Ala Ser Leu Ser Pro
                130                 135                 140

Ser Gln Leu Arg Arg Phe Ala His Asn Asp Val Thr His Leu Ala Arg
145                 150                 155                 160

Leu Leu Ala Ser Pro Cys Pro Gly Gln Gln Met Val Thr Glu Gly
                165                 170                 175

Val Phe Ser Met Asp Gly Asp Ser Ala Pro Leu Ala Glu Ile Gln Gln
                180                 185                 190

Val Thr Gln Gln His Asn Gly Trp Leu Met Val Asp Asp Ala His Gly
                195                 200                 205

Thr Gly Val Ile Gly Glu Gln Gly Arg Gly Ser Cys Trp Leu Gln Lys
            210                 215                 220

Val Lys Pro Glu Leu Leu Val Thr Phe Gly Lys Gly Phe Gly Val
225                 230                 235                 240

Ser Gly Ala Ala Val Leu Cys Ser Ser Thr Val Ala Asp Tyr Leu Leu
                245                 250                 255

Gln Phe Ala Arg His Leu Ile Tyr Ser Thr Ser Met Pro Pro Ala Gln
                260                 265                 270

Ala Gln Ala Leu Arg Ala Ser Leu Ala Val Ile Arg Ser Asp Glu Gly
                275                 280                 285

Asp Ala Arg Arg Glu Lys Leu Ala Ala Leu Ile Thr Arg Phe Arg Ala
                290                 295                 300

Gly Val Gln Asp Leu Pro Phe Thr Leu Ala Asp Ser Cys Ser Ala Ile
305                 310                 315                 320

Gln Pro Leu Ile Val Gly Asp Asn Ser Arg Ala Leu Gln Leu Ala Glu
                325                 330                 335

Lys Leu Arg Gln Gln Gly Cys Trp Val Thr Ala Ile Arg Pro Pro Thr
                340                 345                 350

Val Pro Ala Gly Thr Ala Arg Leu Arg Leu Thr Leu Thr Ala Ala His
                355                 360                 365

Glu Met Gln Asp Ile Asp Arg Leu Leu Glu Val Leu His Gly Asn Gly
                370                 375                 380
```

<210> SEQ ID NO 24

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 24

His His His His His His
1               5
```

MATERIALS AND METHODS UTILIZING BIOTIN PRODUCING MUTANT HOSTS FOR THE PRODUCTION OF 7-CARBON CHEMICALS

CROSS-REFERENCE TO RELATED APPLICATIONS

The present application claims the benefit of U.S. Provisional Application No. 62/366,565, filed on Jul. 25, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 24, 2017, is named 12444_0684-00000_SL.txt and is 111,836 bytes in size.

BACKGROUND

This disclosure relates to methods for regulating biosynthesis of at least one seven carbon compounds. This disclosure relates to materials and methods for regulating biosynthesis of at least one of pimelic acid, 7-aminoheptanoic acid, 7-hydroxyheptanoic acid, heptamethylenediamine, 7-aminoheptanoland 1,7-heptanediol (hereafter "C7 building blocks") using a pathway having a pimelyl-ACP intermediate. The methods include the step of downregulating the activity of BioF, an 8-amino-7-oxononanoate synthase. The disclosure also relates to recombinant hosts by fermentation in which the above-mentioned method is performed. Also disclosed are pimeloyl-ACP producing recombinant hosts that include a deletion of a bioF gene.

Nylons are synthetic polyamides which are sometimes synthesized by the condensation polymerisation of a diamine with a dicarboxylic acid. Similarly, Nylons may be produced by the condensation polymerisation of lactams. A ubiquitous Nylon is Nylon 6,6, which is produced by reaction of hexamethylenediamine (HMD) and adipic acid. Nylon 6 is produced by a ring opening polymerisation of caprolactam (Anton & Baird, Polyamides Fibers, Encyclopedia of Polymer Science and Technology, 2001).

Nylon 7 and Nylon 7,7 represent novel polyamides with value-added characteristics compared to Nylon 6 and Nylon 6,6. Nylon 7 is produced by polymerisation of 7-aminoheptanoic acid, whereas Nylon 7,7 is produced by condensation polymerisation of pimelic acid and heptamethylenediamine. No economically viable petrochemical routes exist to producing the monomers for Nylon 7 and Nylon 7,7.

Given no economically cost competitive petrochemical monomer feedstocks, biotechnology offers an alternative approach via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

However, no wild-type prokaryote or eukaryote naturally overproduces or excretes C7 building blocks to the extracellular environment. Nevertheless, the metabolism of pimelic acid has been reported.

The dicarboxylic acid, pimelic acid, is converted efficiently as a carbon source by a number of bacteria and yeasts via β-oxidation into central metabolites. β-oxidation of CoEnzyme A (CoA) activated pimelate to CoA-activated 3-oxopimelate facilitates further catabolism via, for example, pathways associated with aromatic substrate degradation. The catabolism of 3-oxopimeloyl-CoA to acetyl-CoA and glutaryl-CoA by several bacteria has been characterized comprehensively (Harwood and Parales, *Annual Review of Microbiology*, 1996, 50, 553-590).

The optimality principle states that microorganisms regulate their biochemical networks to support maximum biomass growth. Beyond the need to express heterologous pathways in a host organism, directing carbon flux towards C7 building blocks that serve as carbon sources rather than to biomass growth constituents, contradicts the optimality principle. For example, transferring the 1-butanol pathway from *Clostridium* species into other production strains has often fallen short by an order of magnitude compared to the production performance of native producers (Shen et al., *Appl. Environ. Microbiol.*, 2011, 77(9), 2905-2915).

The efficient synthesis of the C7 aliphatic backbone precursor is a key consideration in synthesizing C7 building blocks prior to forming terminal functional groups, such as carboxyl, amine or hydroxyl groups, on the C7 aliphatic backbone. Accordingly, against this background, it is clear that there is a need for methods for producing pimelic acid, 7-aminoheptanoic acid, heptamethylenediamine, 7-hydroxyheptanoic acid, 7-aminoheptanol and 1,7-heptanediol (hereafter "C7 building blocks") wherein the methods are biocatalyst-based.

SUMMARY

Described herein are methods and genetically modified hosts that allow for more efficient use of seven carbon aliphatic backbone precursors and production of C7 building blocks, for example, by use of a recombinant host in a bioF deficient background.

The present disclosure relates to regulating biosynthesis for certain seven-carbon building blocks ("C7 building blocks") by downregulating the activity of a BioF. In one embodiment, downregulating the activity of BioF comprises downregulating the expression of a BioF protein. In another embodiment, downregulating the activity of BioF comprises downregulating the activity of the protein itself. The pathway for producing the C7 building blocks has a pimelyl-ACP intermediate. The C7 building blocks may include, for example, pimelic acid, 7-aminoheptanoate ("7-AHA"), 7-hydroxyheptanoate, heptamethylenediamine, 7-aminoheptanol and 1,7-heptanediol.

In some embodiments, the biochemical pathways for the production of 7-AHA currently being pursued are based on the production of pimelic acid, followed by the conversion of pimelic acid to 7-AHA. See FIG. 1. For example, *E. coli* may act as a host for the pathways producing pimelic acid its subsequent conversion to 7-AHA.

Pimeloyl-ACP, or pimelyl-ACP, is an intermediate of the biotin pathway in host, such as *E. coli*. For example, some methods in this disclosure for producing pimelic acid in *E. coli* are focused on metabolic engineering approaches, such as increasing the flux through this pathway, and the effective interception of the pimelic acid intermediate. See FIG. 1.

Pimelic acid and pimelate, 7-hydroxyheptanoic acid and 7-hydroxyheptanoate, and 7-aminoheptanoic acid and 7-aminoheptanoate are used interchangeably herein to refer to the compound in any of its neutral or ionized forms, including any salt forms thereof. It is understood by those skilled in the art that the specific form will depend on pH. These pathways, metabolic engineering and cultivation strategies described herein rely on fatty acid elongation and synthesis enzymes or homologs accepting methyl-ester shielded dicarboxylic acids as substrates.

For compounds containing carboxylic acid groups such as organic monoacids, hydroxyacids, aminoacids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The salt can be isolated as is from the system as the salt or converted to the free acid by reducing the pH to below the pKa through addition of acid or treatment with an acidic ion exchange resin.

For compounds containing amine groups such as but not limited to organic amines, aminoacids and diamine, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-β-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases are known in the art and include aluminum hydroxide, calcium hydroxide, potassium hydroxide, sodium carbonate, sodium hydroxide, and the like. The salt can be isolated as is from the system as a salt or converted to the free amine by raising the pH to above the pKb through addition of base or treatment with a basic ion exchange resin.

For compounds containing both amine groups and carboxylic acid groups such as but not limited to aminoacids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-β-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid Acceptable inorganic bases include aluminum hydroxide, calcium hydroxide, potassium hydroxide, sodium carbonate, sodium hydroxide, and the like or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the pKa through addition of acid or treatment with an acidic ion exchange resin.

In the face of the optimality principle, it surprisingly has been discovered that appropriate non-natural pathways, feedstocks, host microorganisms, attenuation strategies to the host's biochemical network and cultivation strategies may be combined to efficiently produce one or more C7 building blocks. It has also been discovered that the pathway having pimelyl-ACP as intermediate can be regulated by downregulating the activity BioF. The BioF is ACP-dependent enzyme. It converts, for example, the pimeloyl-ACP to 8-amino-7-oxononanoic acid. The BioF is a 8-amino-7-oxononanoate synthase having at least 70% sequence identity or homology to the amino acid sequence set forth in SEQ ID NO: 23.

In some embodiments, a terminal amine group can be enzymatically formed using a co-transaminase or a deacetylase. See FIG. 5 and FIGS. 6A-6C.

In some embodiments, a terminal hydroxyl group can be enzymatically formed using a 4-hydroxybutyrate dehydrogenase, 5-hydroxypentanoate dehydrogenase or a 6-hydroxyhexanoate dehydrogenase or an alcohol dehydrogenase. See FIG. 7 and FIG. 8.

In one aspect, this disclosure features a method for biosynthesizing a product selected from the group consisting of pimelic acid, 7-aminoheptanoate, 7-hydroxyheptanoate, heptamethylenediamine, 7-aminoheptanol and 1,7-heptanediol. The method includes enzymatically synthesizing a C7 aliphatic backbone from (i) acetyl-CoA and malonyl-CoA via two cycles of methyl ester shielded carbon chain elongation or (ii) malonyl-ACP via two cycles of methyl-ester shielded carbon chain elongation, and enzymatically forming one or two terminal functional groups selected from the group consisting of carboxyl, amine, and hydroxyl groups in the backbone, thereby forming the product.

The present disclosure relates to a method for regulating biosynthesis of at least one C7 building block using a pathway having a pimelyl-ACP intermediate. The method may comprise the step of downregulating the activity of BioF.

The at least one C7 building block is selected from the group consisting of pimelic acid, 7-aminoheptanoate, 7-hydroxyheptanoate, heptamethylenediamine, 7-aminoheptanol and 1,7-heptanediol.

In some embodiments, the step of downregulating the activity of BioF may comprise reducing the activity to a level below that of a wild type BioF, for example, reducing the activity to zero. In one embodiment, downregulating the activity of BioF comprises downregulating the expression of BioF protein. In another embodiment, downregulating the activity of BioF comprises downregulating the activity of the protein itself.

In some embodiments, the method for regulating biosynthesis of at least one C7 building block may further comprise the step of overexpressing BioW and a CoA-specific BioF. BioW enzymatically converts pimelic acid to pimeloyl-CoA. The BioW is a pimeloyl-CoA ligase having at least 70% sequence identity or homology to the amino acid sequence set forth in SEQ ID NO: 18.

CoA-specific BioF enzymatically converts pimeloyl-CoA to 8-amino-7-oxo-nonanoic acid.

The above-mentioned CoA-specific BioF is a 8-amino-7-oxononanoate synthase having at least 70% sequence identity or homology to the amino acid sequence set forth in SEQ ID NO: 19.

The above-mentioned pathway comprises enzymatically synthesizing a C7 aliphatic backbone from malonyl-ACP via two cycles of methyl-ester shielded carbon chain elongation, and enzymatically forming two terminal functional groups selected from the group consisting of carboxyl, amine, and hydroxyl groups in said backbone, thereby forming the C7 building block.

A S-adenosyl-L-methionine (SAM)-dependent methyltransferase, or BioC, converts malonyl-ACP to malonyl-ACP methyl ester. The S-adenosyl-L-methionine (SAM)-dependent methyltransferase has at least 70% sequence identity or homology to the amino acid sequence set forth in SEQ ID NO: 20.

The C7 aliphatic backbone can be pimeloyl-ACP. A malonyl-ACP O-methyltransferase can convert malonyl-CoA to a malonyl-CoA methyl ester or can convert malonyl-ACP to a malonyl-ACP methyl ester. Each of the two cycles of carbon chain elongation can include using (i) a β-ketoacyl-ACP synthase or a β-ketothiolase, (ii) a 3-oxoacyl-ACP reductase, an acetoacetyl-CoA reductase, a 3-hydroxyacyl-CoA dehydrogenase or a 3-hydroxybutyryl-CoA dehydrogenase, (iii) an enoyl-CoA hydratase or a 3-hydroxyacyl-ACP dehydratase, and (iv) an enoyl-ACP reductase. Or the two cycles of carbon chain elongation may involve a trans-2-enoyl-CoA reductase to produce pimeloyl-ACP methyl ester from malonyl-ACP methyl ester.

The two terminal functional groups can be the same (e.g., amine or hydroxyl) or can be different (e.g., a terminal amine and a terminal carboxyl group; or a terminal hydroxyl group and a terminal carboxyl group). For example, the two terminal functional groups can be both amine, or the two terminal functional groups can be both hydroxyl groups. In other embodiments, the C7 building block may comprise a terminal amine and a terminal carboxyl group, or the C7 building block may comprise a terminal hydroxyl group and a terminal carboxyl group.

A 6-hydroxyhexanoate dehydrogenase, a 5-hydroxypentanoate dehydrogenase, a 4-hydroxybutyrate dehydratase, or an alcohol dehydrogenase can enzymatically form a hydroxyl group.

A thioesterase, an aldehyde dehydrogenase, a 7-oxoheptanoate dehydrogenase, a 6-oxohexanoate dehydrogenase, a CoA-transferase (e.g. a glutaconate CoA transferase), or a reversible CoA-ligase (e.g., a reversible succinate-CoA ligase) can enzymatically form a terminal carboxyl group.

The thioesterase ("TE") can have at least 70% sequence identity or homology to the amino acid sequence set forth in SEQ ID NO: 1.

A ω-transaminase or a deacetylase can enzymatically form an amine group. The ω-transaminase can have at least 70% sequence identity or homology to any one of the amino acid sequences set forth in SEQ ID NO. 8-13.

A carboxylate reductase ("CAR") and a phosphopantetheinyl transferase can form a terminal aldehyde group as an intermediate in forming the product. The carboxylate reductase can have at least 70% sequence identity or homology to any one of the amino acid sequences set forth in SEQ ID NO. 2-7.

Any of the methods can be performed in a recombinant host by fermentation. The host can be subjected to a cultivation strategy under aerobic, anaerobic, micro-aerobic or mixed oxygen/denitrification cultivation conditions. The host can be cultured under conditions of nutrient limitation. The host can be retained using a ceramic hollow fiber membrane to maintain a high cell density during fermentation.

The principal carbon source fed to the fermentation can derive from biological or non-biological feedstocks. In some embodiments, the biological feedstock is, includes, or derives from, at least one chosen from monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock is, or derives from, at least one chosen from natural gas, syngas, $CO_2/H_2$, methanol, ethanol, benzoate, non-volatile residue (NVR) or a caustic wash waste stream from cyclohexane oxidation processes, or a terephthalic acid/isophthalic acid mixture waste stream.

The recombinant host can be a prokaryote, e.g., from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis* or from the genus *Rhodococcus* such as *Rhodococcus equi*.

The recombinant host can be a eukaryote, e.g., a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxula adenoinivorans*, or from the genus *Kluyveromyces* such as *Kluyveromyces lactis*.

In any of the methods, the host's tolerance to high concentrations of at least one C7 building block can be improved through continuous cultivation in a selective environment.

Any of the recombinant hosts described herein further can include one or more of the following attenuated enzymes: polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the NADH or NADPH imbalance, an glutamate dehydrogenase dissipating the NADH or NADPH imbalance, a NADH/NADPH-utilizing glutamate dehydrogenase, a pimeloyl-CoA dehydrogenase; an acyl-CoA dehydrogenase accepting C7 building blocks and central precursors as substrates; a glutaryl-CoA dehydrogenase; or a pimeloyl-CoA synthetase.

Any of the recombinant hosts described herein further can overexpress one or more genes encoding: an acetyl-CoA synthetase, a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a L-alanine dehydrogenase; a L-glutamate dehydrogenase specific to the NADH or NADPH used to generate a co-factor imbalance; a methanol dehydrogenase, a formaldehyde dehydrogenase, a diamine transporter; a dicarboxylate transporter; an S-adenosylmethionine synthetase, and/or a multidrug transporter.

The disclosure also relates to a recombinant host for producing for pimeloyl-ACP. The recombinant host may comprise a deletion of a bioF gene. In some embodiments, the recombinant host expresses BioF activity at a level below that of a wild type. In some embodiments, the recombinant host does not express BioF activity.

In some embodiments, the recombinant host comprises at least one exogenous nucleic acid encoding bioW and a CoA-specific bioF.

Also disclosed herein is a non-naturally occurring organism comprising at least one exogenous nucleic acid encoding at least one polypeptide having the activity of at least one enzyme depicted in any one of FIGS. 1 to 21.

In some embodiments, a nucleic acid construct or expression vector comprises a polynucleotide encoding a polypeptide having 8-amino-7-oxononanoate synthase activity, wherein the polynucleotide is operably linked to one or more heterologous control sequences that direct production of the polypeptide and wherein the polypeptide having 8-amino-7-oxononanoate synthase activity is a polypeptide having at least 70% sequence identity or homology to the polypeptide of SEQ ID NO: 23.

In some embodiments, a nucleic acid construct or expression vector comprises a polynucleotide encoding a polypeptide having thioesterase activity, wherein the polynucleotide is operably linked to one or more heterologous control sequences that direct production of the polypeptide and wherein the polypeptide having thioesterase activity is selected from the group consisting of: (a) a polypeptide having at least 70% sequence identity or homology to the polypeptide of SEQ ID NO: 1; (b) a polypeptide having at least 70% sequence identity or homology to the polypeptide of SEQ ID NO: 21; and (c) a polypeptide having at least 70% sequence identity or homology to the polypeptide of SEQ ID NO: 22.

In some embodiments, a nucleic acid construct or expression vector comprises a polynucleotide encoding a polypeptide having carboxylate reductase activity, wherein the polynucleotide is operably linked to one or more heterologous control sequences that direct production of the polypeptide and wherein the polypeptide having carboxylate reductase activity is selected from the group consisting of: (a) a polypeptide having at least 70% sequence identity or homology to the polypeptide of SEQ ID NO: 2; (b) a polypeptide having at least 70% sequence identity or homology to the polypeptide of SEQ ID NO: 3; (c) a polypeptide having at least 70% sequence identity or homology to the polypeptide of SEQ ID NO: 4; (d) a polypeptide having at least 70% sequence identity or homology to the polypeptide of SEQ ID NO: 5; (e) a polypeptide having at least 70% sequence identity or homology to the polypeptide of SEQ ID NO: 6; and (f) a polypeptide having at least 70% sequence identity or homology to the polypeptide of SEQ ID NO: 7.

In some embodiments, a nucleic acid construct or expression vector comprises a polynucleotide encoding a polypeptide having ω-transaminase activity, wherein the polynucleotide is operably linked to one or more heterologous control sequences that direct production of the polypeptide and wherein the polypeptide having ω-transaminase activity is selected from the group consisting of: (a) a polypeptide having at least 70% sequence identity or homology to the polypeptide of SEQ ID NO: 8; (b) a polypeptide having at least 70% sequence identity or homology to the polypeptide of SEQ ID NO: 9; (c) a polypeptide having at least 70% sequence identity or homology to the polypeptide of SEQ ID NO: 10 (d) a polypeptide having at least 70% sequence identity or homology to the polypeptide of SEQ ID NO: 11; (e) a polypeptide having at least 70% sequence identity or homology to the polypeptide of SEQ ID NO: 12; and (f) a polypeptide having at least 70% sequence identity or homology to the polypeptide of SEQ ID NO: 13.

In some embodiments, a nucleic acid construct or expression vector comprises a polynucleotide encoding a polypeptide having phosphopantetheinyl transferase activity, wherein the polynucleotide is operably linked to one or more heterologous control sequences that direct production of the polypeptide and wherein the polypeptide having phosphopantetheinyl transferase activity is selected from the group consisting of: (a) a polypeptide having at least 70% sequence identity or homology to the polypeptide of SEQ ID NO: 14 and (b) a polypeptide having at least 70% sequence identity or homology to the polypeptide of SEQ ID NO: 15.

In some embodiments, a nucleic acid construct or expression vector comprises a polynucleotide encoding a polypeptide having pimeloyl-ACP methyl ester esterase activity, wherein the polynucleotide is operably linked to one or more heterologous control sequences that direct production of the polypeptide and wherein the polypeptide having pimeloyl-ACP methyl ester esterase activity is a polypeptide having at least 70% sequence identity or homology to the polypeptide of SEQ ID NO: 17.

In some embodiments, a nucleic acid construct or expression vector comprises a polynucleotide encoding a polypeptide having 6-carboxyhexanoate-CoA ligase activity, wherein the polynucleotide is operably linked to one or more heterologous control sequences that direct production of the polypeptide and wherein the polypeptide having 6-carboxyhexanoate-CoA ligase activity is a polypeptide having at least 70% sequence identity or homology to the polypeptide of SEQ ID NO: 18.

In some embodiments, a nucleic acid construct or expression vector comprises a polynucleotide encoding a polypeptide having 8-amino-7-oxononanoate synthase activity, wherein the polynucleotide is operably linked to one or more heterologous control sequences that direct production of the polypeptide and wherein the polypeptide having 8-amino-7-oxononanoate synthase activity is a polypeptide having at least 70% sequence identity or homology to the polypeptide of SEQ ID NO: 19.

In some embodiments, a nucleic acid construct or expression vector comprises a polynucleotide encoding a polypeptide having malonyl-ACP O-methyltransferase activity, wherein the polynucleotide is operably linked to one or more heterologous control sequences that direct production of the polypeptide and wherein the polypeptide having malonyl-ACP O-methyltransferase activity is a polypeptide having at least 70% sequence identity or homology to the polypeptide of SEQ ID NO: 20.

In some embodiments, a composition comprises any of the above-described nucleic acid construct or expression vector.

Also disclosed is a non-naturally occurring biochemical network comprising a 5-hydroxypentanoyl-CoA, an exogenous nucleic acid encoding a polypeptide having the activity of a β-ketothiolase classified under EC. 2.3.1, and a 3-oxo-7-hydroxyheptanoyl-CoA.

In some embodiments, a bio-derived, bio-based or fermentation-derived product comprises:

i. a composition comprising at least one bio-derived, bio-based or fermentation-derived compound produced or biosynthesized according to any one of claims 1-75 or any one of FIGS. 1-21, or any combination thereof;

ii. a bio-derived, bio-based or fermentation-derived polymer comprising the bio-derived, bio-based or fermentation-derived composition or compound of i., or any combination thereof;

iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof;

iv. a molded substance obtained by molding the bio-derived, bio-based or fermentation-derived polymer of ii. or the bio-derived, bio-based or fermentation-derived resin of iii., or any combination thereof;

v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of bio-derived, bio-based or fermentation-derived resin of iii., or bio-derived, bio-based or fermentation-derived molded substance of iv, or any combination thereof; or vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g. cell lysates) that can be used as sources of relevant enzymes. In the methods provided by the disclosure, all the steps can be performed in cells (e.g., host cells), all the steps can be performed using extracted enzymes, or some of the steps can be performed in cells and others can be performed using extracted enzymes.

Many of the enzymes described herein catalyze reversible reactions, and the reaction of interest may be the reverse of the described reaction. The schematic pathways shown in FIGS. 1-3 and 5-8 illustrate the reaction of interest for each of the intermediates.

The disclosure also provides the following additional embodiments:

Embodiment 1. A method for regulating biosynthesis of at least one C7 building block using a pathway having a pimeloyl-ACP intermediate, said method comprising the step of downregulating the activity of a BioF enzyme.

Embodiment 2. The method of embodiment 1, wherein the BioF has at least 70% sequence identity or homology to the amino acid sequence set forth in SEQ ID NO: 23.

Embodiment 3. The method of embodiment 1, wherein the at least one C7 building block is selected from the group consisting of pimelic acid, 7-aminoheptanoate, 7-hydroxyheptanoate, heptamethylenediamine, 7-aminoheptanol and 1,7-heptanediol.

Embodiment 4. The method of embodiment 1, wherein the step of downregulating the activity of BioF comprises reducing the activity to a level below that of a wild type BioF protein.

Embodiment 5. The method of embodiment 1, wherein the step of downregulating the activity of BioF comprises reducing the activity to zero.

Embodiment 6. A method for regulating biosynthesis of at least one C7 building block using a pathway having a pimeloyl-ACP intermediate, said method comprising
the step of downregulating the activity of BioF; and
the step of overexpressing BioW and a CoA-specific BioF.

Embodiment 7. The method of embodiment 6, wherein said BioW enzymatically converts pimelic acid to pimeloyl-CoA.

Embodiment 8. The method of embodiment 6 or 7, wherein said BioW is a pimeloyl-CoA ligase having at least 70% sequence identity or homology to the amino acid sequence set forth in SEQ ID NO: 14.

Embodiment 9. The method of any one of embodiments 6-8, wherein CoA-specific BioF enzymatically converts pimeloyl-CoA to 8-amino-7-oxo-nonanoic acid.

Embodiment 10. The method of any one of embodiments 6-9, wherein said CoA-specific BioF is a 8-amino-7-oxononanoate synthase having at least 70% sequence identity or homology to the amino acid sequence set forth in SEQ ID NO: 15.

Embodiment 11. The method of embodiment 1, wherein said pathway comprises enzymatically synthesizing a C7 aliphatic backbone from malonyl-ACP via two cycles of methyl-ester shielded carbon chain elongation, and enzymatically forming two terminal functional groups independently selected from the group consisting of carboxyl, amine, and hydroxyl groups in said backbone, thereby forming the C7 building block.

Embodiment 12. The method of embodiment 11, wherein a S-adenosyl-L-methionine (SAM)-dependent methyltransferase converts malonyl-ACP to malonyl-ACP methyl ester.

Embodiment 13. The method of embodiment 11, wherein the S-adenosyl-L-methionine (SAM)-dependent methyltransferase has at least 70% sequence identity or homology to the amino acid sequence set forth in SEQ ID NO: 16.

Embodiment 14. The method of embodiment 10, wherein each of said two cycles of carbon chain elongation comprises using (i) a β-ketoacyl-ACP synthase, (ii) a 3-oxoacyl-ACP reductase, (iii) a 3-hydroxyacyl-ACP dehydratase, and (iv) an enoyl-ACP reductase.

Embodiment 15. The method of embodiment 10, wherein said two cycles of carbon chain elongation produce pimeloyl-ACP methyl ester from malonyl-ACP methyl ester using a trans-2-enoyl-CoA reductase.

Embodiment 16. The method of any one of embodiments 1-15, wherein said two terminal functional groups are the same.

Embodiment 17. The method of any one of embodiments 1-16, wherein said two terminal functional groups are amine.

Embodiment 18. The method of any one of embodiments 1-16, wherein said two terminal functional groups are hydroxyl groups.

Embodiment 19. The method of any one of embodiments 1-15, wherein said two terminal functional groups are different.

Embodiment 20. The method of any one of embodiments 1-15 and 19, wherein said at least one C7 building block comprises a terminal amine and a terminal carboxyl group.

Embodiment 21. The method of any one of embodiments 1-15 and 19, wherein said at least one C7 building block comprises a terminal hydroxyl group and a terminal carboxyl group.

Embodiment 22. The method of any one of embodiments 1-21, wherein the hydroxyl group is enzymatically formed by a 6-hydroxyhexanoate dehydrogenase, a 5-hydroxypentanoate dehydrogenase, a 4-hydroxybutyrate dehydratase, or an alcohol dehydrogenase.

Embodiment 23. The method of any one of embodiments 1-22, wherein the carboxyl group is enzymatically formed by a thioesterase, an aldehyde dehydrogenase, a 7-oxoheptanoate dehydrogenase, a 6-oxohexanoate dehydrogenase, a glutaconate CoA-transferase, or a reversible succinyl-CoA ligase.

Embodiment 24. The method of embodiment 23, wherein said thioesterase has at least 70% sequence identity or homology to the amino acid sequence set forth in SEQ ID NO: 21 or 22.

Embodiment 25. The method of any one of embodiments 1-24, wherein the amine group is enzymatically formed by a ω-transaminase or a deacetylase.

Embodiment 26. The method of embodiment 25, wherein said ω-transaminase has at least 70% sequence identity or homology to any one of the amino acid sequences set forth in any of SEQ ID NOs: 8-13.

Embodiment 27. The method of any one of embodiments 1-26, wherein an intermediate (in forming the at least one product) with a terminal aldehyde group is formed by a carboxylate reductase and enhanced by a phosphopantetheinyl transferase.

Embodiment 28. The method of embodiment 27, wherein said carboxylate reductase has at least 70% sequence identity or homology to any one of the amino acid sequences set forth in any of SEQ ID NOs: 2-7.

Embodiment 29. The method of any of the preceding embodiments, wherein said method is performed in a recombinant host by fermentation.

Embodiment 30. The method of embodiment 29, wherein said recombinant host is subjected to a cultivation condition under aerobic, anaerobic, micro-aerobic or mixed oxygen/denitrification cultivation conditions.

Embodiment 31. The method of embodiment 29 or embodiment 30, wherein said recombinant host is cultured under conditions of nutrient limitation.

Embodiment 32. The method according to any one of embodiments 29-31, wherein said recombinant host is retained using a ceramic hollow fiber membrane to maintain a high cell density during fermentation.

Embodiment 33. The method of any one of embodiments 29-32, wherein the principal carbon source fed to the fermentation derives from biological or non-biological feedstocks.

Embodiment 34. The method of embodiment 33, wherein the biological feedstock is, or derives from, at least one chosen from monosaccharides, disaccharides, lignocellulose, hemicellulose, cellulose, lignin, levulinic acid, formic acid, triglycerides, glycerol, fatty acids, agricultural waste, condensed distillers' solubles, or municipal waste.

Embodiment 35. The method of embodiment 33, wherein the non-biological feedstock is, or derives from, at least one chosen from natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

Embodiment 36. The method of any one of embodiments 29-35, wherein the recombinant host is a prokaryote.

Embodiment 37. The method of embodiment 36, wherein said prokaryote is chosen from the genii *Escherichia, Clostridia, Corynebacteria, Cupriavidus, Pseudomonas, Delftia acidovorans, Bacillus, Lactobacillus, Lactococcus,* or *Rhodococcus.*

Embodiment 38. The method of embodiment 37, wherein said prokaryote is *Escherichia coli.*

Embodiment 39. The method of embodiment 37, wherein said prokaryote is *Clostridium ljungdahlii, Clostridium autoethanogenum,* or *Clostridium kluyveri.*

Embodiment 40. The method of embodiment 37, wherein said prokaryote is *Corynebacterium glutamicum.*

Embodiment 41. The method of embodiment 37, wherein said prokaryote is *Cupriavidus necator* or *Cupriavidus metallidurans.*

Embodiment 42. The method of embodiment 37, wherein said prokaryote is *Pseudomonas fluorescens, Pseudomonas putida* or *Pseudomonas oleavorans.*

Embodiment 43. The method of embodiment 37, wherein said prokaryote is *Bacillus subtillis.*

Embodiment 44. The method of embodiment 37, wherein said prokaryote is *Lactobacillus delbrueckii.*

Embodiment 45. The method of embodiment 37, wherein said prokaryote is *Lactococcus lactis.*

Embodiment 46. The method of embodiment 37, wherein said prokaryote is *Rhodococcus equi.*

Embodiment 47. The method of any one of embodiments 29-35, wherein the host is a eukaryote.

Embodiment 48. The method of embodiment 47, wherein said eukaryote is from the genii *Aspergillus, Saccharomyces, Pichia, Yarrowia, Issatchenkia, Debaryomyces, Arxula,* or *Kluyveromyces.*

Embodiment 49. The method of embodiment 47, wherein said eukaryote is *Aspergillus niger.*

Embodiment 50. The method of embodiment 47, wherein said eukaryote is *Saccharomyces cerevisiae.*

Embodiment 51. The method of embodiment 47, wherein said eukaryote is *Pichia pastoris.*

Embodiment 52. The method of embodiment 47, wherein said eukaryote is *Yarrowia lipolytica.*

Embodiment 53. The method of embodiment 47, wherein said eukaryote is *Issathenkia orientalis.*

Embodiment 54. The method of embodiment 47, wherein said eukaryote is *Debaryomyces hansenii.*

Embodiment 55. The method of embodiment 47, wherein said eukaryote is *Arxula adenoinivorans.*

Embodiment 56. The method of embodiment 47, wherein said eukaryote is *Kluyveromyces lactis.*

Embodiment 57. The method of embodiment 29, wherein the recombinant host's tolerance to high concentrations of at least one C7 building block is improved through continuous cultivation in a selective environment.

Embodiment 58. The method of any one of embodiments 29-57, wherein said recombinant host comprises one or more of attenuated enzymes chosen from polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the NADH or NADPH imbalance, an glutamate dehydrogenase dissipating the NADH or NADPH imbalance, a NADH/NADPH-utilizing glutamate dehydrogenase, a pimeloyl-CoA dehydrogenase; an acyl-CoA dehydrogenase accepting C7 building blocks and central precursors as substrates; a glutaryl-CoA dehydrogenase; or a pimeloyl-CoA synthetase.

Embodiment 59. The method of any one of embodiments 29-58, wherein said recombinant host overexpresses one or more genes encoding an acetyl-CoA synthetase, a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a L-alanine dehydrogenase; a L-glutamate dehydrogenase specific to the NADH or NADPH used to generate a co-factor imbalance; a methanol dehydrogenase, a formaldehyde dehydrogenase, a diamine transporter; a dicarboxylate transporter; an S-adenosylmethionine synthetase and/or a multidrug transporter.

Embodiment 60. A recombinant host for producing for pimeloyl-ACP, said recombinant host comprising a deletion of a bioF gene.

Embodiment 61. A recombinant host for producing for pimeloyl-ACP, wherein said recombinant host expresses a BioF at a level below that of a wild type host.

Embodiment 62. The recombinant host of embodiment 1, wherein said recombinant host does not express BioF activity.

Embodiment 63. The recombinant host of embodiment [47], wherein said recombinant host comprises at least one exogenous nucleic acid encoding bioW and a CoA-specific bioF.

Embodiment 64. A non-naturally occurring organism comprising at least one exogenous nucleic acid encoding at least one polypeptide having the activity of at least one enzyme depicted in any one of FIGS. 1 to 21.

Embodiment 65. A nucleic acid construct or expression vector comprising a polynucleotide encoding a polypeptide having 8-amino-7-oxononanoate synthase activity, wherein the polynucleotide is operably linked to one or more heterologous control sequences that direct production of the polypeptide and wherein the polypeptide having 8-amino-7-oxononanoate synthase activity is a polypeptide having at least 70% sequence identity or homology to the polypeptide of SEQ ID NO: 23.

Embodiment 66. A nucleic acid construct or expression vector comprising a polynucleotide encoding a polypeptide having thioesterase activity, wherein the polynucleotide is operably linked to one or more heterologous control sequences that direct production of the polypeptide and wherein the polypeptide having thioesterase activity is selected from the group consisting of: (a) a polypeptide having at least 70% sequence identity or homology to the polypeptide of SEQ ID NO: 1; (b) a polypeptide having at least 70% sequence identity or homology to the polypeptide of SEQ ID NO: 21; and (c) a polypeptide having at least 70% sequence identity or homology to the polypeptide of SEQ ID NO: 22.

Embodiment 67. A nucleic acid construct or expression vector comprising a polynucleotide encoding a polypeptide having carboxylate reductase activity, wherein the polynucleotide is operably linked to one or more heterologous control sequences that direct production of the polypeptide and wherein the polypeptide having carboxylate reductase activity is selected from the group consisting of: (a) a polypeptide having at least 70% sequence identity or homology to the polypeptide of SEQ ID NO: 2; (b) a polypeptide having at least 70% sequence identity or homology to the polypeptide of SEQ ID NO: 3; (c) a polypeptide having at least 70% sequence identity or homology to the polypeptide of SEQ ID NO: 4; (d) a polypeptide having at least 70% sequence identity or homology to the polypeptide of SEQ ID NO: 5; (e) a polypeptide having at least 70% sequence identity or homology to the polypeptide of SEQ ID NO: 6; and (f) a polypeptide having at least 70% sequence identity or homology to the polypeptide of SEQ ID NO: 7.

Embodiment 68. A nucleic acid construct or expression vector comprising a polynucleotide encoding a polypeptide having ω-transaminase activity, wherein the polynucleotide is operably linked to one or more heterologous control sequences that direct production of the polypeptide and wherein the polypeptide having ω-transaminase activity is selected from the group consisting of: (a) a polypeptide having at least 70% sequence identity or homology to the polypeptide of SEQ ID NO: 8; (b) a polypeptide having at least 70% sequence identity or homology to the polypeptide of SEQ ID NO: 9; (c) a polypeptide having at least 70% sequence identity or homology to the polypeptide of SEQ ID NO: 10 (d) a polypeptide having at least 70% sequence identity or homology to the polypeptide of SEQ ID NO: 11; (e) a polypeptide having at least 70% sequence identity or homology to the polypeptide of SEQ ID NO: 12; and (f) a polypeptide having at least 70% sequence identity or homology to the polypeptide of SEQ ID NO: 13.

Embodiment 69. A nucleic acid construct or expression vector comprising a polynucleotide encoding a polypeptide having phosphopantetheinyl transferase activity, wherein the polynucleotide is operably linked to one or more heterologous control sequences that direct production of the polypeptide and wherein the polypeptide having phosphopantetheinyl transferase activity is selected from the group consisting of: (a) a polypeptide having at least 70% sequence identity or homology to the polypeptide of SEQ ID NO: 14 and (b) a polypeptide having at least 70% sequence identity or homology to the polypeptide of SEQ ID NO: 15.

Embodiment 70. A nucleic acid construct or expression vector comprising a polynucleotide encoding a polypeptide having pimeloyl-ACP methyl ester esterase activity, wherein the polynucleotide is operably linked to one or more heterologous control sequences that direct production of the polypeptide and wherein the polypeptide having pimeloyl-ACP methyl ester esterase activity is a polypeptide having at least 70% sequence identity or homology to the polypeptide of SEQ ID NO: 17.

Embodiment 71. A nucleic acid construct or expression vector comprising a polynucleotide encoding a polypeptide having 6-carboxyhexanoate-CoA ligase activity, wherein the polynucleotide is operably linked to one or more heterologous control sequences that direct production of the polypeptide and wherein the polypeptide having 6-carboxyhexanoate-CoA ligase activity is a polypeptide having at least 70% sequence identity or homology to the polypeptide of SEQ ID NO: 18.

Embodiment 72. A nucleic acid construct or expression vector comprising a polynucleotide encoding a polypeptide having 8-amino-7-oxononanoate synthase activity, wherein the polynucleotide is operably linked to one or more heterologous control sequences that direct production of the polypeptide and wherein the polypeptide having 8-amino-7-oxononanoate synthase activity is a polypeptide having at least 70% sequence identity or homology to the polypeptide of SEQ ID NO: 19.

Embodiment 73. A nucleic acid construct or expression vector comprising a polynucleotide encoding a polypeptide having malonyl-ACP O-methyltransferase activity, wherein the polynucleotide is operably linked to one or more heterologous control sequences that direct production of the polypeptide and wherein the polypeptide having malonyl-ACP O-methyltransferase activity is a polypeptide having at least 70% sequence identity or homology to the polypeptide of SEQ ID NO: 20.

Embodiment 74. A composition comprising the nucleic acid construct or expression vector of any one of embodiments 65-73.

Embodiment 75. A non-naturally occurring biochemical network comprising a 5-hydroxypentanoyl-CoA, an exogenous nucleic acid encoding a polypeptide having the activity of a β-ketothiolase classified under EC. 2.3.1, and a 3-oxo-7-hydroxyheptanoyl-CoA.

Embodiment 76. A bio-derived, bio-based or fermentation-derived product, wherein said product comprises:
  i. a composition comprising at least one bio-derived, bio-based or fermentation-derived compound produced or biosynthesized according to any one of embodiments 1-75 or any one of FIGS. 1-21, or any combination thereof;
  ii. a bio-derived, bio-based or fermentation-derived polymer comprising the bio-derived, bio-based or fermentation-derived composition or compound of i., or any combination thereof;
  iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof;
  iv. a molded substance obtained by molding the bio-derived, bio-based or fermentation-derived polymer of ii. or the bio-derived, bio-based or fermentation-derived resin of iii., or any combination thereof;
  v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of bio-derived, bio-based or fermentation-derived resin of iii., or bio-derived, bio-based or fermentation-derived molded substance of iv, or any combination thereof; or
  vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the disclosure are set forth in the accompanying drawings and the description below. Other features, objects, and advantages of the disclosure will be apparent from the description and the drawings, and from the claims. The word "comprising" in the claims may be replaced by "consisting essentially of" or with "consisting of," according to standard practice in patent law.

BRIEF DESCRIPTION OF DRAWING(S)

FIG. 1 illustrates an exemplary biotin biosynthesis in *E. coli* through intermediates 8-amino-7-oxononanoate (KAPA) and 7,8-diaminopelargonic acid (DAPA), and the regulation of the biosynthesis to divert pimelic acid for 7-AHA production.

FIGS. 9A-9D contain the amino acid sequences of an *Escherichia coli* thioesterase encoded by tesB (see GenBank Accession No. AAA24665.1, SEQ ID NO: 1), a *Mycobacterium marinum* carboxylate reductase (see Genbank Accession No. ACC40567.1, SEQ ID NO: 2), a *Mycobacterium smegmatis* carboxylate reductase (see Genbank Accession No. ABK71854.1, SEQ ID NO: 3), a *Segnihparus rugosus* carboxylate reductase (see Genbank Accession No. EFV11917.1, SEQ ID NO: 4), a *Mycobacterium smegmatis* carboxylate reductase (see Genbank Accession No. ABK75684.1, SEQ ID NO: 5), a *Mycobacterium massiliense* carboxylate reductase (see Genbank Accession No. EIV11143.1, SEQ ID NO: 6), a *Segnihparus rotundus* carboxylate reductase (see Genbank Accession No. ADG98140.1, SEQ ID NO: 7), a *Chromobacterium violaceum* ω-transaminase (see Genbank Accession No. AAQ59697.1, SEQ ID NO: 8), a *Pseudomonas aeruginosa* ω-transaminase (see Genbank Accession No. AAG08191.1, SEQ ID NO: 9), a *Pseudomonas syringae* ω-transaminase (see Genbank Accession No. AAY39893.1, SEQ ID NO: 10), a *Rhodobacter sphaeroides* ω-transaminase (see Genbank Accession No. ABA81135.1, SEQ ID NO: 11), an *Escherichia coli* ω-transaminase (see RefSeq Accession No.

NP 417544.5, SEQ ID NO: 12), a *Vibrio fluvialis* ω-transaminase (see Genbank Accession No. AEA39183.1, SEQ ID NO: 13), a *Bacillus subtilis* phosphopantetheinyl transferase (see RefSeq Accession No. WP 003234549.1, SEQ ID NO:14), a *Nocardia* sp. NRRL 5646 phosphopantetheinyl transferase (see Genbank Accession No. ABI83656.1, SEQ ID NO:15), a *Bacillus cereus* malonyl-CoA methyltransferase (see GenBank Accession No. AAS43086.1, SEQ ID NO: 16), an *Escherichia coli* pimelyl-ACP methyl ester esterase (see GenBank Accession No. AAC76437.1, SEQ ID NO:17), a 6-carboxyhexanoate-CoA ligase (BioW) (EC:6.2.1.14, see GenBank Accession No. AAB17457.1, SEQ ID NO:18), a 8-amino-7-oxononanoate synthase (BioF) (EC:2.3.1.47, see GenBank Accession No. AAB17459.1, SEQ ID NO: 19), a SAM-dependent malonyl-ACP O-methyltransferas (BioC) (EC:2.1.1.197, see RefSeq Accession No. NP 415298.1, SEQ ID NO:20), a thioesterase encoded by tesA orfatB (see GenBank Accession No. ABJ63754.1, SEQ ID NO:21; see GenBank Accession No. CCC78182.1, SEQ ID NO:22), and a 8-amino-7-oxononanoate synthase (BioF, or ACP-dependent BioF) (EC: 2.3.1.47, see GenBank Accession No. AAA23516.1, SEQ ID NO: 23).

Figure 10:
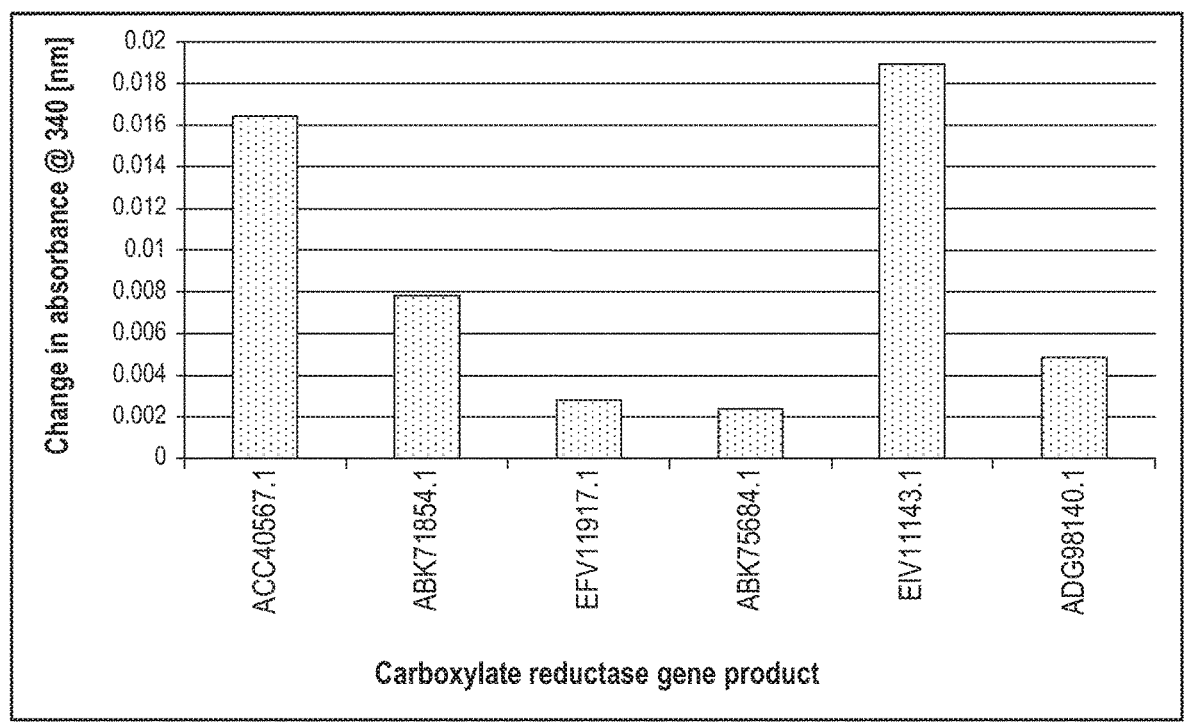

FIG. 10 is a bar graph summarizing the change in absorbance at 340 nm after 20 minutes, which is a measure of the consumption of NADPH and activity of carboxylate reductases relative to the enzyme only controls (no substrate).

Figure 11:
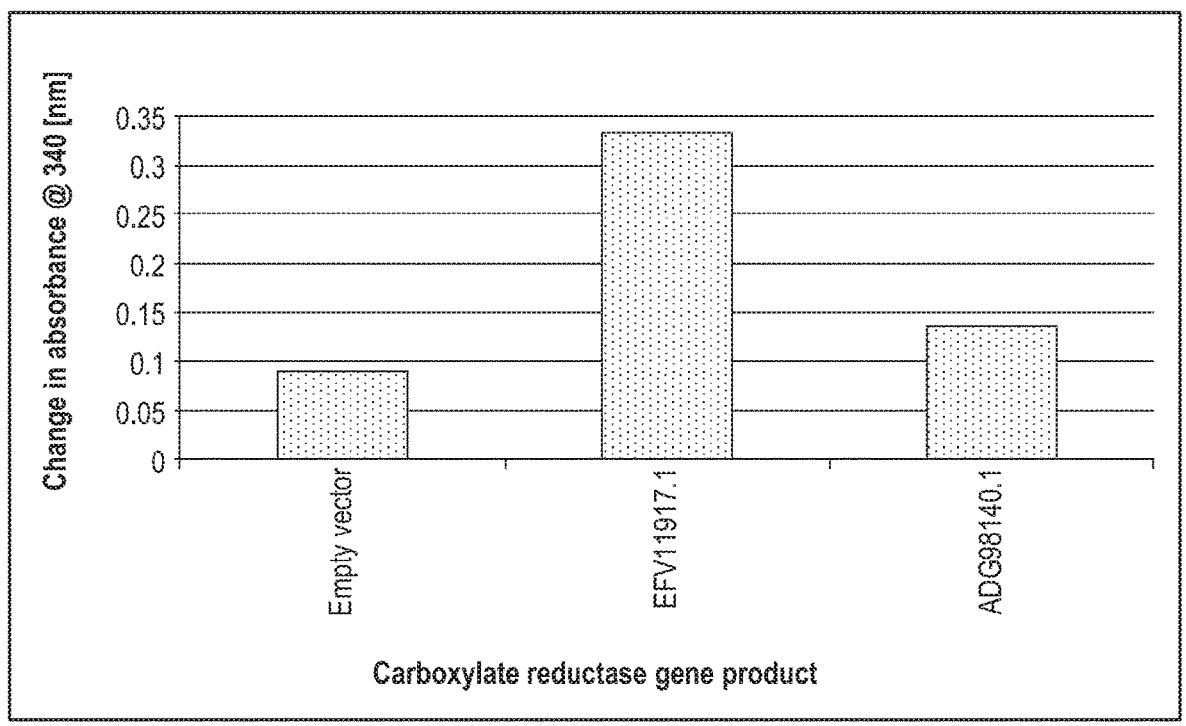

FIG. 11 is a bar graph of the change in absorbance at 340 nm after 20 minutes, which is a measure of the consumption of NADPH and the activity of carboxylate reductases for converting pimelate to pimelate semialdehyde relative to the empty vector control.

Figure 12:
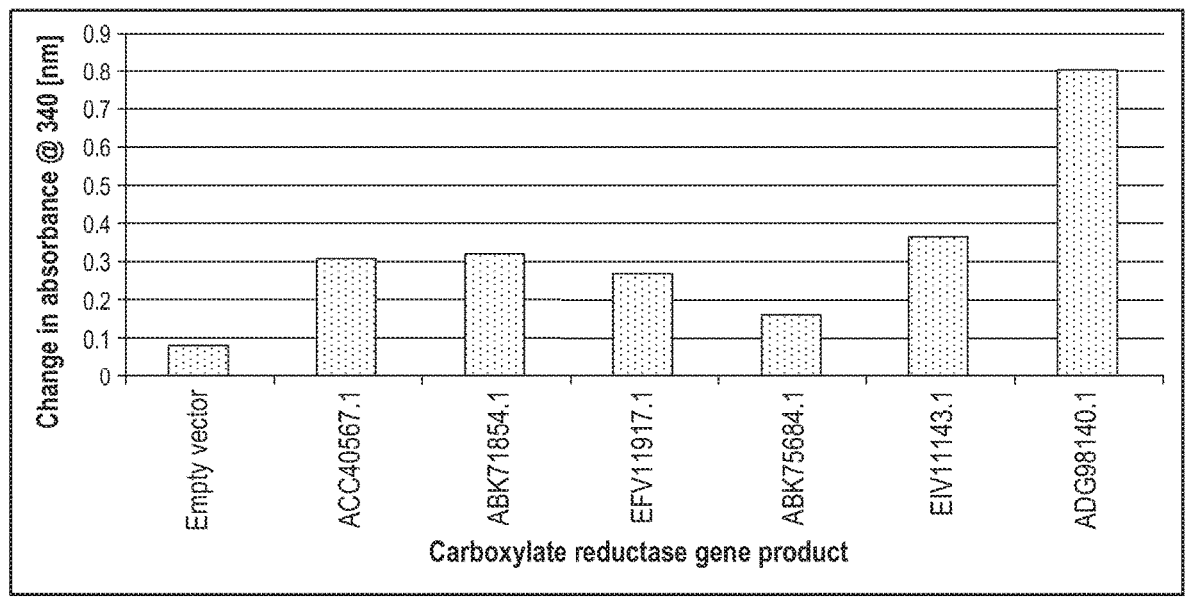

FIG. 12 is a bar graph of the change in absorbance at 340 nm after 20 minutes, which is a measure of the consumption of NADPH and the activity of carboxylate reductases for converting 7-hydroxyheptanoate to 7-hydroxyheptanal relative to the empty vector control.

Figure 13:
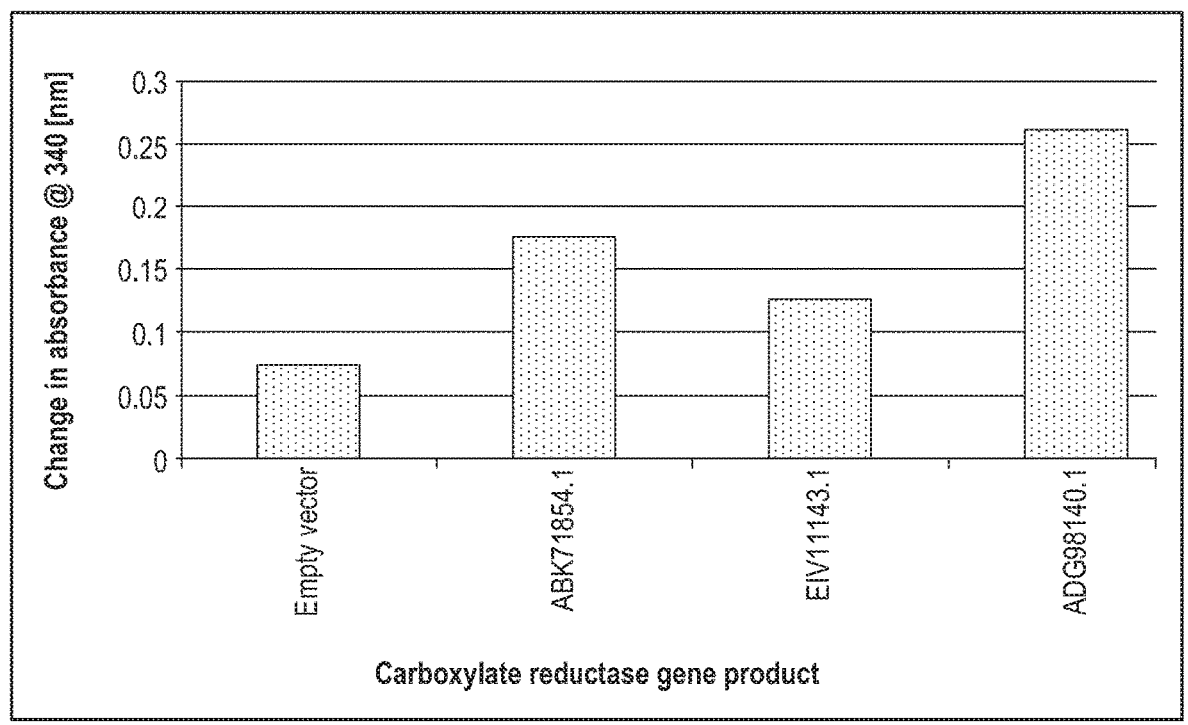

FIG. 13 is a bar graph of the change in absorbance at 340 nm after 20 minutes, which is a measure of the consumption of NADPH and the activity of carboxylate reductases for converting N7-acetyl-7-aminoheptanoate to N7-acetyl-7-aminoheptanal relative to the empty vector control.

Figure 14:
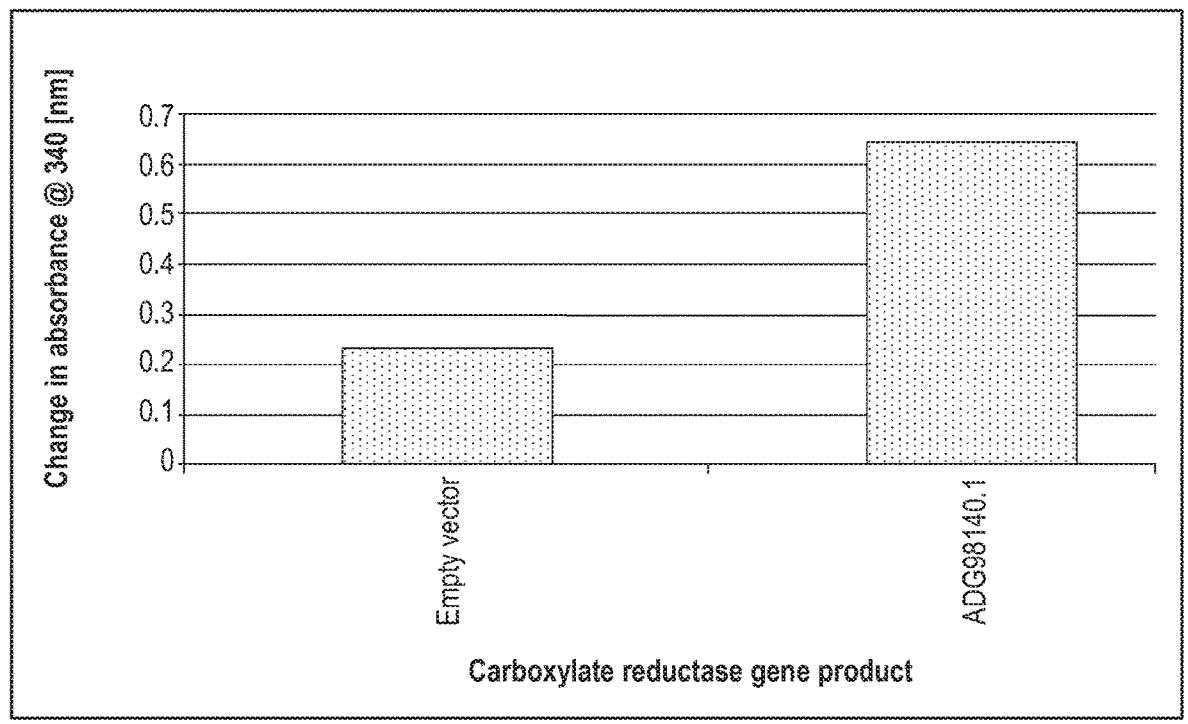

FIG. 14 is a bar graph of the change in absorbance at 340 nm after 20 minutes, which is a measure of the consumption of NADPH and activity of carboxylate reductases for converting pimelate semialdehyde to heptanedial relative to the empty vector control.

Figure 15:
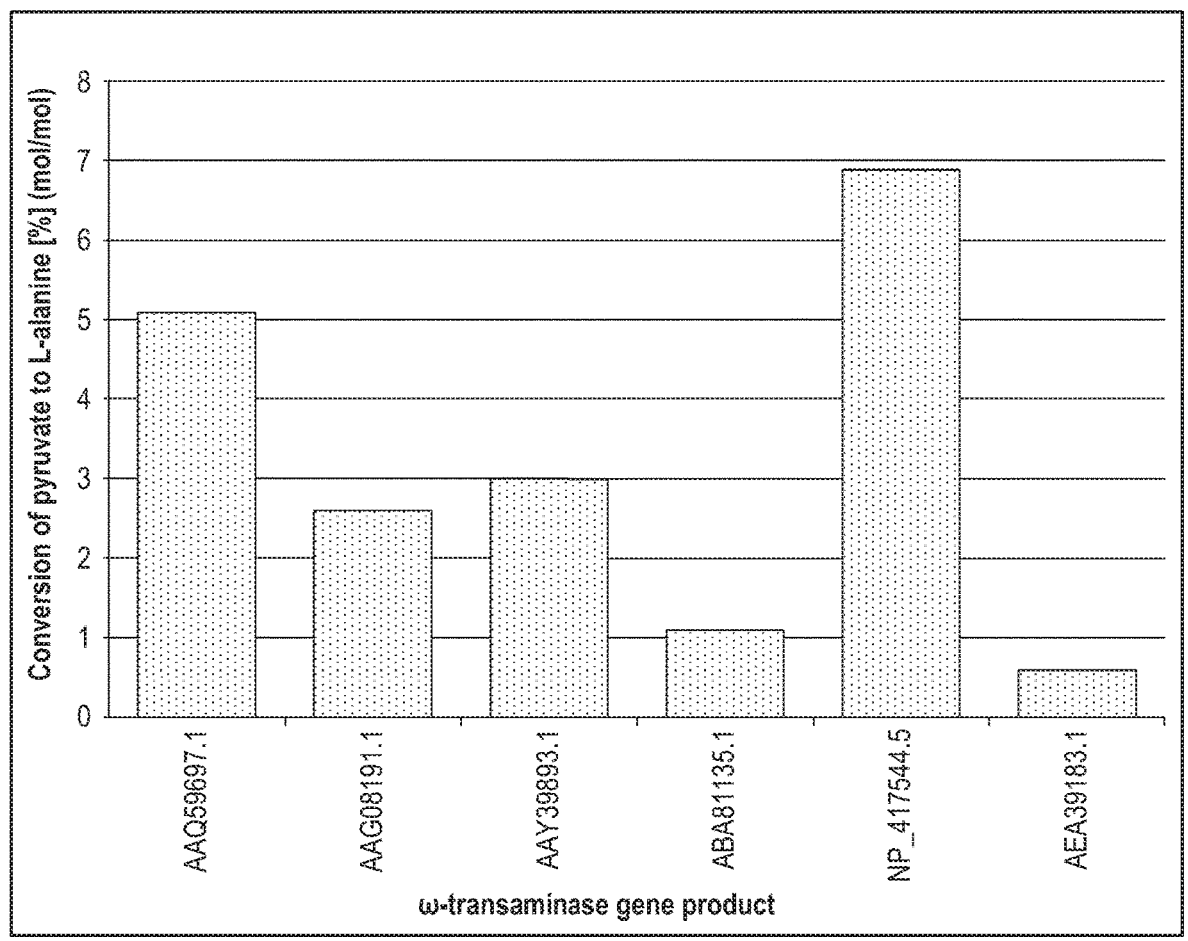

FIG. 15 is a bar graph summarizing the percent conversion after 4 hours of pyruvate to L-alanine (mol/mol) as a measure of the ω-transaminase activity of the enzyme only controls (no substrate).

Figure 16:
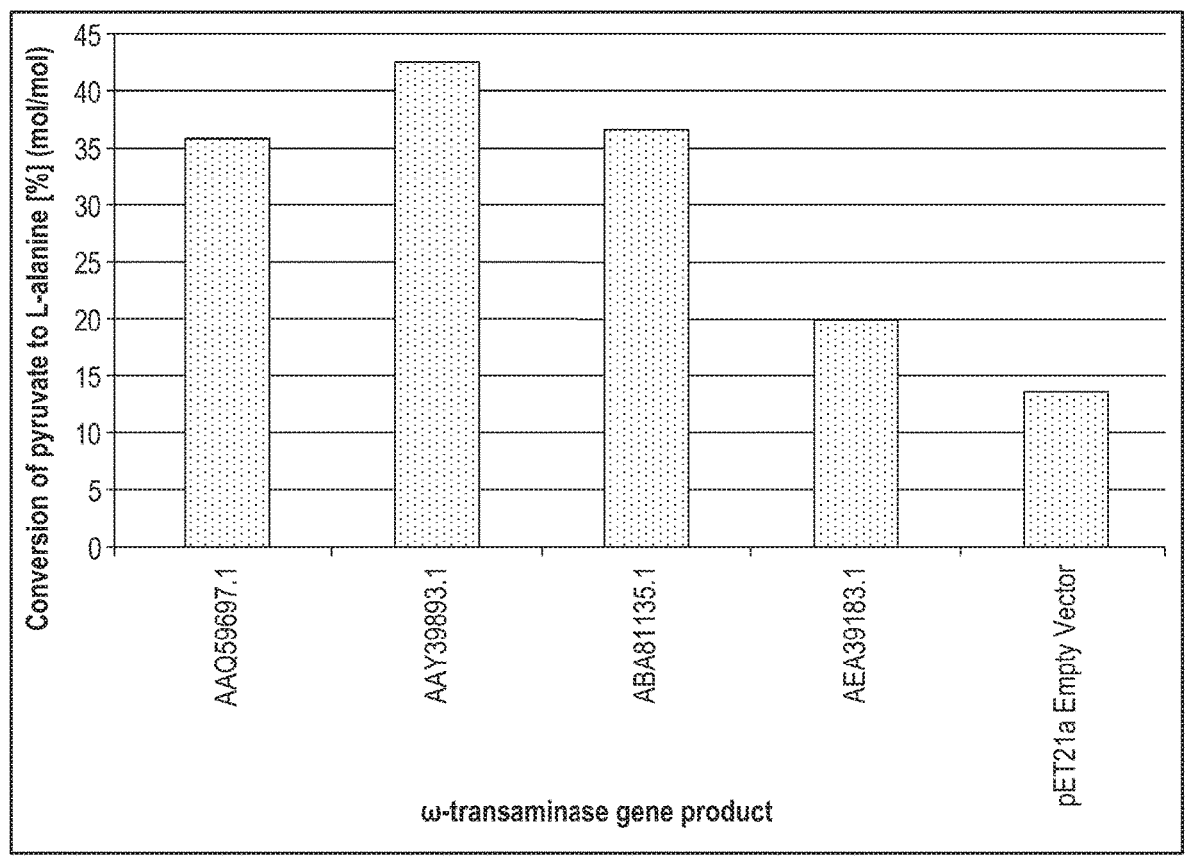

FIG. 16 is a bar graph of the percent conversion after 4 hours of pyruvate to L-alanine (mol/mol) as a measure of the ω-transaminase activity for converting 7-aminoheptanoate to pimelate semialdehyde relative to the empty vector control.

Figure 17:
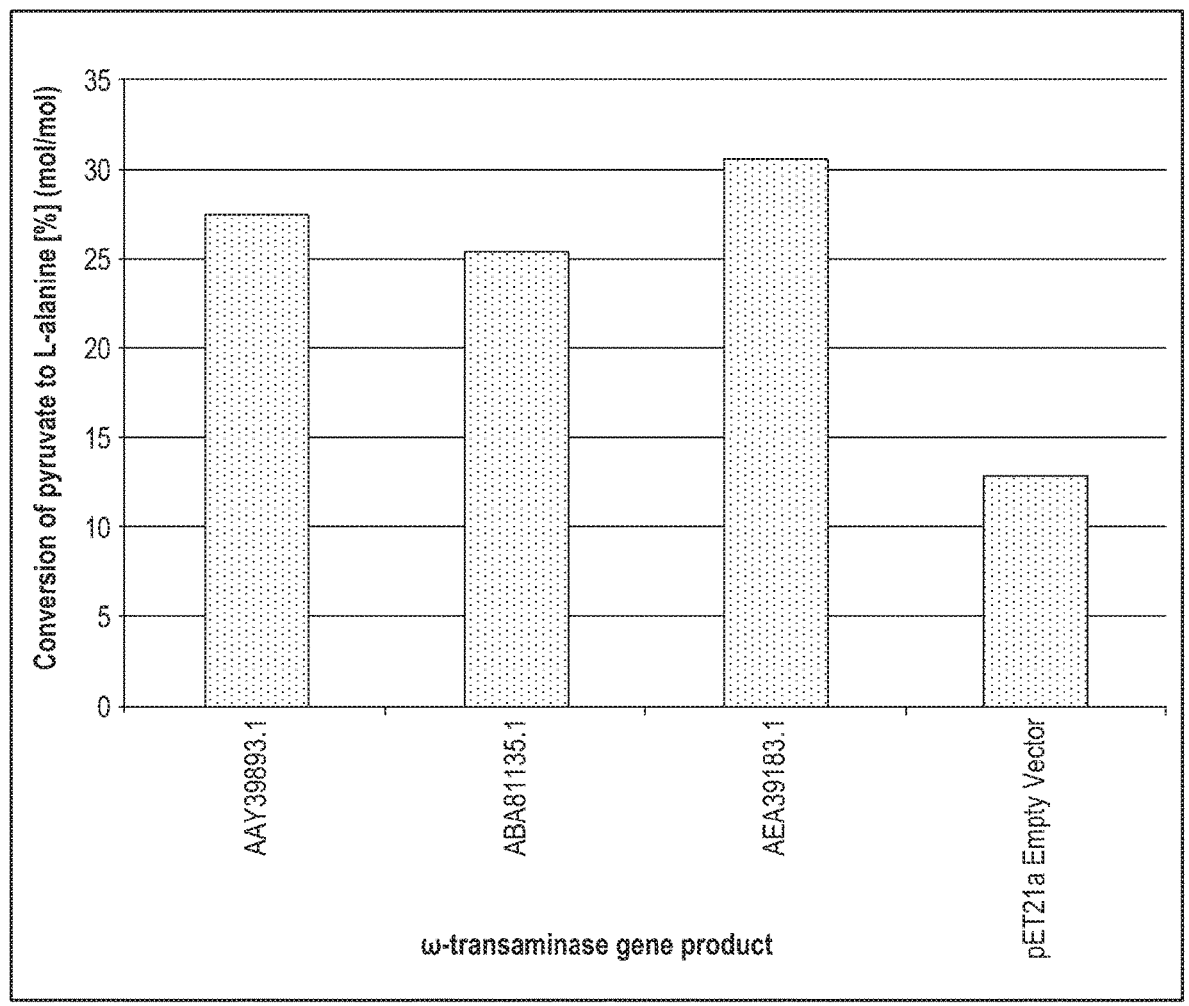

FIG. 17 is a bar graph of the percent conversion after 4 hours of L-alanine to pyruvate (mol/mol) as a measure of the ω-transaminase activity for converting pimelate semialdehyde to 7-aminoheptanoate relative to the empty vector control.

Figure 18:
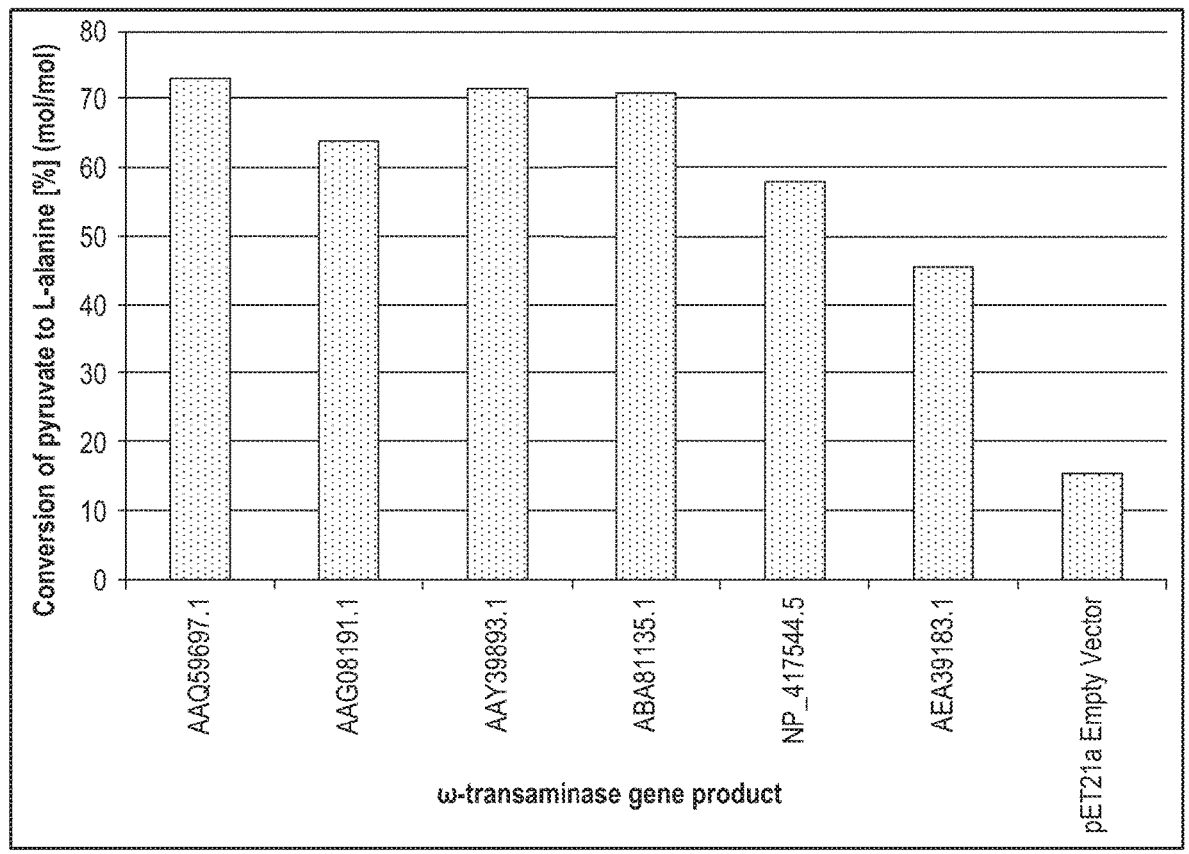

FIG. 18 is a bar graph of the percent conversion after 4 hours of pyruvate to L-alanine (mol/mol) as a measure of the ω-transaminase activity for converting heptamethylenediamine to 7-aminoheptanal relative to the empty vector control.

Figure 19:
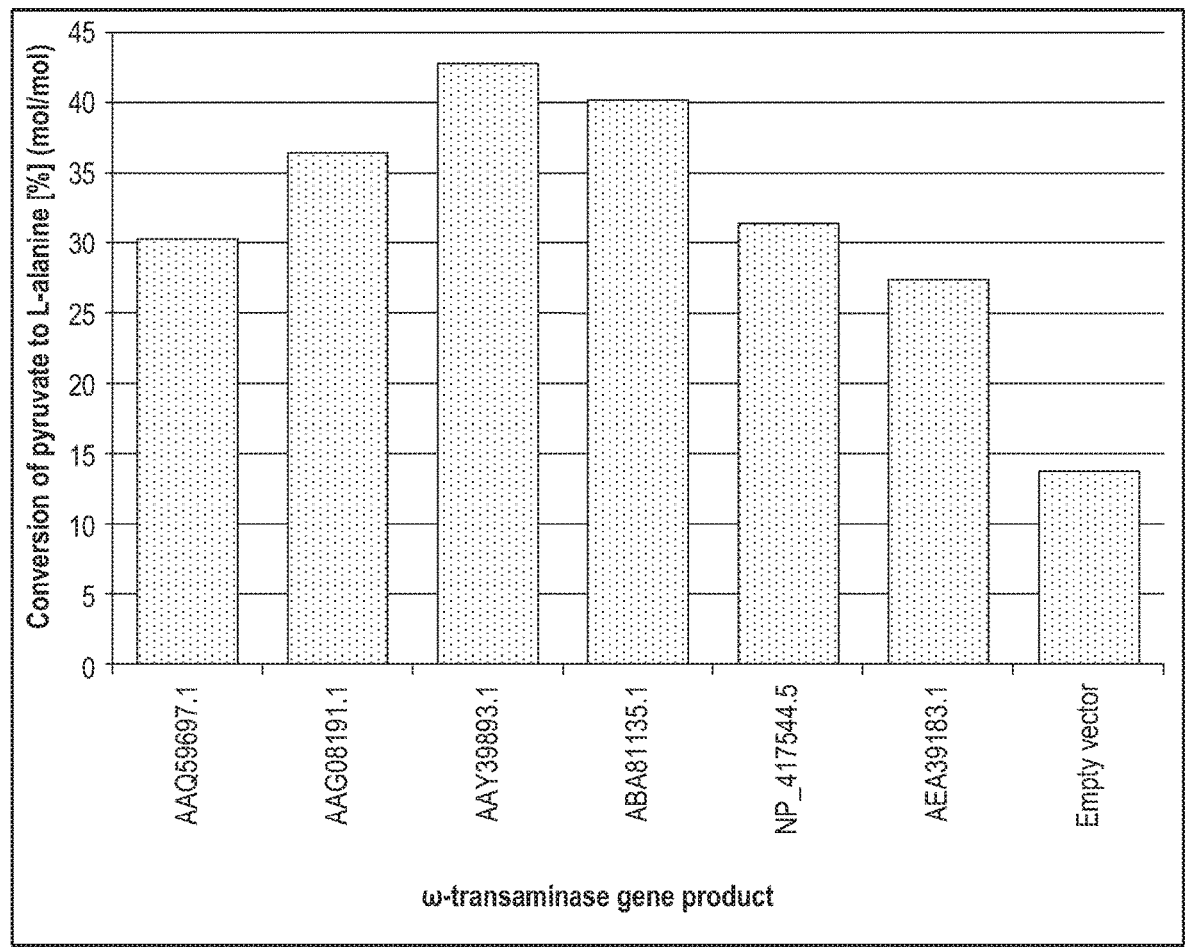

FIG. 19 is a bar graph of the percent conversion after 4 hours of pyruvate to L-alanine (mol/mol) as a measure of the ω-transaminase activity for converting N7-acetyl-1,7-diaminoheptane to N7-acetyl-7-aminoheptanal relative to the empty vector control.

Figure 20:
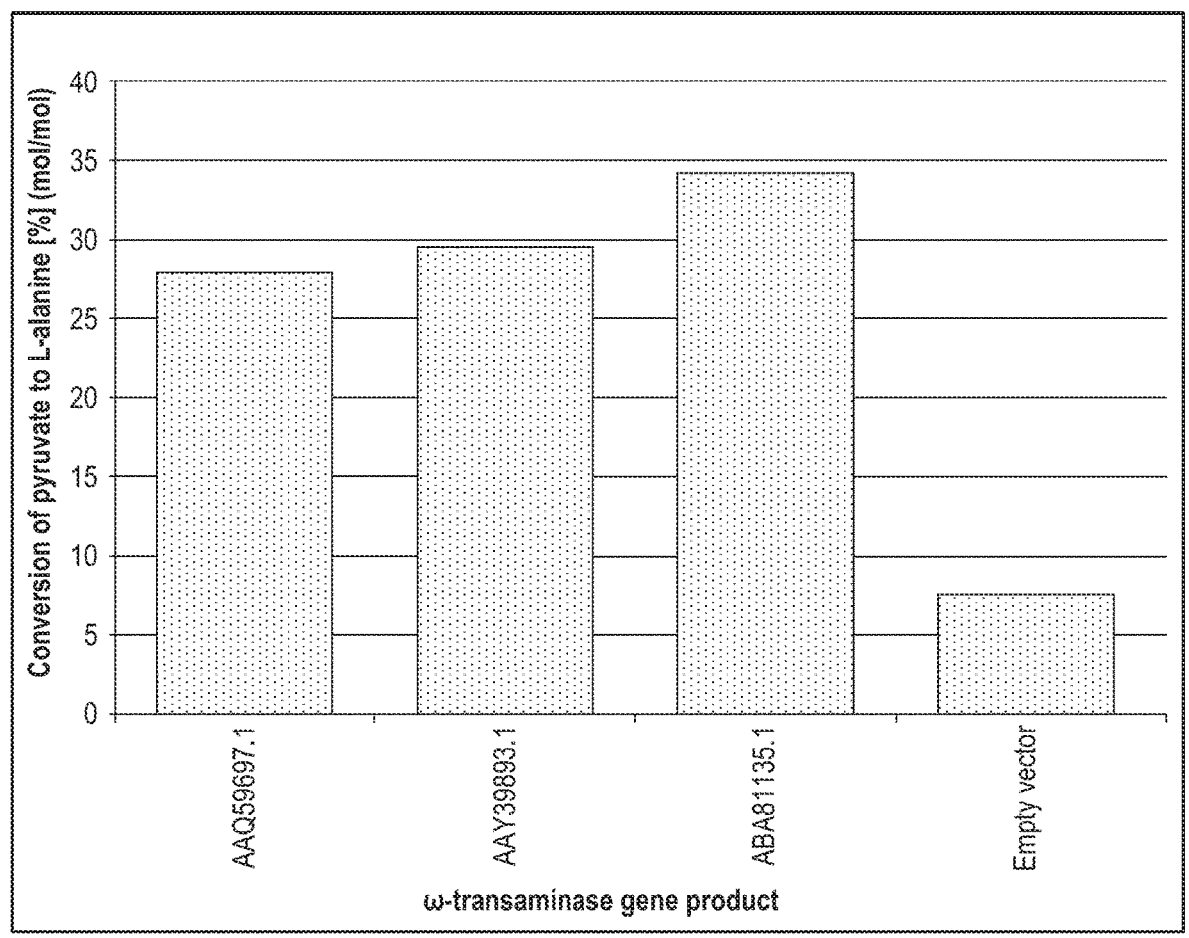

FIG. 20 is a bar graph of the percent conversion after 4 hours of pyruvate to L-alanine (mol/mol) as a measure of the ω-transaminase activity for converting 7-aminoheptanol to 7-oxoheptanol relative to the empty vector control.

FIG. 21 is a table of the conversion after 1 hour of pimeloyl-CoA methyl ester to pimeloyl-CoA by a pimeloyl-[acp] methyl ester methylesterase.

DETAILED DESCRIPTION

This disclosure provides enzymes, non-natural pathways, cultivation strategies, feedstocks, host microorganisms and attenuations to the host's biochemical network, which generates a C7 aliphatic backbone from central metabolites in which two terminal functional groups may be formed leading to the synthesis of pimelic acid, 7-aminoheptanoic acid, heptamethylenediamine, 7-aminoheptanol or 1,7-heptanediol (referred to as "C7 building blocks" herein). As used herein, the term "central precursor" is used to denote any metabolite in any metabolic pathway shown herein leading to the synthesis of a C7 building block. The term "central metabolite" is used herein to denote a metabolite that is produced in all microorganisms to support growth.

The term "bioF" refers to any one of a number of bioF genes well known in the art and present in multiple organisms. The term "BioF" refers to a protein encoded by any one of such genes. Numerous bioF genes and BioF proteins from different organisms are well known in the art and can be easily identified in public databases such as GenBank, ExPASy, and via Enzyme Commission numbers.

Host microorganisms described herein can include endogenous pathways that can be manipulated such that one or more C7 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host in addition to a malonyl-ACP O-methyltransferase; a β-ketoacyl-[acp] synthase, a β-ketothiolase, a 3-oxoacyl-[acp] reductase, acetoacetyl-CoA reductase, a 3-hydroxyacyl-CoA dehydrogenase, a 3-hydroxybutyryl-CoA dehydrogenase, an enoyl-CoA hydratase, 3-hydroxyacyl-ACP dehydratase, an enoyl-ACP reductase, a trans-2-enoyl-CoA reductase, a thioesterase, a reversible CoA ligase, a CoA-transferase, an acetylating aldehyde dehydrogenase, a 6-oxohexanoate dehydrogenase, a 7-oxoheptanoate dehydrogenase, an aldehyde dehydrogenase, a carboxylate reductase, a ω-transaminase, a N-acetyl transferase, an alcohol dehydrogenase, a deacetylase, a 6-hydroxyhexanoate dehydrogenase, a 5-hydroxypentanoate dehydrogenase, or a 4-hydroxybutyrate dehydrogenase. In recombinant hosts expressing a carboxylate reductase, a phosphopantetheinyl transferase also can be expressed as it enhances activity of the carboxylate reductase.

For example, a recombinant host can include at least one exogenous nucleic acid encoding (i) a malonyl-ACP O-methyltransferase, (ii) a 3-ketoacyl-ACP synthase or a β-ketothiolase, (iii) a 3-oxoacyl-ACP reductase, acetoacetyl-CoA reductase, a 3-hydroxyacyl-CoA dehydrogenase or a 3-hydroxybutyryl-CoA dehydrogenase, (iv) an enoyl-CoA hydratase or 3-hydroxyacyl-ACP dehydratase, (v) an enoyl-ACP reductase or a trans-2-enoyl-CoA reductase and produce pimeloyl-ACP or pimeloyl-CoA.

Such recombinant hosts producing pimeloyl-ACP or pimeloyl-CoA further can include at least one exogenous nucleic acid encoding one or more of a thioesterase, an aldehyde dehydrogenase, a 7-oxoheptanoate dehydrogenase, a 6-oxohexanoate dehydrogenase, a glutaconate CoA-transferase, a reversible succinyl-CoA ligase, an acetylating aldehyde dehydrogenase, or a carboxylate reductase and produce pimelic acid or pimelate semialdehyde. For example, a recombinant host producing pimeloyl-ACP or pimeloyl-CoA further can include a thioesterase, a reversible Co-ligase (e.g., a reversible succinyl-CoA ligase), or a CoA transferase (e.g., a glutaconate CoA-transferase) and produce pimelic acid. For example, a recombinant host producing pimeloyl-CoA further can include an acetylating aldehyde dehydrogenase and produce pimelate semialdehyde.

For example, a recombinant host producing pimelate further can include a carboxylate reductase and produce pimelate semialdehyde.

In some embodiments, the recombinant host can comprise at least one exogenous nucleic acid encoding bioW and a CoA-specific bioF.

A recombinant host producing pimelate semialdehyde further can include at least one exogenous nucleic acid encoding a ω-transaminase and produce 7-aminoheptanoate.

In some embodiments, a recombinant host producing pimeloyl-CoA includes a carboxylate reductase and a ω-transaminase to produce 7-aminoheptanoate.

A recombinant host producing pimelate or pimelate semialdehyde further can include at least one exogenous nucleic acid encoding a 6-hydroxyhexanoate dehydrogenase, a 5-hydroxypentanoate dehydrogenase or a 4-hydroxybutyrate dehydrogenase, and produce 7-hydroxyheptanoic acid. In some embodiments, a recombinant host producing pimeloyl-CoA includes an acetylating aldehyde dehydrogenase, and a 6-hydroxyhexanoate dehydrogenase, a 5-hydroxypentanoate dehydrogenase or a 4-hydroxybutyrate dehydrogenase to produce 7-hydroxyheptanoate. In some embodiments, a recombinant host producing pimelate includes a carboxylate reductase and a 6-hydroxyhexanoate dehydrogenase, a 5-hydroxypentanoate dehydrogenase or a 4-hydroxybutyrate dehydrogenase to produce 7-hydroxyheptanoate.

A recombinant host producing 7-aminoheptanoate, 7-hydroxyheptanoate or pimelate semialdehyde further can include at least one exogenous nucleic acid encoding a ω-transaminase, a deacetylase, a N-acetyl transferase, or an alcohol dehydrogenase, and produce heptamethylenediamine. For example, a recombinant host producing 7-hydroxyheptanoate can include a carboxylate reductase with a phosphopantetheine transferase enhancer, a ω-transaminase and an alcohol dehydrogenase.

A recombinant host producing 7-hydroxyheptanoic acid further can include one or more of a carboxylate reductase with a phosphopantetheine transferase enhancer and an alcohol dehydrogenase, and produce 1,7-heptanediol.

Within an engineered pathway, the enzymes can be from a single source, i.e., from one species or genus, or can be from multiple sources, i.e., different species or genera. Nucleic acids encoding the enzymes described herein have been identified from various organisms and are readily available in publicly available databases such as GenBank or EMBL.

Any of the enzymes described herein that can be used for production of one or more C7 building blocks can have at least 50%, 60% or 70% sequence identity or homology (e.g., at least 50%, 55%, 60%, 65%, 70%, 75%, 80%, 85%, 90%, 95%, 97%, 98%, 99%, or 100%) to the amino acid sequence of the corresponding wild-type enzyme. It will be appreciated that the sequence identity can be determined on the basis of the mature enzyme (e.g., with any signal sequence removed).

The percent identity and homology between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from www.fr.com/blast/ or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length polypeptide amino acid sequence followed by multiplying the resulting value by 100. It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution and this process results in "sequence homology" of, e.g., at least 75%, 80%, 85%, 90%, 91%, 92%, 93%, 94%, 95%, 96%, 97%, 98%, or 99%. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer. Applic. Biol. Sci., 1988, 4, 11-17, e.g., as implemented in the program PC/GENE (Intelligenetics, Mountain View, Cailf., USA). This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Such programs may include the GCG Pileup program, FASTA (Pearson et al., Proc. Natl. Acad. Sci. USA, 1988, 85, 2444-2448), and BLAST (BLAST Manual, Altschul et al., Nat'l Cent. Biotechnol. Inf., Nat'l Lib. Med. (NCIB NLM NIH), Bethesda, Md., and Altschul et al., NAR, 1997, 25, 3389-3402). Another alignment program is ALIGN Plus (Scientific and Educational Software, Pa.), using default parameters. Another sequence software program that finds use is the TFASTA Data Searching Program available in the Sequence Software Package Version 6.0 (Genetics Computer Group, University of Wisconsin, Madison, Wis.).

A conservative substitution is a substitution of one amino acid for another with similar characteristics. Conservative substitutions include substitutions within the following groups: valine, alanine, and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Any substitution of one member of the above mentioned polar, basic, or acidic groups by another member of the same group can be deemed a conservative substitution. By contrast, a non-conservative substitution is a substitution of one amino acid for another with dissimilar characteristics.

For example, a 8-amino-7-oxononanoate synthase (BioF, or ACP-dependent BioF) described herein can have at least 70% sequence identity or homology (e.g., at least 75%, 80%, 85%, 90%, 95%, 97%, 98%, 99%, or 100%) to the amino acid sequence of an *Escherichia coli* 8-amino-7-oxononanoate synthase (BioF) (EC:2.3.1.47, see GenBank Accession No. AAA23516.1, SEQ ID NO: 23), See FIG. 9D.

For example, a thioesterase (TE) described herein can have at least 70% sequence identity or homology (e.g., at least 75%, 80%, 85%, 90%, 95%, 97%, 98%, 99%, or 100%) to the amino acid sequence of an *Escherichia coli* thioesterase encoded by tesB (see GenBank Accession No. AAA24665.1, SEQ ID NO: 1), or the gene products encoded by tesA or fatB (see GenBank Accession No. ABJ63754.1, SEQ ID NO:21; see GenBank Accession No. CCC78182.1, SEQ ID NO:22). See FIGS. 9A and 9D.

For example, a carboxylate reductase described herein can have at least 70% sequence identity or homology (e.g., at least 75%, 80%, 85%, 90%, 95%, 97%, 98%, 99%, or 100%) to the amino acid sequence of a *Mycobacterium marinum* (see GenBank Accession No. ACC40567.1, SEQ ID NO: 2), a *Mycobacterium smegmatis* (see GenBank Accession No. ABK71854.1, SEQ ID NO: 3), a *Segniliparus rugosus* (see Genbank Accession No. EFV11917.1, SEQ ID NO: 4), a *Mycobacterium smegmatis* (see GenBank Accession No. ABK75684.1, SEQ ID NO: 5), a *Mycobacterium massiliense* (see GenBank Accession No. EIV11143.1, SEQ ID NO: 6), or a *Segniliparus rotundus* (see GenBank Accession No. ADG98140.1, SEQ ID NO: 7) carboxylate reductase. See, FIGS. 9A-9C.

For example, a ω-transaminase described herein can have at least 70% sequence identity or homology (e.g., at least 75%, 80%, 85%, 90%, 95%, 97%, 98%, 99%, or 100%) to the amino acid sequence of a *Chromobacterium violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), a *Rhodobacter sphaeroides* (see Genbank Accession No. ABA81135.1, SEQ ID NO: 11), an *Escherichia coli* (see RefSeq Accession No. NP 417544.5, SEQ ID NO: 12), or a *Vibrio fluvialis* (see Genbank Accession No. AEA39183.1, SEQ ID NO: 13) ω-transaminase. Some of these ω-transaminases are diamine ω-transaminases. See, FIGS. 9C and 9D.

For example, a phosphopantetheinyl transferase described herein can have at least 70% sequence identity or homology (e.g., at least 75%, 80%, 85%, 90%, 95%, 97%, 98%, 99%, or 100%) to the amino acid sequence of a *Bacillus subtilis* phosphopantetheinyl transferase (see RefSeq Accession No. WP 003234549.1, SEQ ID NO:14) or a *Nocardia* sp. NRRL 5646 phosphopantetheinyl transferase (see Genbank Accession No. ABI83656.1, SEQ ID NO:15). See FIG. 7.

For example, a pimeloyl-ACP methyl ester esterase described herein can have at least 70% sequence identity or homology (e.g., at least 75%, 80%, 85%, 90%, 95%, 97%, 98%, 99%, or 100%) to the amino acid sequence of an *Escherichia coli* pimeloyl-ACP methyl ester esterase (BioH) (see GenBank Accession No. AAC76437.1, SEQ ID NO:17). See, FIG. 9D.

For example, a 6-carboxyhexanoate-CoA ligase described herein can have at least 70% sequence identity or homology (e.g., at least 75%, 80%, 85%, 90%, 95%, 97%, 98%, 99%, or 100%) to the amino acid sequence of an *Bacillus subtilis* (strain 168) 6-carboxyhexanoate-CoA ligase (BioW) (EC: 6.2.1.14, see GenBank Accession No. AAB17457.1, SEQ ID NO:18). See, FIG. 9D.

For example, a 8-amino-7-oxononanoate synthase described herein can have at least 70% sequence identity or homology (e.g., at least 75%, 80%, 85%, 90%, 95%, 97%, 98%, 99%, or 100%) to the amino acid sequence of an *Bacillus subtilis* (strain 168) 8-amino-7-oxononanoate synthase (BioF) (EC:2.3.1.47, see GenBank Accession No. AAB17459.1, SEQ ID NO: 19). See, FIG. 9D. Other bioF genes and BioF proteins from different hosts are well known in the art and can be easily identified in public databases such as GenBank, ExPASy, and via Enzyme Commission numbers.

For example, a SAM-dependent malonyl-ACP O-methyltransferase described herein can have at least 70% sequence identity or homology (e.g., at least 75%, 80%, 85%, 90%, 95%, 97%, 98%, 99%, or 100%) to the amino acid sequence of a *Escherichia coli* malonyl-ACP O-methyltransferase (BioC) (EC:2.1.1.197, see RefSeq Accession No. NP_415298.1, SEQ ID NO: 20). See, FIG. 9D.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the disclosure. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This disclosure also provides (i) functional variants of the enzymes used in the methods of the disclosure and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine (SEQ ID NO: 24)), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a methyltransferase, a synthase, β-ketothiolase, a dehydratase, a hydratase, a dehydrogenase, a methylesterase, a thioesterase, a reversible CoA-ligase, a CoA-transferase, a reductase, deacetylase, N-acetyl transferase or a ω-transaminase as described in more detail below.

In addition, the production of one or more C7 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Figure 3:
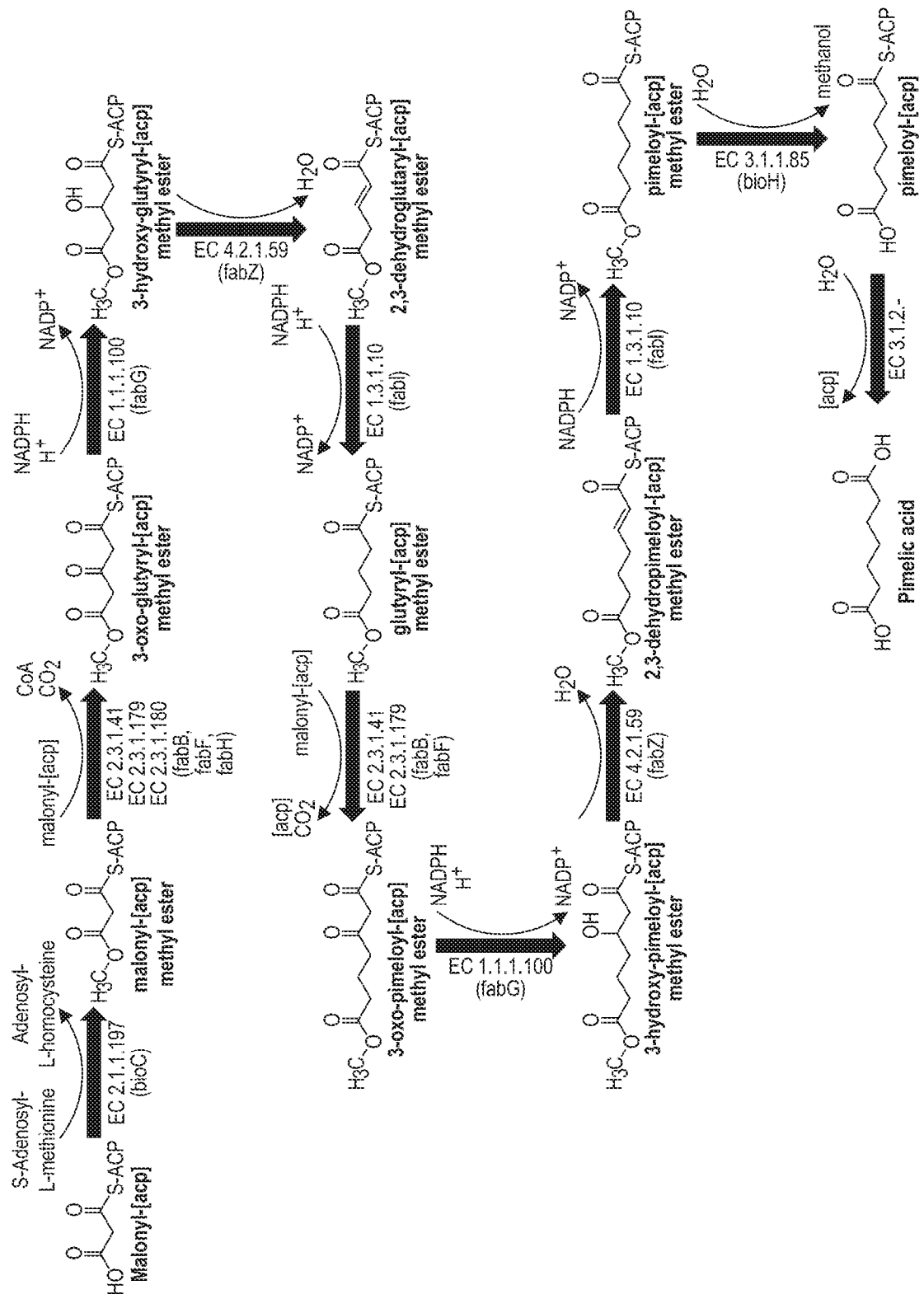
FIG. 3 is a schematic of an exemplary biochemical pathway leading to pimelic acid from malonyl-ACP through two cycles of methyl-ester shielded carbon chain elongation.

Enzymes Generating the C7 Aliphatic Backbone for Conversion to C7 Building Blocks As depicted in FIG. 3, the first step in biotin biosynthesis is the methylation of malonyl-ACP by BioC (a S-adenosyl-L-methionine (SAM)-dependent methyltransferase). The malonyl-ACP methyl ester thus generated then serves as a starter unit for the fatty acid biosynthesis pathway, two rounds of fatty acid elongation and reduction then occur (catalysed by FabB, F, G, Z and I) to generate pimelyl-ACP methyl ester. Pimelyl-ACP is then generated by the removal of the methyl group by the esterase BioH. Biotin biosynthesis then continues via a series of reactions catalysed by the enzymes BioF, BioA, BioB and BioD. One of the intermediates in biotin biosynthesis, pimelyl-ACP, can also be converted to 7-aminoheptanoic acid (7-AHA) in a synthetic metabolic pathway. In this pathway a thioesterase (1E) is used to release pimelic acid from pimelyl-ACP. Then carboxylic acid reductase (CAR) reduces the free pimelic acid to the cognate semi-aldehyde, with the final catalytic step being the amination of the semi-aldehyde by the ω-transaminase (ω-TAM) to produce 7-AHA. The export of 7-AHA from the cell then may be facilitated by the transport protein LysE.

The native biotin pathway thus provides a potential source of the pimelic acid intermediate that can be subsequently metabolized to 7-AHA. As biotin is only required in trace amounts the natural flux through this pathway is very low. Initial attempts to increase the flux to pimelic acid in *E. coli* have yielded only trace amounts of pimelic acid (<0.1 ppm), due in part to complex regulation of the biotin pathway and the toxicity associated with overexpression of pathway enzymes. In order to bypass these issues strains of *E. coli* with increased flux through the biotin pathway were sourced. A series of strains, generated by multiple rounds of random mutagenesis, have been reported to produce almost 1 g/L of biotin (U.S. Pat. No. 6,284,500 B1). These strains were used in order to provide a genetic background in which flux through the native biotin pathway is high with feedback and other negative regulatory mechanisms non-functional or much reduced.

In some embodiments, a methyl ester shielded carbon chain elongation associated with biotin biosynthesis route comprises using a malonyl-ACP O-methyltransferase to form a malonyl-ACP methyl ester, and then performing two cycles of carbon chain elongation using a β-ketoacyl-ACP synthase, a 3-oxoacyl-ACP reductase, a 3-hydroxyacyl-ACP dehydratase, and an enoyl-ACP reductase. A pimeloyl-ACP methyl ester esterase can be used to cleave the resulting pimeloyl-ACP methyl ester.

In some embodiments, a methyltransferase can be a malonyl-ACP O-methyltransferase classified, for example, under EC 2.1.1.197 such as the gene product of bioC from *Bacillus cereus* (see Genbank Accession No. AAS43086.1, SEQ ID NO:16) (see, for example, Lin, 2012, *Biotin Synthesis in Escherichia coli*, Ph.D. Dissertation, University of Illinois at Urbana-Champaign).

In some embodiments, a β-ketoacyl-ACP synthase may be classified, for example, under EC 2.3.1.—(e.g., EC 2.3.1.41, EC 2.3.1.179 or EC 2.3.1.180) such as the gene product of fabB, fabF, or fabH.

In some embodiments, a 3-oxoacyl-ACP reductase may be classified under EC 1.1.1.100, such as the gene product of fabG.

In some embodiments, an enoyl-ACP dehydratase such as a 3-hydroxyacyl-ACP dehydratase may be classified under EC 4.2.1.59, such as the gene product of fabZ.

In some embodiments, a trans-2-enoyl-CoA reductase may be classified under EC 1.3.1.—(e.g., EC 1.3.1.38, EC 1.3.1.8, EC 1.3.1.44), such as the gene product of ter (Nishimaki et al., *J. Biochem.*, 1984, 95, 1315-1321; Shen et al., 2011, supra) or tdter (Bond-Watts et al., *Biochemistry*, 2012, 51, 6827-6837).

In some embodiments, an enoyl-ACP reductase may be classified under EC 1.3.1.10 such as the gene product of fabI.

In some embodiments, a pimeloyl-ACP methyl ester esterase may be classified, for example, under EC 3.1.1.85 such as the gene product of bioH from *E. coli*. See Genbank Accession No. AAC76437.1, SEQ ID NO:17.

Figure 1:
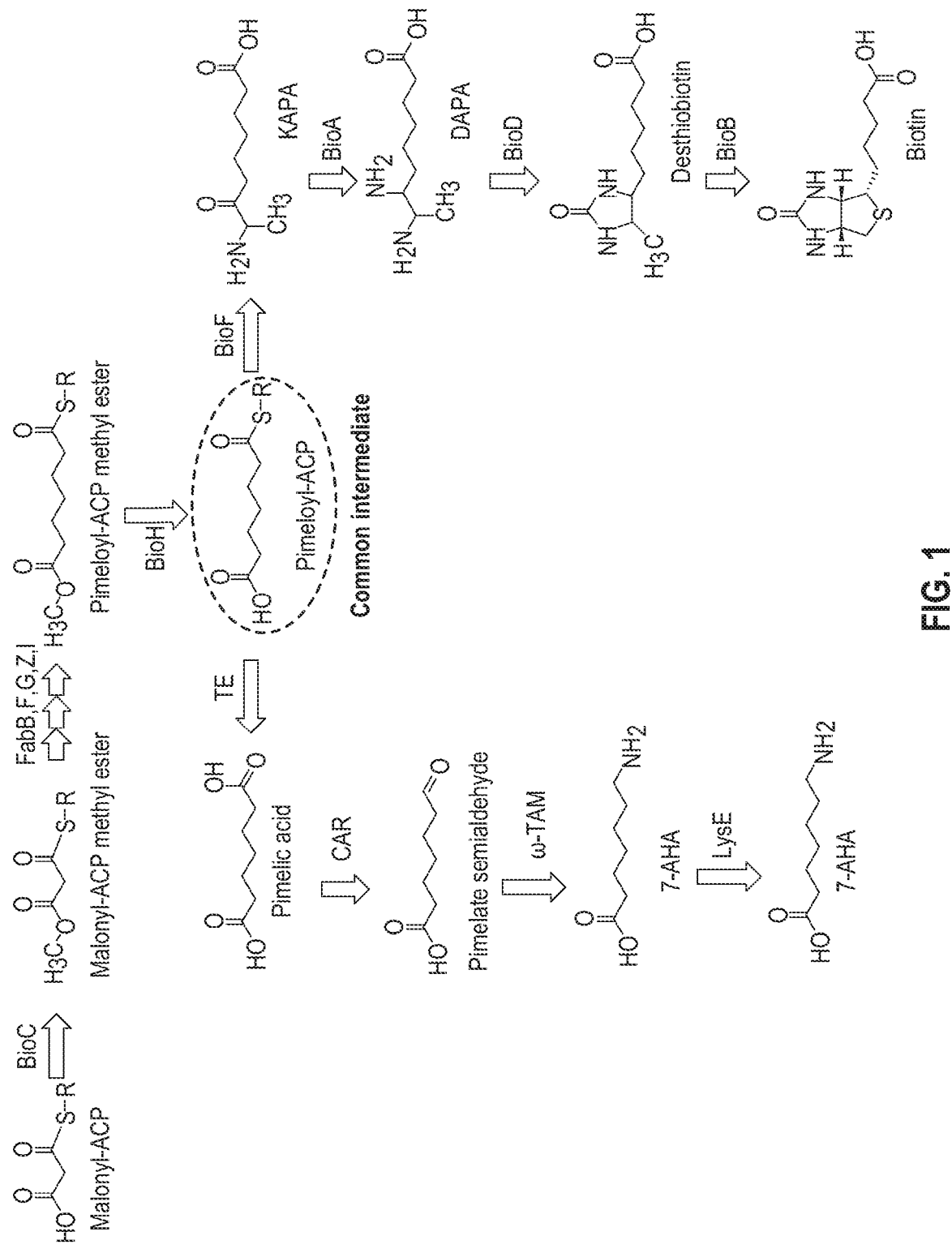
Figure 2:
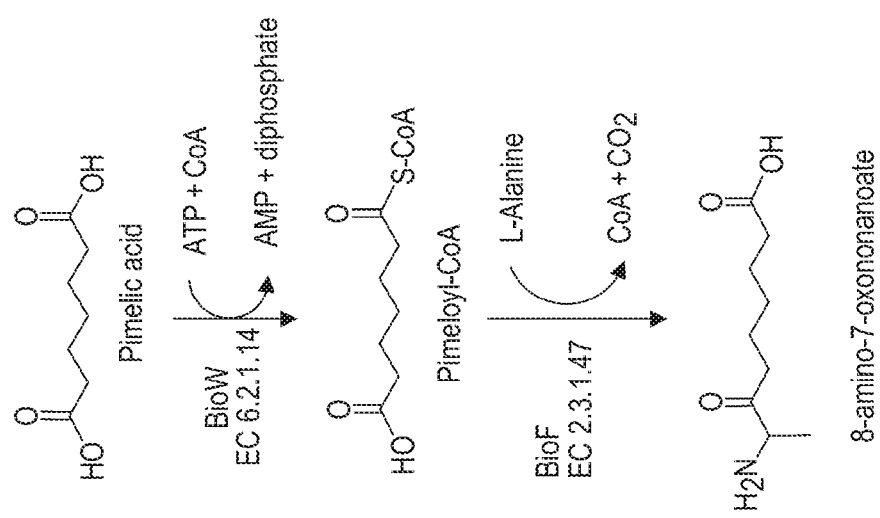
FIG. 2 is a schematic of exemplary biochemical pathways leading to 8-amino-7-oxononanoate (KAPA) starting from pimelic acid.

Enzymes Generating the Terminal Carboxyl Groups in the Biosynthesis of C7 Building Blocks As depicted in FIG. 1, a terminal carboxyl group can be enzymatically formed using a thioesterase (TE).

In some embodiments, the second terminal carboxyl group leading to the synthesis of a C7 building block is enzymatically formed by a thioesterase classified, for example, under EC 3.1.2.-, such as the gene product of YciA, tesB (Genbank Accession No. AAA24665.1, SEQ ID NO: 1) or the gene products encoded by tesA or fatB (see GenBank Accession No. ABJ63754.1, SEQ ID NO:21; see GenBank Accession No. CCC78182.1, SEQ ID NO:22) (see, for example, Cantu et al., *Protein Science*, 2010, 19, 1281-1295; Zhuang et al., *Biochemistry*, 2008, 47(9), 2789-2796; or Naggert et al., *J. Biol. Chem.*, 1991, 266(17), 11044 11050).

Enzymes Generating the Terminal Amine Groups in the Biosynthesis of C7 Building Blocks As depicted in FIG. 5 and FIGS. 6A-6C, terminal amine groups can be enzymatically formed using a ω-transaminase or a deacetylase.

In some embodiments, the first or second terminal amine group leading to the synthesis of 7-aminoheptanoic acid is enzymatically formed by a ω-transaminase classified, for example, under EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 8), *Pseudomonas aeruginosa* (Genbank Accession No. AAG08191.1, SEQ ID NO: 9), *Pseudomonas syringae* (Genbank Accession No. AAY39893.1, SEQ ID NO: 10), *Rhodobacter sphaeroides* (Genbank Accession No. ABA81135.1, SEQ ID NO: 11), *Escherichia coli* (RefSeq Accession No. NP 417544.5, SEQ ID NO: 12), *Vibrio Fluvialis* (Genbank Accession No. AEA39183.1, SEQ ID NO: 13), *Streptomyces griseus*, or *Clostridium viride*. Some of these ω-transaminases are diamine ω-transaminases (e.g., SEQ ID NO: 12). For example, the ω-transaminases classified, for example, under EC 2.6.1.29 or EC 2.6.1.82 may be diamine ω-transaminases.

The reversible ω-transaminase from *Chromobacterium violaceum* (Genbank Accession No. AAQ59697.1, SEQ ID NO: 8) has demonstrated analogous activity accepting 6-aminohexanoic acid as amino donor, thus forming the first terminal amine group in adipate semialdehyde (Kaulmann et al., *Enzyme and Microbial Technology*, 2007, 41, 628-637).

The reversible 4-aminobubyrate:2-oxoglutarate transaminase from *Streptomyces griseus* has demonstrated analogous activity for the conversion of 6-aminohexanoate to adipate semialdehyde (Yonaha et al., *Eur. J. Biochem.*, 1985, 146: 101-106).

The reversible 5-aminovalerate transaminase from *Clostridium viride* has demonstrated analogous activity for the conversion of 6-aminohexanoate to adipate semialdehyde (Barker et al., *J. Biol. Chem.*, 1987, 262(19), 8994-9003).

In some embodiments, a terminal amine group leading to the synthesis of 7-aminoheptanoate or heptamethylenediamine is enzymatically formed by a diamine ω-transaminase. For example, the second terminal amino group can be enzymatically formed by a diamine ω-transaminase classified, for example, under EC 2.6.1.29 or classified, for example, under EC 2.6.1.82, such as the gene product of YgjG from *E. coli* (RefSeq Accession No. NP_417544.5, SEQ ID NO: 12).

The gene product of ygjG accepts a broad range of diamine carbon chain length substrates, such as putrescine, cadaverine and spermidine (see, for example, Samsonova et al., *BMC Microbiology*, 2003, 3:2).

The diamine ω-transaminase from *E. coli* strain B has demonstrated activity for 1,7 diaminoheptane (Kim, *The Journal of Chemistry*, 1964, 239(3), 783-786).

In some embodiments, the second terminal amine group leading to the synthesis of heptamethylenediamine is enzymatically formed by a deacetylase such as acetylputrescine deacetylase classified, for example, under EC 3.5.1.62. The acetylputrescine deacetylase from *Micrococcus luteus* K-11 accepts a broad range of carbon chain length substrates, such as acetylputrescine, acetylcadaverine and $N^8$_acetylspermidine (see, for example, Suzuki et al., 1986, *BBA—General Subjects*, 882(1):140-142).

Figure 7:
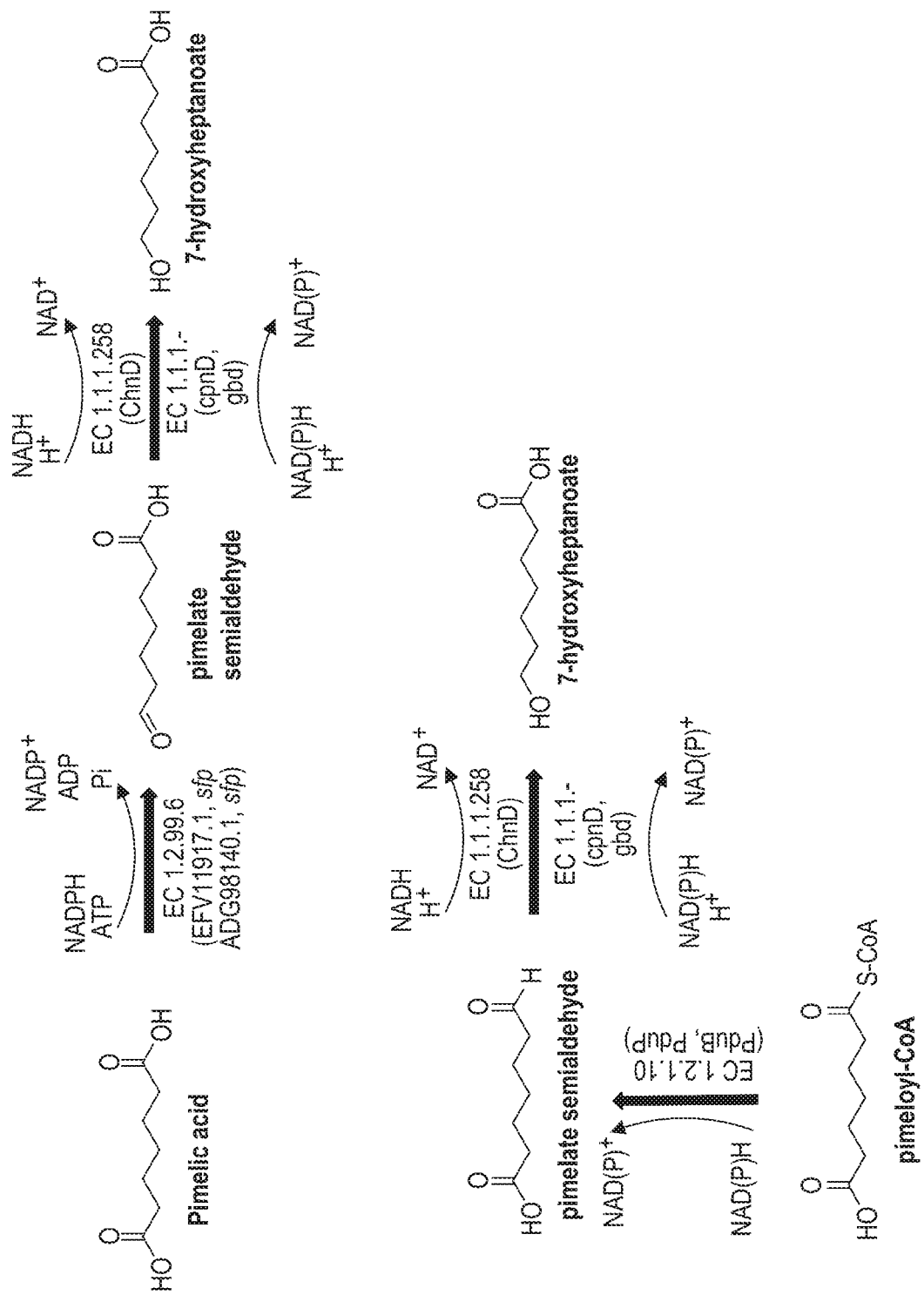
FIG. 7 is a schematic of exemplary biochemical pathways leading to 7-hydroxyheptanoate using pimelate, pimeloyl-CoA, or pimelate semialdehyde as precursors.
Figure 8:
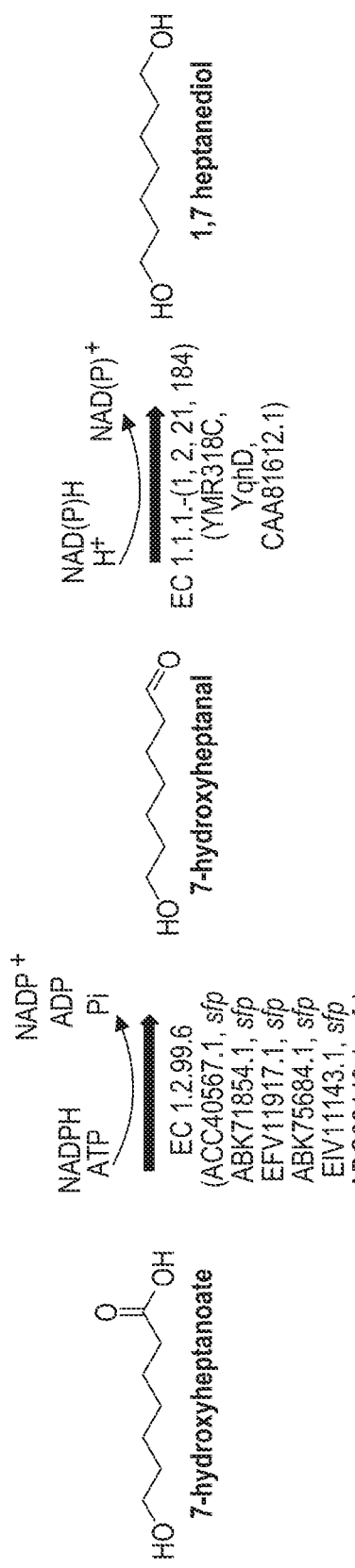
FIG. 8 is a schematic of an exemplary biochemical pathway leading to 1,7-heptanediol using 7-hydroxyheptanoate as a precursor.

Enzymes Generating the Terminal Hydroxyl Groups in the Biosynthesis of C7 Building Blocks As depicted in FIG. 7 and FIG. 8, a terminal hydroxyl group can be enzymatically formed using an alcohol dehydrogenase.

In some embodiments, a terminal hydroxyl group leading to the synthesis of 1,7 heptanediol is enzymatically formed by an alcohol dehydrogenase classified, for example, under EC 1.1.1.—(e.g., 1, 2, 21, or 184) such as the gene product of YMR318C (classified, for example, under EC 1.1.1.2, see Genbank Accession No. CAA90836.1) (Larroy et al., 2002, *Biochem J.*, 361(Pt 1), 163-172), the gene product of YghD, the gene product of cpnD (Iwaki et al., 2002, *Appl. Environ. Microbiol.*, 68(11):5671-5684), the gene product of gbd, or a 6-hydroxyhexanoate dehydrogenase classified, for example, under EC 1.1.1.258 such as the gene product of ChnD (Iwaki et al., *Appl. Environ. Microbiol.*, 1999, supra).

Biochemical Pathways

Pathways from Malonyl-ACP to Pimeloyl-ACP as Central Precursor Leading to C7 Building Block As depicted in FIG. 1 and FIG. 3, the first step in biotin biosynthesis is the methylation of malonyl-ACP by BioC (a S-adenosyl-L-methionine (SAM)-dependent methyltransferase). The malonyl-ACP methyl ester thus generated then serves as a starter unit for the fatty acid biosynthesis pathway, two rounds of fatty acid elongation and reduction then occur (catalysed by FabB, F, G, Z and I) to generate pimelyl-ACP methyl ester. Pimelyl-ACP is then generated by the removal of the methyl group by the esterase BioH. Biotin biosynthesis then continues via a series of reactions catalysed by the enzymes BioF, BioA, BioB and BioD. One of the intermediates in biotin biosynthesis, pimelyl-ACP, can also be converted to 7-aminoheptanoic acid (7-AHA) in a synthetic metabolic pathway. In this pathway a thioesterase (TE) is used to release pimelic acid from pimelyl-ACP. Then carboxylic acid reductase (CAR) reduces the free pimelic acid to the cognate semi-aldehyde, with the final catalytic step being the amination of the semi-aldehyde by the ω-transaminase (ω-TAM) to produce 7-AHA. The export of 7-AHA from the cell then may be facilitated by the transport protein LysE.

The native biotin pathway thus provides a potential source of the pimelic acid intermediate that can be subsequently metabolized to 7-AHA. As biotin is only required in trace amounts the natural flux through this pathway is very low. Initial attempts to increase the flux to pimelic acid in *E. coli* have yielded only trace amounts of pimelic acid (<0.1 ppm), due in part to complex regulation of the biotin pathway and the toxicity associated with overexpression of pathway enzymes. In order to bypass these issues strains of *E. coli* with increased flux through the biotin pathway were sourced. A series of strains, generated by multiple rounds of random mutagenesis, have been reported to produce almost 1 g/L of biotin (U.S. Pat. No. 6,284,500 B1). These strains were used in order to provide a genetic background in which flux through the native biotin pathway is high with feedback and other negative regulatory mechanisms non-functional or much reduced.

Pathways Using Pimeloyl-ACP as Central Precursor to Pimelic Acid

In some embodiments, pimelic acid is synthesized from the central precursor, pimeloyl-ACP, by conversion of pimeloyl-ACP to pimelate by a thioesterase classified, for example, under EC 3.1.2.—such as the gene products encoded by tesA orfatB (Genbank Accession No. ABJ63754.1, SEQ ID NO:21; Genbank Accession No. CCC78182.1, SEQ ID NO:22). See FIG. 3.

Pathways Using Pimelate Semialdehyde as Precursor to 7-Aminoheptanoate

In some embodiments, 7-aminoheptanoate is synthesized from the central precursor, pimelate, by conversion of pimelate to pimelate semialdehyde by a carboxylate reductase classified, for example, under EC 1.2.99.6 such as the gene product of car in combination with a phosphopantetheine transferase enhancer (e.g., encoded by a sfp (RefSeq Accession No. WP 003234549.1, SEQ ID NO:14) gene from *Bacillus subtilis* or npt (Genbank Accession No. ABI83656.1, SEQ ID NO:15) gene from *Nocardia*) or the gene products of GriC and GriD from *Streptomyces griseus* (Suzuki et al., *J. Antibiot.*, 2007, 60(6), 380-387); followed by conversion of pimelate semialdehyde to 7-aminoheptanoate by a ω-transaminase (e.g., EC 2.6.1.18, EC 2.6.1.19, EC 2.6.1.48, EC 2.6.1.29, EC 2.6.1.82 such as SEQ ID NOs:8-13). The carboxylate reductase can be obtained, for example, from *Mycobacterium marinum* (Genbank Accession No. ACC40567.1, SEQ ID NO: 2), *Mycobacterium smegmatis* (Genbank Accession No. ABK71854.1, SEQ ID NO: 3), *Segniliparus rugosus* (Genbank Accession No. EFV11917.1, SEQ ID NO: 4), *Mycobacterium smegmatis* (Genbank Accession No. ABK75684.1, SEQ ID NO: 5), *Mycobacterium massiliense* (Genbank Accession No. EIV11143.1, SEQ ID NO: 6), or *Segniliparus rotundus* (Genbank Accession No. ADG98140.1, SEQ ID NO: 7). See FIG. 5.

Pathway Using 7-Aminoheptanoate, 7-Hydroxyheptanoate or Pimelate Semialdehyde as a Precursor to Heptamethylenediamine In some embodiments, heptamethylenediamine is synthesized from the central precursor, 7-aminoheptanoate, by conversion of 7-aminoheptanoate to 7-aminoheptanal by a carboxylate reductase classified, for example, under EC 1.2.99.6 such as the gene product of car (see above) in combination with a phosphopantetheine transferase enhancer (e.g., encoded by a sfp (RefSeq Accession No. WP 003234549.1, SEQ ID NO:14) gene from *Bacillus subtilis* or npt (Genbank Accession No. ABI83656.1, SEQ ID NO:15) gene from *Nocardia*) or the gene product of GriC & GriD; followed by conversion of 7-aminoheptanal to heptamethylenediamine by a ω-transaminase (e.g., classified, for example, under EC 2.6.1.18, EC 2.6.1.19, EC 2.6.1.29, EC 2.6.1.48, or EC 2.6.1.82 such as SEQ ID NOs:8-13, see above). See FIG. 6A.

The carboxylate reductase encoded by the gene product of car and the phosphopantetheine transferase enhancer npt or sfp has broad substrate specificity, including terminal difunctional C4 and C5 carboxylic acids (Venkitasubramanian et al., *Enzyme and Microbial Technology*, 2008, 42, 130-137).

In some embodiments, heptamethylenediamine is synthesized from the central precursor, 7-hydroxyheptanoate (which can be produced as described in FIG. 5), by conversion of 7-hydroxyheptanoate to 7-hydroxyheptanal by a carboxylate reductase classified, for example, under EC 1.2.99.6 such as the gene product of car (see above) in combination with a phosphopantetheine transferase enhancer (e.g., encoded by a sfp gene from *Bacillus subtilis* or npt gene from *Nocardia*) or the gene product of GriC & GriD (Suzuki et al., *J. Antibiot.*, 2007, 60(6), 380-387); followed by conversion of 7-aminoheptanal to 7-aminoheptanol by a ω-transaminase classified, for example, under EC 2.6.1.18, EC 2.6.1.19, EC 2.6.1.29, EC 2.6.1.48, or EC 2.6.1.82 such as SEQ ID NOs:8-13, see above; followed by conversion to 7-aminoheptanal by an alcohol dehydrogenase classified, for example, under EC 1.1.1.—(e.g., EC 1.1.1.1, EC 1.1.1.2, EC 1.1.1.21, or EC 1.1.1.184) such as the gene product of YMR318C (classified, for example, under EC 1.1.1.2, see Genbank Accession No. CAA90836.1) or YqhD (from *E. coli*, GenBank Accession No. AAA69178.1) (Liu et al., Microbiology, 2009, 155, 2078 2085; Larroy et al., 2002, Biochem J., 361(Pt 1), 163-172; Jarboe, 2011, *Appl. Microbiol. Biotechnol.*, 89(2), 249-257) or the protein having GenBank Accession No. CAA81612.1 (from *Geobacillus stearothermophilus*); followed by conversion to heptamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:8-13, see above. See FIG. 6A.

In some embodiments, heptamethylenediamine is synthesized from the central precursor, 7-aminoheptanoate, by conversion of 7-aminoheptanoate to N7-acetyl-7-aminoheptanoate by a N-acetyltransferase such as a lysine N-acetyltransferase classified, for example, under EC 2.3.1.32; followed by conversion to N7-acetyl-7-aminoheptanal by a carboxylate reductase classified, for example, under EC 1.2.99.6 such as the gene product of car (see above) in combination with a phosphopantetheine transferase enhancer (e.g., encoded by a sfp gene from *Bacillus subtilis* or npt gene from *Nocardia*) or the gene product of GriC & GriD; followed by conversion to N7-acetyl-1,7-diaminoheptane by a ω-transaminase classified, for example, under EC 2.6.1.18, EC 2.6.1.19, EC 2.6.1.29, EC 2.6.1.48, EC 2.6.1.46, or EC 2.6.1.82 such as SEQ ID NOs:8-13, see above; followed by conversion to heptamethylenediamine by an acetylputrescine deacylase classified, for example, under EC 3.5.1.62. See, FIG. 6B.

In some embodiments, heptamethylenediamine is synthesized from the central precursor, pimelate semialdehyde, by conversion of pimelate semialdehyde to heptanedial by a carboxylate reductase classified, for example, under EC 1.2.99.6 such as the gene product of car (see above) in combination with a phosphopantetheine transferase enhancer (e.g., encoded by a sfp gene from *Bacillus subtilis* or npt gene from *Nocardia*) or the gene product of GriC & GriD; followed by conversion to 7-aminoheptanal by a ω-transaminase classified, for example, under EC 2.6.1.18, EC 2.6.1.19, or EC 2.6.1.48; followed by conversion to heptamethylenediamine by a ω-transaminase classified, for example, under EC 2.6.1.18, EC 2.6.1.19, EC 2.6.1.29, EC 2.6.1.48, EC 2.6.1.46, or EC 2.6.1.82 such as SEQ ID NOs:8-13, see above. See FIG. 6C.

Pathways Using Pimelate or Pimelate Semialdehyde as Central Precursor to 1,7-Heptanediol In some embodiments, 7-hydroxyheptanoate is synthesized from the central precursor, pimelate, by conversion of pimelate to pimelate semialdehyde by a carboxylate reductase classified, for example, under EC 1.2.99.6 such as the gene product of car (see above) in combination with a phosphopantetheine transferase enhancer (e.g., encoded by a sfp gene from *Bacillus subtilis* or npt gene from *Nocardia*) or the gene product of GriC & GriD; followed by conversion to 7-hydroxyheptanoate by a dehydrogenase classified, for example, under EC 1.1.1.—such as a 6-hydroxyhexanoate dehydrogenase classified, for example, under EC 1.1.1.258 such as the gene from of ChnD or a 5-hydroxypentanoate dehydrogenase classified, for example, under EC 1.1.1.—such as the gene product of CpnD (see, for example, Iwaki et al., 2002, *Appl. Environ. Microbiol.*, 68(11):5671-5684) or a 4-hydroxybutyrate dehydrogenase such as gbd. See FIG. 7. Pimelate semialdehyde also can be produced from pimeloyl-CoA using an acetylating aldehyde dehydrogenase as described above. See, also FIG. 7.

In some embodiments, 1,7 heptanediol is synthesized from the central precursor, 7-hydroxyheptanoate, by conversion of 7-hydroxyheptanoate to 7-hydroxyheptanal by a carboxylate reductase classified, for example, under EC 1.2.99.6 such as the gene product of car (see above) in combination with a phosphopantetheine transferase enhancer (e.g., encoded by a sfp gene from *Bacillus subtilis* or npt gene from *Nocardia*) or the gene product of GriC & GriD; followed by conversion of 7-hydroxyheptanal to 1,7 heptanediol by an alcohol dehydrogenase classified, for example, under EC 1.1.1.—such as EC 1.1.1.1, EC 1.1.1.2, EC 1.1.1.21, or EC 1.1.1.184) such as the gene product of YMR318C or YqhD (see, e.g., Liu et al., Microbiology, 2009, 155, 2078-2085; Larroy et al., 2002, Biochem 361(Pt 1), 163-172; or Jarboe, 2011, Appl. Microbiol. Biotechnol., 89(2), 249-257) or the protein having GenBank Accession No. CAA81612.1 (from *Geobacillus stearothermophilus*). See, FIG. 8.

Cultivation Strategy

In some embodiments, the cultivation strategy entails achieving an aerobic, anaerobic or micro-aerobic cultivation condition.

In some embodiments, the cultivation strategy entails nutrient limitation such as nitrogen, phosphate or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more C7 building blocks can derive from biological or non-biological feedstocks.

In some embodiments, the biological feedstock can be, can include, or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., Appl. Biochem. Biotechnol., 2012, 166, 1801-1813; Yang et al., *Biotechnology for Biofuels*, 2012, 5:13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such as benzoate analogues has been demonstrated in several microorganisms such as *Pseudomonas putida, Cupriavidus necator* (Bugg et al., *Current Opinion in Biotechnology*, 2011, 22, 394-400; Perez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al, *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock can be or can derive from natural gas, syngas, $CO_2/H_2$, methanol, ethanol, benzoic acid, non-volatile residue (NVR), a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljung-dahlii* and *Clostridium autoethanogenum* (Kopke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1), 152-156).

In some embodiments, the host microorganism is a prokaryote. For example, the prokaryote can be a bacterium from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C7 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C7 building blocks.

Metabolic Engineering

The present disclosure provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This disclosure provides host cells of any of the genera and species listed and genetically engineered to express one or more (e.g., two, three, four, five, six, seven, eight, nine, 10, 11, 12 or more) recombinant forms of any of the enzymes recited in the disclosure. Thus, for example, the host cells can contain exogenous nucleic acids encoding enzymes catalyzing one or more of the steps of any of the pathways described herein.

In addition, this disclosure recognizes that where enzymes have been described as accepting CoA-activated substrates, analogous enzyme activities associated with ACP-bound substrates exist that are not necessarily in the same enzyme class.

Also, this disclosure recognizes that where enzymes have been described accepting (R)-enantiomers of substrate, analogous enzyme activities associated with (S)-enantiomer substrates exist that are not necessarily in the same enzyme class.

This disclosure also recognizes that where an enzyme is shown to accept a particular co-factor, such as NADPH, or a co-substrate, such as acetyl-CoA, many enzymes are promiscuous in terms of accepting a number of different co-factors or co-substrates in catalyzing a particular enzyme activity. Also, this disclosure recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined herein can be gene dosed (i.e., overexpressed by having a plurality of copies of the gene in the host organism), into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C7 building block.

Attenuation strategies include, but are not limited to; the use of transposons, homologous recombination (double cross-over approach), mutagenesis, enzyme inhibitors and RNA interference (RNAi).

In some embodiments, fluxomic, metabolomic and transcriptomal data can be utilized to inform or support genome-scale system biology techniques, thereby devising genome scale attenuation or knockout strategies in directing carbon flux to a C7 building block.

In some embodiments, the host microorganism's tolerance to high concentrations of at least one C7 building block can be improved through continuous cultivation in a selective environment.

In some embodiments, where pathways require excess NADPH co-factor in the synthesis of a C7 building block, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific). For example, avoiding dissipation of an NADH imbalance towards C7 building blocks, a NADPH-specific glutamate dehydrogenase can be attenuated.

In some embodiments, an endogenous glutamate dehydrogenase (EC 1.4.1.3) that utilizes both NADH and NADPH as co-factors can be attenuated.

In some embodiments, a membrane-bound enoyl-CoA reductases can be solubilized via expression as a fusion protein to a small soluble protein such as a maltose binding protein (Gloerich et al., FEBS Letters, 2006, 580, 2092-2096).

In some embodiments using hosts that naturally accumulate polyhydroxyalkanoates, the endogenous polymer synthase enzymes can be attenuated in the host strain.

In some embodiments, a L-alanine dehydrogenase can be overexpressed in the host to regenerate L-alanine from pyruvate as an amino donor for ω-transaminase reactions.

In some embodiments, a L-glutamate dehydrogenase specific for the co-factor used to achieve co-factor imbalance can be overexpressed in the host to regenerate L-glutamate from 2-oxoglutarate as an amino donor for ω-transaminase reactions. For example, promoting dissipation of the NADH imbalance towards C7 building blocks, a NADH-specific glutamate dehydrogenase can be overexpressed.

In some embodiments, enzymes such as pimeloyl-CoA dehydrogenase classified under, EC 1.3.1.62; an acyl-CoA dehydrogenase classified, for example, under EC 1.3.8.7 or EC 1.3.8.1; and/or a glutaryl-CoA dehydrogenase classified, for example, under EC 1.3.8.6 that degrade central metabolites and central precursors leading to and including C7 building blocks can be attenuated.

In some embodiments, endogenous enzymes activating C7 building blocks via Coenzyme A esterification such as CoA-ligases (e.g., a pimeloyl-CoA synthetase) classified under, for example, EC 6.2.1.14 can be attenuated.

In some embodiments, a methanol dehydrogenase and a formaldehyde dehydrogenase can be overexpressed in the host to allow methanol catabolism via formate.

In some embodiments, a S-adenosylmethionine synthetase can be overexpressed in the host to generate S-Adenosyl-L-methionine as a co-factor for malonyl-ACP O-methyltransferase.

In some embodiments, the efflux of a C7 building block across the cell membrane to the extracellular media can be enhanced or amplified by genetically engineering structural modifications to the cell membrane or increasing any associated transporter activity for a C7 building block.

The efflux of heptamethylenediamine can be enhanced or amplified by overexpressing broad substrate range multidrug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499), NorA from *Staphylococcus aereus* (Ng et al., 1994, *Antimicrob Agents Chemother*, 38(6), 1345-1355), or Bmr from *Bacillus subtilis* (Neyfakh, 1992, *Antimicrob Agents Chemother*, 36(2), 484-485).

The efflux of 7-aminoheptanoate and heptamethylenediamine can be enhanced or amplified by overexpressing the solute transporters such as the lysE transporter from *Corynebacterium glutamicum* (Bellmann et al., 2001, *Microbiology*, 147, 1765-1774).

The efflux of pimelic acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C7 Building Blocks Using a Recombinant Host

Typically, one or more C7 building blocks can be produced by providing a host microorganism and culturing the provided microorganism with a culture medium containing a suitable carbon source as described above. In general, the culture media and/or culture conditions can be such that the microorganisms grow to an adequate density and produce a C7 building block efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C7 building block. Once produced, any method can be used to isolate C7 building blocks. For example, C7 building blocks can be recovered selectively from the fermentation broth via adsorption processes. In the case of pimelic acid and 7-aminoheptanoic acid, the resulting eluate can be further concentrated via evaporation, crystallized via evaporative and/or cooling crystallization, and the crystals recovered via centrifugation. In the case of heptamethylenediamine and 1,7-heptanediol, distillation may be employed to achieve the desired product purity.

The present disclosure is further described in the following examples, which do not limit the scope of the invention described in the claims.

EXAMPLES

Example 1

Strain Selection

A series of six biotin overproducing strains of *E. coli* were obtained, these were assessed for biotin productivity in small scale experiments and, based on initial biotin productivity, two of the strains were selected for further analysis, FERM BP 4928 and FERM BP 5667. These two strains were also analysed in high density fermentations with titres of biotin metabolites being >200 mg/L in chemically defined growth medium.

The biotin overproducing strains were modified to facilitate further manipulation and analysis; the plasmids bearing extra copies of the biotin operon were removed and; the T7 RNA polymerase gene was introduced to allow high level expression from the T7 promoter. This generated strains FERM BP-4928-P2(DE3)-4 and FERM BP-5667-P2(DE3)-A7.

Example 2

Expression of Thioesterases

The release of pimelic acid from pimelyl-ACP is catalysed by acyl-ACP thioesterases. The expression of a suitable thioesterase would be predicted to result in the release of pimelic acid. Nine different thioesterases were selected on the basis of diversity and in vitro activity and, following induction of expression, culture supernatants were analysed for pimelic acid. Pimelic acid levels were in all cases below the level of quantification and in some cases induction of gene expression also resulted in the cessation of cell growth. See Table 1.

Example 3

Deletion of Biotin Biosynthesis Genes

It was sought to increase the potential pool of pimelyl-ACP by deleting specific biotin biosynthesis genes from the chromosome. The bioF gene was the major target as the product of this gene catalyses the conversion of pimelyl-ACP to 8-amino-7-oxo-nonanoic acid ("KAPA") (FIG. 4), and the removal of this activity from the strain would be predicted to result in the accumulation of pimeloyl-ACP. In addition to the deletion of the bioF gene, the bioH gene was also deleted which would be expected to result in a strain that accumulates pimelyl-ACP methyl ester. See Table 1.

The strains carrying deletions of bioF and bioH were then analysed, and all were biotin auxotrophs. The bioF mutant strains were found to produce detectable levels of pimelic acid in shake flask experiments (~2.5 mg/L), while the bioH mutant strains were found to produce both pimelic acid methyl ester (~0.6 mg/L) and pimelic acid (~0.2 mg/L) in the culture supernatant. The production of both pimelic acid and pimelic acid methyl ester in the absence of an additional thioesterase indicates that native *E. coli* thioesterase activities are able to release ACP bound pimelic acid (and methyl ester). Additional thioesterase was expressed in the ΔbioF strains, however it did not resulted in an increase in pimelic acid levels above those found without an additional thioesterase. See Table 1.

In Table 1, pimelate production was analyzed in biotin mutant strains. Strains were cultured in chemically defined medium and were grown for 24 to 48 hours following induction. Culture supernatants were then analysed by LC-MS for pimelic acid and pimelic acid methyl ester.

TABLE 1

| Strain | bioF | bioH | thioesterase | pimelic acid (ppm) | pimelic acid methyl ester (ppm) |
|---|---|---|---|---|---|
| FERM BP-4928-P2(DE3)-4 | WT | WT | None | 0 | 0 |
| FERM BP-4928-P2(DE3)-4 | WT | WT | 9 different TEs[1] | 0, trace amount - TE2, TE5 (<0.1 ppm) | 0, trace amount - TE11 |
| FERM BP-4928-P2(DE3)-4 | Δ | WT | None | 2.5 | 0 |
| FERM BP-4928-P2(DE3)-4 | WT | Δ | None | 0.2 | 0.6 |
| FERM BP-4928-P2(DE3)-4 | Δ | Δ | None | 0.5 | 1.5 |
| FERM BP-4928-P2(DE3)-4 | Δ | WT | 7 different TEs[2] | 0.1-0.8 | 0, 0.2 with TE11 |

[1]TEs utilised were TE2, TE5, TE8, TE11, TE14, TE17, YciA, AA077182, 'tesA.
[2]TEs utilised were TE2, TE5, TE8, TE11, TE14, TE17, 'tesA.

Example 4

Production of 7-AHA in *E. coli*

Figure 4:
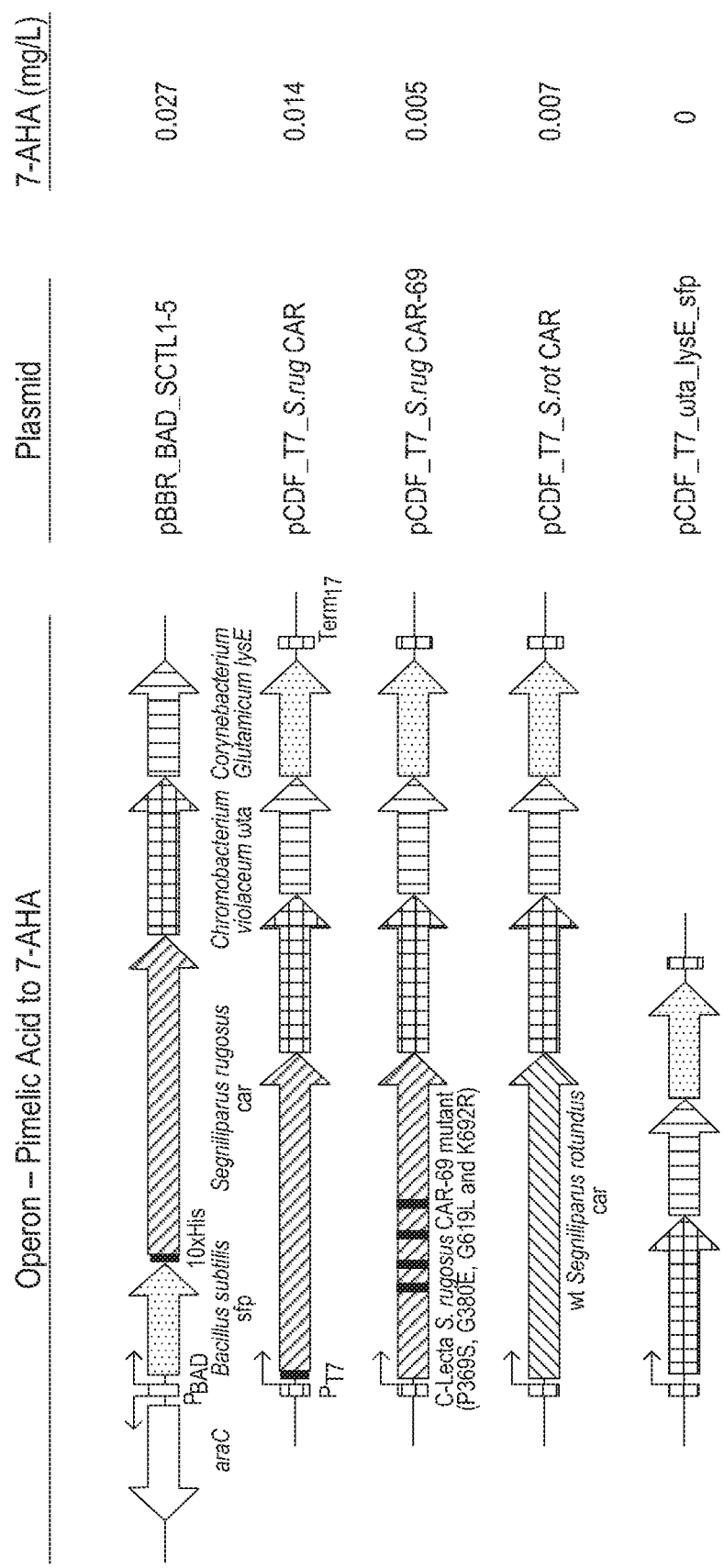
FIG. 4 illustrates the constructs for expression of pathway for conversion of pimelic acid to 7-AHA in the ΔbioF *E. coli* strain.
Figure 5:
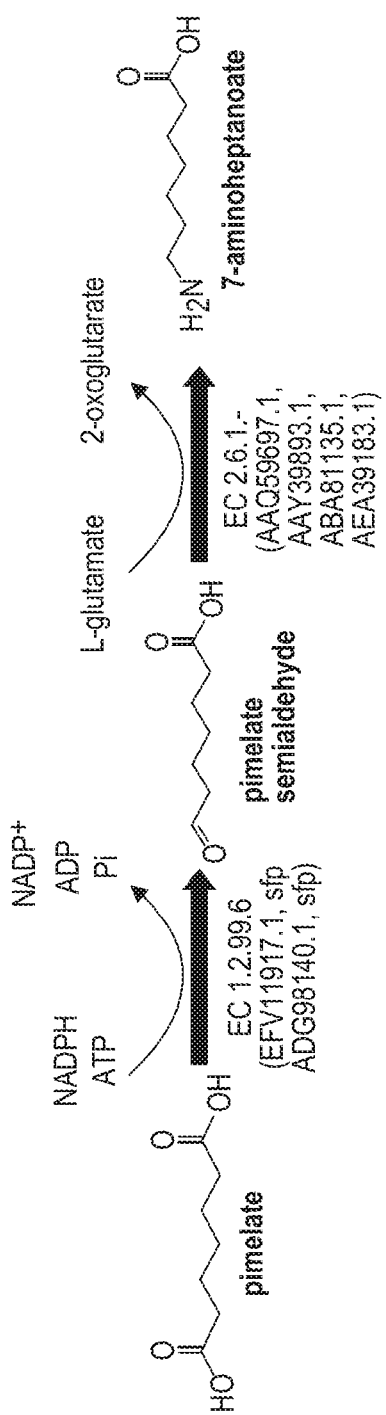
FIG. 5 is a schematic of exemplary biochemical pathways leading to 7-aminoheptanoate using pimelate or pimelate semialdehyde as precursors.
Figure 6A:
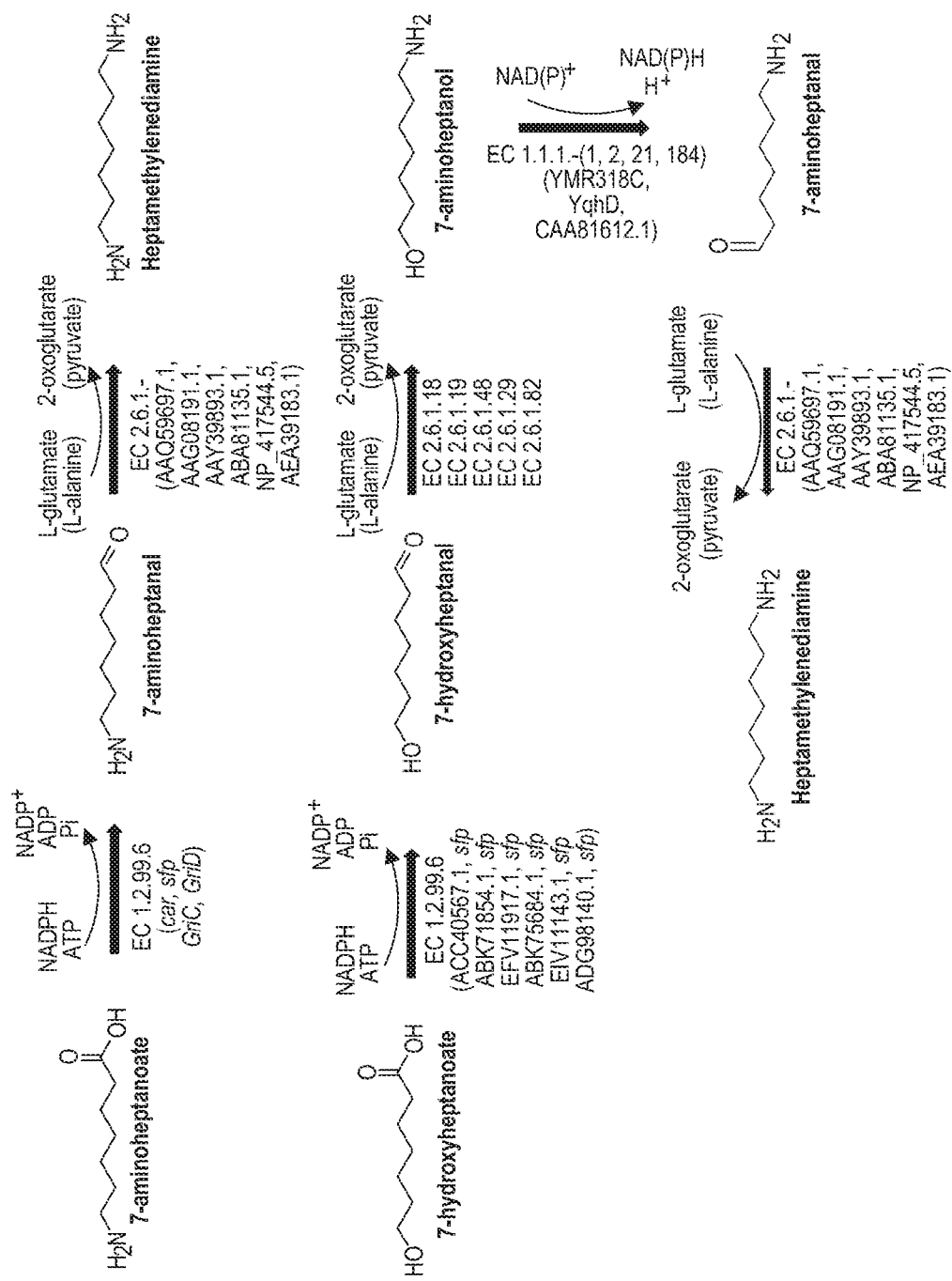
FIGS. 6A-6C are schematics of exemplary biochemical pathways leading to heptamethylenediamine using 7-aminoheptanoate, 7-hydroxyheptanoate or pimelate semialdehyde as central precursors.
Figure 6B:
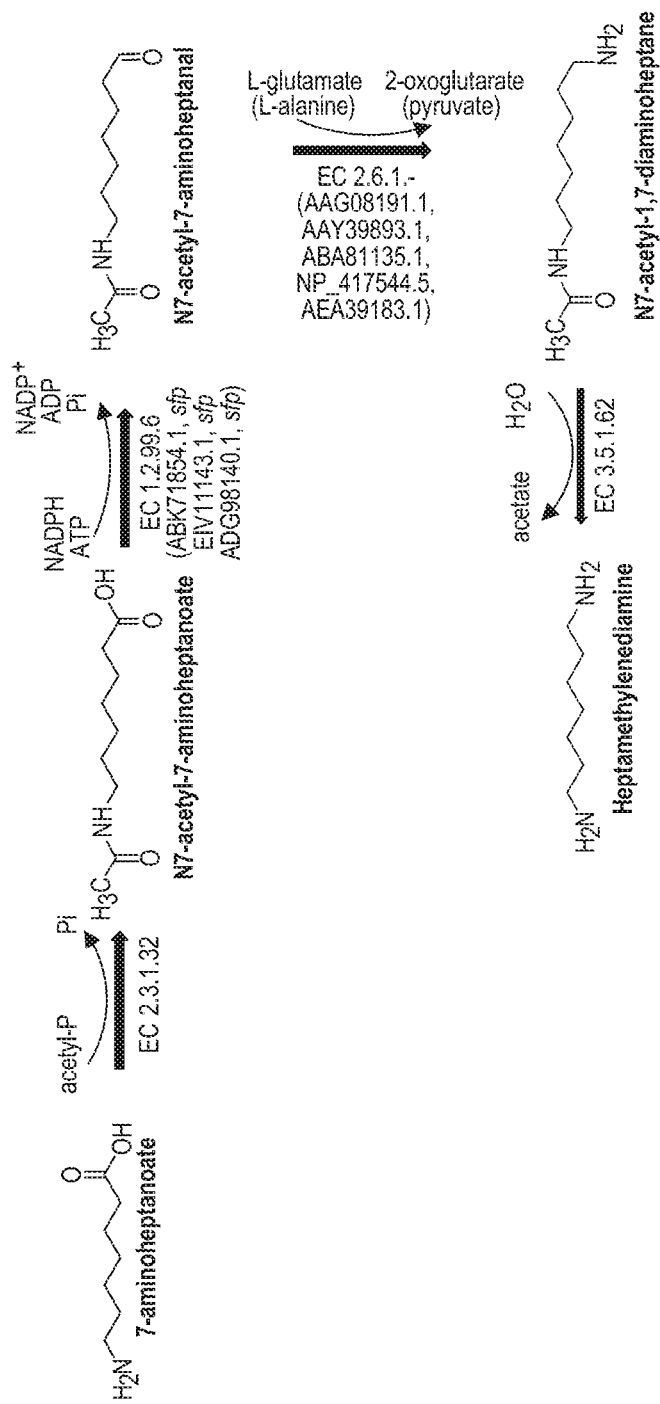
Figure 6C:
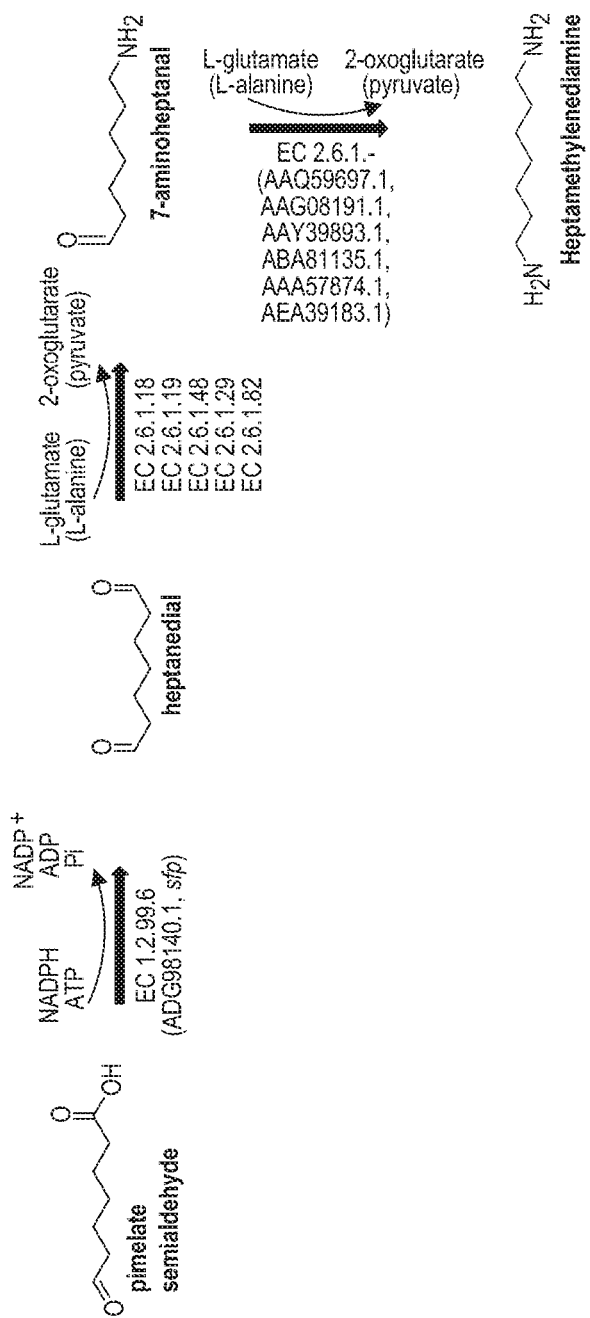

Conversion of pimelic acid to 7-AHA requires the activity of two enzymes, CAR and ω-TAM (FIG. 1). Five plasmids were constructed to enable the testing of two different promoters and three different versions of the CAR gene (FIG. 4). These plasmids were introduced into the ΔbioF strain and strains were analysed for 7-AHA production. All the strains with the full pathway present were found to produce 7-AHA (maximum level detected 0.03 mg/L) with the identity of the 7-AHA being confirmed by LC-MS/MS comparison to an authentic standard.

As shown in FIG. 4, two different promoters were used PBAD and PT7. Three variants of the CAR gene were used, the *S. rugosus* CAR, the *S. rugosus* improved CAR (CAR-69) and the *S. rotundus* CAR. The negative control plasmid pCDF_T7_ωta_lysE_sfp lacks a CAR gene. Plasmids were introduced into FERM BP-4928-P2(DE3)-4 ΔbioF. Strains were cultured in chemically defined medium and were grown for 24 to 72 hours following induction. Culture supernatants were analysed by LC-MS for 7-AHA. Titres of 7-AHA indicate the highest titre observed for each strain.

Example 5

Enzyme Activity of ω-Transaminase Using Pimelate Semialdehyde as Substrate and Forming 7-Aminoheptanoate A sequence encoding an N-terminal His-tag was added to the genes from *Chromobacterium violaceum*, *Pseudomonas syringae*, *Rhodobacter sphaeroides*, and *Vibrio Fluvialis* encoding the ω-transaminases of SEQ ID NOs: 8, 10, 11 and 13, respectively (see FIGS. 9C and 9D) such that N-terminal HIS tagged ω-transaminases could be produced. Each of the resulting modified genes was cloned into a pET21a expression vector under control of the T7 promoter and each expression vector was transformed into a BL21[DE3] *E. coli* host. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanoate to pimelate semialdehyde) were performed in a buffer composed of a final concentration of 50 mM HEPES buffer (pH=7.5), 10 mM 7-aminoheptanoate, 10 mM pyruvate and 100 μM pyridoxyl 5' phosphate. Each enzyme activity assay reaction was initiated by adding cell free extract of the ω-transaminase gene product or the empty vector control to the assay buffer containing the 7-aminoheptanoate and incubated at 25° C. for 4 h, with shaking at 250 rpm. The formation of L-alanine from pyruvate was quantified via RP-HPLC.

Each enzyme only control without 7-aminoheptanoate demonstrated low base line conversion of pyruvate to L-alanine. See FIG. 15. The gene product of SEQ ID NO 8, SEQ ID NO 10, SEQ ID NO 11 and SEQ ID NO 13 accepted 7-aminoheptanote as substrate as confirmed against the empty vector control. See FIG. 16.

Enzyme activity in the forward direction (i.e., pimelate semialdehyde to 7-aminoheptanoate) was confirmed for the transaminases of SEQ ID NO 10, SEQ ID NO 11 and SEQ ID NO 13. Enzyme activity assays were performed in a buffer composed of a final concentration of 50 mM HEPES buffer (pH=7.5), 10 mM pimelate semialdehyde, 10 mM L-alanine and 100 μM pyridoxyl 5' phosphate. Each enzyme activity assay reaction was initiated by adding a cell free extract of the ω-transaminase gene product or the empty vector control to the assay buffer containing the pimelate semialdehyde and incubated at 25° C. for 4 h, with shaking at 250 rpm. The formation of pyruvate was quantified via RP-HPLC.

The gene product of SEQ ID NO 10, SEQ ID NO 11 and SEQ ID NO 13 accepted pimelate semialdehyde as substrate as confirmed against the empty vector control. See FIG. 17. The reversibility of the ω-transaminase activity was confirmed, demonstrating that the ω-transaminases of SEQ ID NO 8, SEQ ID NO 10, SEQ ID NO 11, and SEQ ID NO 13 accepted pimelate semialdehyde as substrate and synthesized 7-aminoheptanoate as a reaction product.

Example 6

Enzyme Activity of Carboxylate Reductase Using Pimelate as Substrate and Forming Pimelate Semialdehyde A sequence encoding a HIS-tag was added to the genes from *Segniliparus rugosus* and *Segniliparus rotundus* that encode the carboxylate reductases of SEQ ID NOs: 4 and 7, respectively (see FIGS. 9B and 9C), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21[DE3] *E. coli* host and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an autoinduction media.

The pellet from each induced shake flask culture was harvested via centrifugation. Each pellet was resuspended and lysed via sonication, and the cell debris was separated from the supernatant via centrifugation. The carboxylate reductases and phosphopantetheine transferases were purified from the supernatant using Ni-affinity chromatography, diluted 10-fold into 50 mM HEPES buffer (pH=7.5), and concentrated via ultrafiltration.

Enzyme activity assays (i.e., from pimelate to pimelate semialdehyde) were performed in triplicate in a buffer composed of a final concentration of 50 mM HEPES buffer (pH=7.5), 2 mM pimelate, 10 mM MgCl$_2$, 1 mM ATP and 1 mM NADPH. Each enzyme activity assay reaction was initiated by adding purified carboxylate reductase and phosphopantetheine transferase gene products or the empty vector control to the assay buffer containing the pimelate and then incubated at room temperature for 20 min. The consumption of NADPH was monitored by absorbance at 340 nm. Each enzyme only control without pimelate demonstrated low base line consumption of NADPH. See FIG. 10.

The gene products of SEQ ID NO 4 and SEQ ID NO 7, enhanced by the gene product of sfp, accepted pimelate as substrate, as confirmed against the empty vector control (see FIG. 11), and synthesized pimelate semialdehyde.

Example 7

Enzyme Activity of Carboxylate Reductase Using 7-Hydroxyheptanoate as Substrate and Forming 7-Hydroxyheptanal A sequence encoding a His-tag was added to the genes from *Mycobacterium marinum*, *Mycobacterium smegmatis*, *Segniliparus rugosus*, *Mycobacterium smegmatis*, *Mycobacterium massiliense*, and *Segniliparus rotundus* that encode the carboxylate reductases of SEQ ID NOs: 2-7—respectively (see FIGS. 9A-9C) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter.

Each expression vector was transformed into a BL21 [DE3] *E. coli* host and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Enzyme activity (i.e., 7-hydroxyheptanoate to 7-hydroxyheptanal) assays were performed in triplicate in a buffer composed of a final concentration of 50 mM HEPES buffer (pH=7.5), 2 mM 7-hydroxyheptanal, 10 mM $MgCl_2$, 1 mM ATP, and 1 mM NADPH. Each enzyme activity assay reaction was initiated by adding purified carboxylate reductase and phosphopantetheine transferase or the empty vector control to the assay buffer containing the 7-hydroxyheptanoate and then incubated at room temperature for 20 min. The consumption of NADPH was monitored by absorbance at 340 nm. Each enzyme only control without 7-hydroxyheptanoate demonstrated low base line consumption of NADPH. See FIG. 10.

The gene products of SEQ ID NO 2-7, enhanced by the gene product of sfp, accepted 7-hydroxyheptanoate as substrate as confirmed against the empty vector control (see FIG. 12), and synthesized 7-hydroxyheptanal.

Example 8

Enzyme Activity of ω-Transaminase for 7-Aminoheptanol, Forming 7-Oxoheptanol

A nucleotide sequence encoding an N-terminal His-tag was added to the *Chromobacterium violaceum*, *Pseudomonas syringae* and *Rhodobacter sphaeroides* genes encoding the ω-transaminases of SEQ ID NOs: 8, 10 and 11, respectively (see FIG. 9C) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanol to 7-oxoheptanol) were performed in a buffer composed of a final concentration of 50 mM HEPES buffer (pH=7.5), 10 mM 7-aminoheptanol, 10 mM pyruvate, and 100 μM pyridoxyl 5' phosphate. Each enzyme activity assay reaction was initiated by adding cell free extract of the ω-transaminase gene product or the empty vector control to the assay buffer containing the 7-aminoheptanol and then incubated at 25° C. for 4 h, with shaking at 250 rpm. The formation of L-alanine was quantified via RP-HPLC.

Each enzyme only control without 7-aminoheptanol had low base line conversion of pyruvate to L-alanine. See FIG. 15.

The gene products of SEQ ID NO 8, 10 & 11 accepted 7-aminoheptanol as substrate as confirmed against the empty vector control (see FIG. 20) and synthesized 7-oxoheptanol as reaction product. Given the reversibility of the ω-transaminase activity (see Example 2), it can be concluded that the gene products of SEQ ID 8, 10 & 11 accept 7-oxoheptanol as substrate and form 7-aminoheptanol.

Example 9

Enzyme Activity of ω-Transaminase Using Heptamethylenediamine as Substrate and Forming 7-Aminoheptanal A sequence encoding an N-terminal His-tag was added to the *Chromobacterium violaceum*, *Pseudomonas aeruginosa*, *Pseudomonas syringae*, *Rhodobacter sphaeroides*, *Escherichia coli*, and *Vibrio fluvialis* genes encoding the ω-transaminases of SEQ ID NOs: 8-13, respectively (see FIGS. 9C and 9D) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., heptamethylenediamine to 7-aminoheptanal) were performed in a buffer composed of a final concentration of 50 mM HEPES buffer (pH=7.5), 10 mM heptamethylenediamine, 10 mM pyruvate, and 100 pyridoxyl 5' phosphate. Each enzyme activity assay reaction was initiated by adding cell free extract of the ω-transaminase gene product or the empty vector control to the assay buffer containing the heptamethylenediamine and then incubated at 25° C. for 4 h, with shaking at 250 rpm. The formation of L-alanine was quantified via RP-HPLC.

Each enzyme only control without heptamethylenediamine had low base line conversion of pyruvate to L-alanine. See FIG. 15.

The gene products of SEQ ID NO 8-13 accepted heptamethylenediamine as substrate as confirmed against the empty vector control (see FIG. 18) and synthesized 7-aminoheptanal as reaction product. Given the reversibility of the ω-transaminase activity (see Example 5), it can be concluded that the gene products of SEQ ID 8-13 accept 7-aminoheptanal as substrate and form heptamethylenediamine.

Example 10

Enzyme Activity of Carboxylate Reductase for N7-Acetyl-7-Aminoheptanoate, Forming N7-Acetyl-7-Aminoheptanal The activity of each of the N-terminal His-tagged carboxylate reductases of SEQ ID NOs: 3, 6, and 7 (see Examples 7, and FIGS. 9A, 9B, and 9C) for converting N7-acetyl-7-aminoheptanoate to N7-acetyl-7-aminoheptanal was assayed in triplicate in a buffer composed of a final concentration of 50 mM HEPES buffer (pH=7.5), 2 mM N7-acetyl-7-aminoheptanoate, 10 mM MgCl$_2$, 1 mM ATP, and 1 mM NADPH. The assays were initiated by adding purified carboxylate reductase and phosphopantetheine transferase or the empty vector control to the assay buffer containing the N7-acetyl-7-aminoheptanoate then incubated at room temperature for 20 min. The consumption of NADPH was monitored by absorbance at 340 nm. Each enzyme only control without N7-acetyl-7-aminoheptanoate demonstrated low base line consumption of NADPH. See FIG. 10.

The gene products of SEQ ID NO 3, 6, and 7, enhanced by the gene product of sfp, accepted N7-acetyl-7-aminoheptanoate as substrate as confirmed against the empty vector control (see FIG. 13), and synthesized N7-acetyl-7-aminoheptanal.

Example 11

Enzyme Activity of ω-Transaminase Using N7-Acetyl-1,7-Diaminoheptane, and Forming N7-Acetyl-7-Aminoheptanal The activity of the N-terminal His-tagged ω-transaminases of SEQ ID NOs: 8-13 (see Example 9, and FIGS. 9C and 9D) for converting N7-acetyl-1,7-diaminoheptane to N7-acetyl-7-aminoheptanal was assayed using a buffer composed of a final concentration of 50 mM HEPES buffer (pH=7.5), 10 mM N7-acetyl-1,7-diaminoheptane, 10 mM pyruvate and 100 μM pyridoxyl 5' phosphate. Each enzyme activity assay reaction was initiated by adding a cell free extract of the ω-transaminase or the empty vector control to the assay buffer containing the N7-acetyl-1,7-diaminoheptane then incubated at 25° C. for 4 h, with shaking at 250 rpm. The formation of L-alanine was quantified via RP-HPLC.

Each enzyme only control without N7-acetyl-1,7-diaminoheptane demonstrated low base line conversion of pyruvate to L-alanine. See FIG. 15.

The gene product of SEQ ID NO 8-13 accepted N7-acetyl-1,7-diaminoheptane as substrate as confirmed against the empty vector control (see FIG. 19) and synthesized N7-acetyl-7-aminoheptanal as reaction product.

Given the reversibility of the ω-transaminase activity (see example 2), the gene products of SEQ ID 8-13 accept N7-acetyl-7-aminoheptanal as substrate forming N7-acetyl-1,7-diaminoheptane.

Example 12

Enzyme Activity of Carboxylate Reductase Using Pimelate Semialdehyde as Substrate and Forming Heptanedial The N-terminal His-tagged carboxylate reductase of SEQ ID NO 7 (see Example 7 and FIG. 9C) was assayed using pimelate semialdehyde as substrate. The enzyme activity assay was performed in triplicate in a buffer composed of a final concentration of 50 mM HEPES buffer (pH=7.5), 2 mM pimelate semialdehyde, 10 mM MgCl$_2$, 1 mM ATP and 1 mM NADPH. The enzyme activity assay reaction was initiated by adding purified carboxylate reductase and phosphopantetheine transferase or the empty vector control to the assay buffer containing the pimelate semialdehyde and then incubated at room temperature for 20 min. The consumption of NADPH was monitored by absorbance at 340 nm. The enzyme only control without pimelate semialdehyde demonstrated low base line consumption of NADPH. See FIG. 10.

The gene product of SEQ ID NO 7, enhanced by the gene product of sfp, accepted pimelate semialdehyde as substrate as confirmed against the empty vector control (see FIG. 14) and synthesized heptanedial.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for regulating biosynthesis of at least one C7 building block chosen from pimelic acid, 7-aminoheptanoate, 7-hydroxyheptanoate, heptamethylenediamine, 7-aminoheptanol, and 1,7-heptanediol in a recombinant host using a pathway having a pimeloyl-ACP intermediate, said method comprising:

deleting the activity of an ACP-dependent BioF enzyme;
overexpressing a BioW enzyme and a CoA-specific BioF enzyme, wherein:
the BioW enzyme is a pimeloyl-CoA ligase having at least 85% sequence identity or homology to the amino acid sequence set forth in SEQ ID NO: 18; and
the CoA-specific BioF enzyme is an 8-amino-7-oxononanoate synthase having at least 85% sequence identity or homology to the amino acid sequence set forth in SEQ ID NO: 19; and
wherein the recombinant host is a prokaryote chosen from the genera *Escherichia, Clostridia, Corynebacteria, Cupriavidus, Pseudomonas, Delftia, Bacillus, Lactobacillus, Lactococcus*, and *Rhodococcus* or the recombinant host is a eukaryote chosen from the genera *Aspergillus, Saccharomyces, Pichia, Yarrowia, Issatchenkia, Debaryomyces, Arxula*, and *Kluyveromyces*; and
wherein the deletion of the activity of an ACP-dependent BioF enzyme occurs through a knockout of the BioF gene.

2. The method of claim 1, wherein:
said BioW enzyme enzymatically converts pimelic acid to pimeloyl-CoA; or
said CoA-specific BioF enzyme enzymatically converts pimeloyl-CoA to 8-amino-7-oxo-nonanoic acid.

3. The method of claim 1, wherein said pathway comprises:
enzymatically synthesizing a C7 aliphatic backbone from malonyl-ACP via two cycles of methyl-ester shielded carbon chain elongation; and
enzymatically forming two terminal functional groups in said backbone, thereby forming the C7 building block.

4. The method of claim 3, wherein:
a S-adenosyl-L-methionine (SAM)-dependent methyltransferase converts malonyl-ACP to malonyl-ACP methyl ester; and
said two cycles of methyl-ester shielded carbon chain elongation produce pimeloyl-ACP methyl ester from malonyl-ACP methyl ester using a trans-2-enoyl-CoA reductase.

5. The method of claim 3, wherein each of said two cycles of methyl-ester shielded carbon chain elongation comprises using (i) a β-ketoacyl-ACP synthase, (ii) a 3-oxoacyl-ACP reductase, (iii) a 3-hydroxyacyl-ACP dehydratase, and (iv) an enoyl-ACP reductase.

6. The method of claim 3, wherein:
a hydroxyl terminal group is enzymatically formed by a 6-hydroxyhexanoate dehydrogenase, a 5-hydroxypentanoate dehydrogenase, a 4-hydroxybutyrate dehydratase, or an alcohol dehydrogenase;
a carboxyl terminal group is enzymatically formed by a thioesterase, an aldehyde dehydrogenase, a 7-oxoheptanoate dehydrogenase, a 6-oxohexanoate dehydrogenase, a glutaconate CoA-transferase, or a reversible succinyl-CoA ligase; or
an amine terminal group is enzymatically formed by a ω-transaminase or a deacetylase.

7. The method of claim 1, wherein an intermediate with a terminal aldehyde group is formed by a carboxylate reductase and enhanced by a phosphopantetheinyl transferase during the biosynthesis of said at least one C7 building block.

8. The method of claim 1, wherein said method is performed in said recombinant host by fermentation.

9. The method of claim 8, wherein:
said recombinant host is subjected to a cultivation condition under aerobic, anaerobic, micro-aerobic or mixed oxygen/denitrification cultivation conditions;
said recombinant host is cultured under conditions of nutrient limitation;
said recombinant host is retained using a ceramic hollow fiber membrane to maintain a high cell density during fermentation; or
said recombinant host's tolerance to high concentrations of the at least one C7 building block is improved through continuous cultivation in a selective environment.

10. The method of claim 8, wherein:
the principal carbon source fed to the fermentation is a biological feedstock that is, or derives from, at least one feedstock chosen from monosaccharides, disaccharides, lignocellulose, hemicellulose, cellulose, lignin, levulinic acid, formic acid, triglycerides, glycerol, fatty acids, agricultural waste, condensed distillers' solubles, and municipal waste; or
the principal carbon source fed to the fermentation is a non-biological feedstock that is, or derives from, at least one feedstock chosen from natural gas, syngas, $CO_2/H_2$, methanol, ethanol, benzoate, non-volatile residue (NVR) caustic wash waste stream from cyclohexane oxidation processes, and terephthalic acid/isophthalic acid mixture waste streams.

11. The method of claim 1, wherein:
said prokaryote is *Escherichia coli, Clostridium ljungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Pseudomonas oleav-* orans, *Delftia acidovorans, Bacillus subtillis, Lactobacillus delbrueckii,* or *Lactococcus lactis;* said eukaryote is *Aspergillus niger, Saccharomyces cerevisiae, Pichia pastoris, Yarrowia lipolytica, Issathenkia orientalis, Debaryomyces hansenii, Arxula adenoinivorans,* or *Kluyveromyces lactis.*

12. The method of claim 1, wherein the knockout of the BioF gene occurs through homologous recombination.

* * * * *